(12) United States Patent
Ariyama et al.

(10) Patent No.: US 11,466,272 B2
(45) Date of Patent: Oct. 11, 2022

(54) NUCLEIC ACID SUPPRESSING EXPRESSION OF APCS

(71) Applicant: KYOWA KIRIN CO., LTD., Tokyo (JP)

(72) Inventors: Hiroyuki Ariyama, Tokyo (JP); Takuya Murakami, Tokyo (JP); Takashi Imaeda, Tokyo (JP); Tatsuya Miyazawa, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 52 days.

(21) Appl. No.: 16/617,743

(22) PCT Filed: May 31, 2018

(86) PCT No.: PCT/JP2018/020941
§ 371 (c)(1),
(2) Date: Nov. 27, 2019

(87) PCT Pub. No.: WO2018/221649
PCT Pub. Date: Dec. 6, 2018

(65) Prior Publication Data
US 2020/0190514 A1    Jun. 18, 2020

(30) Foreign Application Priority Data
May 31, 2017  (JP) ................ JP2017-108502

(51) Int. Cl.
*C12N 15/113*        (2010.01)
(52) U.S. Cl.
CPC ........ *C12N 15/113* (2013.01); *C12N 2310/11* (2013.01)
(58) Field of Classification Search
CPC .............. C12N 15/113; C12N 2310/14; C12N 2310/321; A61K 31/713; A61K 48/00; A61P 3/00
See application file for complete search history.

(56) References Cited

U.S. PATENT DOCUMENTS

| | | | |
|---|---|---|---|
| 6,126,918 A * | 10/2000 | Pepys ................... | A61K 49/14 424/9.1 |
| 6,291,668 B1 | 9/2001 | Ziegler et al. | |
| 8,394,628 B2 | 3/2013 | Tuschl et al. | |
| 8,420,391 B2 | 4/2013 | Tuschl et al. | |
| 8,552,171 B2 | 10/2013 | Tuschl et al. | |
| 8,632,997 B2 | 1/2014 | Tuschl et al. | |
| 8,742,092 B2 | 6/2014 | Tuschl et al. | |
| 8,790,922 B2 | 7/2014 | Tuschl et al. | |
| 9,012,138 B2 | 4/2015 | Tuschl et al. | |
| 9,012,621 B2 | 4/2015 | Tuschl et al. | |
| 9,193,753 B2 | 11/2015 | Tuschl et al. | |
| 10,472,625 B2 | 11/2019 | Tuschl et al. | |
| 2002/0086356 A1 | 7/2002 | Tuschl et al. | |
| 2003/0108923 A1 | 6/2003 | Tuschl et al. | |
| 2007/0003960 A1 | 1/2007 | Tuschl et al. | |
| 2007/0003961 A1 | 1/2007 | Tuschl et al. | |
| 2007/0003962 A1 | 1/2007 | Tuschl et al. | |
| 2007/0003963 A1 | 1/2007 | Tuschl et al. | |
| 2008/0113351 A1 | 5/2008 | Naito et al. | |
| 2008/0132461 A1 | 6/2008 | Tuschi et al. | |
| 2009/0186843 A1 | 7/2009 | Tuschl et al. | |
| 2011/0054005 A1 | 3/2011 | Naito et al. | |
| 2011/0150897 A1 | 6/2011 | Meyer et al. | |
| 2011/0244446 A1 | 10/2011 | Tuschl et al. | |
| 2011/0244568 A1 | 10/2011 | Tuschl et al. | |
| 2011/0245318 A1 | 10/2011 | Tuschl et al. | |
| 2011/0281931 A1 | 11/2011 | Tuschl et al. | |
| 2011/0289611 A1 | 11/2011 | Tuschl et al. | |
| 2012/0015042 A1 | 1/2012 | Tuschl et al. | |
| 2012/0029061 A1 | 2/2012 | Tuschl et al. | |
| 2012/0052487 A9 * | 3/2012 | Khvorova ................ | A61P 3/10 435/6.1 |
| 2012/0122111 A1 | 5/2012 | Tuschl et al. | |
| 2013/0198875 A1 | 8/2013 | Tuschl et al. | |
| 2016/0032288 A1 | 2/2016 | Tuschl et al. | |
| 2020/0270602 A1 | 8/2020 | Tuschl et al. | |

FOREIGN PATENT DOCUMENTS

| | | |
|---|---|---|
| WO | 98/56905 | 12/1998 |
| WO | 01/75164 | 10/2001 |
| WO | 2005/116204 | 12/2005 |

(Continued)

OTHER PUBLICATIONS

Jackson et al (Nature Biotech. 21(6):636-637, 2002) (Year: 2002).*
Allerson et al (J. Med. Chem. 2005, 48, 901-904) (Year: 2005).*
International Search Report dated Jul. 17, 2018 in International (PCT) Application No. PCT/JP2018/020941 with English-language translation.
Pepys et al., "Amyloid P component. A critical review", The Journal of Protein Folding Disorders, 1997, vol. 4, pp. 274-295.
Hawkins et al., "Evaluation of Systemic Amyloidosis by Scintigraphy With [123]I-Labeled Serum Amyloid P Component", The New England Journal of Medicine, 1990, vol. 323, pp. 508-513.
Bodin et al., "Antibodies to human serum amyloid P component eliminate visceral amyloid deposits", Nature, 2010, vol. 468, pp. 93-97.
Richards et al., "Therapeutic Clearance of Amyloid by Antibodies to Serum Amyloid P Component", The New England Journal of Medicine, 2015, vol. 373, pp. 1106-1114.

(Continued)

*Primary Examiner* — Richard A Schnizer
(74) *Attorney, Agent, or Firm* — Wenderoth, Lind & Ponack, L.L.P.

(57) ABSTRACT

The present invention provides a double-stranded nucleic acid consisting of a sense-strand nucleic acid and an antisense-strand nucleic acid and comprising a double-strand region having at least 11 base pairs, for suppressing expression of APCS gene, in which an oligonucleotide chain having a chain length of at least 17 nucleotides and at most 30 nucleotides in the antisense-strand nucleic acid is complementary to a target APCS mRNA sequence comprising a base sequence set forth in any one of SEQ ID NOS: 1288 to 1930.

14 Claims, No Drawings
Specification includes a Sequence Listing.

(56) References Cited

FOREIGN PATENT DOCUMENTS

WO         2008/043561       4/2008
WO         WO-2019100039 A1 *    5/2019            A61K 31/713

OTHER PUBLICATIONS

Muczynski et al., "Complex formation with pentraxin-2 regulates factor X plasma levels and macrophage interactions", The American Society of Hematology, 2017, vol. 129, No. 17, pp. 2443-2454.
Botto et al., "Amyloid deposition is delayed in mice with targeted deletion of the serum amyloid P component gene", Nature Medicine, 1997, vol. 3, No. 8, pp. 885-859.
Mantzouranis et al., "Human Serum Amyloid P Component", The Journal of Biological Chemistiy, 1985, vol. 260, No. 12, pp. 7752-7756.
Pepys et al., "Targeted pharmacological depletion of serum amyloid P component for treatment of human amyloidosis", Nature, 2002, vol. 417, No. 6886, pp. 254-259.

* cited by examiner

… … …

NUCLEIC ACID SUPPRESSING EXPRESSION OF APCS

TECHNICAL FIELD

The present invention relates to a nucleic acid that suppresses expression of APCS or a pharmaceutical composition comprising the nucleic acid.

BACKGROUND ART

APCS (amyloid P component, serum; also referred to as Serum amyloid P, SAP or Pentraxin-2) has a pentamer structure of a glycoprotein constituted of 223 amino acids. APCS is a protein produced in the liver and present in the blood at a relatively high concentration of 30 to 50 µg/mL.

APCS has a biochemical property of binding to all types of amyloid fibrils in a calcium-dependent manner. It is known that APCS is contained in an amount as large as 20,000 mg in amyloid of patients having amyloid (non-Patent Literature 1).

Since APCS is present in amyloid of all patients with an amyloid-related disease, APCS is used as a diagnostic marker in patients with an amyloid-related disease (non-Patent Literature 2).

The amyloid-related disease is a disease causing organ damage, which is caused by accumulation of abnormal insoluble protein-fibers (known as amyloid fibrils) on a tissue.

It has been clarified that amyloid to which APCS binds can be stabilized by APCS inducing resistance to decomposition with protease and phagocytosis by immune cells. Also, researches and clinical studies using animal models strongly suggest that amyloid accumulation on organs and tissue disorders associated to the accumulation can be reduced by inhibiting binding of APCS to amyloid (non-Patent Literatures 3, 4). It is expected that amyloid-related diseases can be prevented or treated by specifically suppressing expression of APCS; however, pharmaceutical products that specifically suppresses expression of APCS have not yet been reported up to present.

As a method for suppressing expression of a gene, itself, for example, a method of using RNA interference (also referred to as RNAi) is known. More specifically, it has been found that expression of a target gene is specifically suppressed by introduction of double strand RNA having the same sequence as a target gene, and the RNA is called as short interfering RNA (siRNA) (Patent Literature 1). Alternatively, as a method for suppressing expression of a gene other than RNA interference, an antisense method is known (Patent Literature 2).

A part of the siRNA sequence targeting human APCS mRNA is disclosed; however, it has not been known that the siRNA sequence suppresses expression of human APCS (Patent Literatures 3, 4).

CITATION LIST

Patent Literatures

Patent Literature 1: International Publication No. WO2001/75164
Patent Literature 2: International Publication No. WO98/56905
Patent Literature 3: International Publication No. WO2005/116204
Patent Literature 4: International Publication No. WO2008/043561

Non Patent Literature 1: Amyloid, 4: 4, 274-295 (1997)
Non Patent Literature 2: N. Engl. J. Med. 1990; 323: 508-13
Non Patent Literature 3: Nature 468: 93-97. (2010)
Non Patent Literature 4: N. Engl. J. Med. 373: 1106-14. (2015)

SUMMARY OF INVENTION

Technical Problem

An object of the present invention is to provide a nucleic acid capable of suppressing the expression of APCS.

Solution to Problem

The present invention relates to the following (1) to (13).

(1) A double-stranded nucleic acid consisting of a sense-strand nucleic acid and an antisense-strand nucleic acid and comprising a double-strand region having at least 11 base pairs, for suppressing expression of APCS gene, wherein an oligonucleotide chain having a chain length of at least 17 nucleotides and at most 30 nucleotides in the antisense-strand nucleic acid is complementary to a target APCS mRNA sequence comprising a base sequence set forth in any one of SEQ ID NOS: 1288 to 1930.

(2) The double-stranded nucleic acid according to (1), wherein the double-strand region has 11 to 27 base pairs and a nucleotide at position 2 counted from a 5' end of the antisense-strand nucleic acid is complementary to a nucleotide at position 2 counted from a 3' end of the target APCS mRNA sequence.

(3) The double-stranded nucleic acid according to (1) or (2), wherein a 3' end of the sense-strand nucleic acid and a 5' end of the antisense-strand nucleic acid and/or the 5' end of the sense-strand nucleic acid and the 3' end of the antisense-strand nucleic acid form a blunt end.

(4) The double-stranded nucleic acid according to any one of (1) to (3), wherein the sense-strand nucleic acid has a chain length of 21 nucleotides and the antisense-strand nucleic acid has a chain length of 21 nucleotides.

(5) The double-stranded nucleic acid according to (4), comprising a double-strand region having 19 base pairs, in which 40 to 65% of the nucleotides in the double-strand region are 2'-O-methyl modified nucleotides.

(6) The double-stranded nucleic acid according to any one of (1) to (5), wherein the antisense-strand nucleic acid comprises a base sequence set forth in any one of SEQ ID NOS: 645 to 1287 and 1975 to 2018.

(7) The double-stranded nucleic acid according to any one of (1) to (6), wherein the sense-strand nucleic acid comprises a base sequence set forth in any one of SEQ ID NOS: 2 to 644 and 1931 to 1974.

(8) The double-stranded nucleic acid according to any one of (1) to (7), wherein the sense-strand nucleic acid comprises a base sequence set forth in any one of SEQ ID NOS: 2 to 644 and 1931 to 1974, and correspondingly thereto, the antisense-strand nucleic acid comprises a base sequence set forth in any one of SEQ ID NOS: 645 to 1287 and 1975 to 2018.

(9) The double-stranded nucleic acid according to any one of (1) to (8), comprising a ligand.

(10) A single-stranded nucleic acid consisting of only the antisense-strand nucleic acid of the double-stranded nucleic acid according to any one of (1) to (9).

(11) A pharmaceutical composition comprising the nucleic acid according to any one of (1) to (10).

(12) A method for treating a disorder mediated by APCS-containing amyloid fibrils, comprising a step of administering a therapeutically effective amount of the nucleic acid according to any one of (1) to (10) or the pharmaceutical composition according to (11) to a human in need of such a treatment.

(13) The method according to (12), wherein the disorder is an amyloid-related disease.

Advantageous Effects of Invention

According to the present invention, it is possible to provide a nucleic acid capable of suppressing the expression of APCS.

DESCRIPTION OF EMBODIMENTS

A target of the nucleic acid of the present invention, APCS mRNA, is homologous to the sequence of SEQ ID NO: 1 registered in the Genbank under Accession No. NM_001639.3 and full-length mRNA of APCS having a base sequence, in which T of the sequence of SEQ ID NO: 1 is replaced by U. Herein, the complementary DNA of mRNA is defined as 1st strand cDNA, and a DNA, which is to be synthesized based on the 1st strand cDNA in order to obtain a double strand, is defined as the 2nd strand cDNA. In this case, SEQ ID NO: 1 represents the base sequence of the 2nd strand cDNA of APCS. Note that the base sequence of APCS mRNA and the base sequence of the 2nd strand cDNA of APCS are homologous.

1. Nucleic Acid of the Present Invention

In the present invention, a nucleic acid comprising the base sequence complementary to the APCS mRNA sequence is referred to as an antisense-strand nucleic acid; whereas a nucleic acid comprising the base sequence complementary to the base sequence of the antisense-strand nucleic acid is referred to as a sense-strand nucleic acid. As used herein, "the nucleic acid of the present invention", until otherwise specified, means nucleic acids including a single-stranded nucleic acid that is an antisense-strand nucleic acid or a sense-strand nucleic acid, and a double-stranded nucleic acid formed by pairing of the antisense-strand nucleic acid and the sense-strand nucleic acid.

The nucleic acid of the present invention may be any molecule as long as the molecule is a polymer of a nucleotide or a polymer of a molecule having the same function as a nucleotide. Examples of the nucleic acid include a ribonucleotide polymer, i.e., RNA; a deoxyribonucleotide polymer, i.e., DNA; a polymer of a ribonucleotide and deoxyribonucleotide, i.e., a chimeric nucleic acid; and a nucleotide polymer prepared by replacing at least one nucleotide of these nucleic acids (RNA, DNA, and chimeric nucleic acid) by a molecule having the same function as the nucleotide. Uracil (U) in RNA is univocally replaced by thymine (T) in DNA.

An example of the molecule having the same function as a nucleotide is a nucleotide derivative obtained by modifying a nucleotide.

Although it is not particularly limited, use of a nucleotide derivative has the advantages: for example, resistance against nuclease can be improved or stabilized compared to RNA or DNA; affinity for a complementary strand nucleic acid can be improved; cell permeability can be improved; and/or visualization can be made.

Examples of the nucleotide derivative include a nucleotide modified in the sugar portion, a nucleotide modified in a phosphate-diester bond, a nucleotide modified in a base and a nucleotide modified in two or more elements of a sugar portion, a phosphate diester bond and a base.

As the nucleotide modified in the sugar portion, any nucleotide may be used as long as part or whole of the chemical structure of the nucleotide sugar is modified or substituted with a substituent, or substituted with an atom; however, a 2'-modified nucleotide is preferably used.

Examples of the 2'-modified nucleotide include a 2'-modified nucleotide obtained by substituting 2'-OH group of the ribose with a substituent selected from the group consisting of OR, R, R'OR, SH, SR, $NH_2$, NHR, $NR_2$, $N_3$, CN, F, Cl, Br, and I (R represents an alkyl or aryl, preferably an alkyl having 1 to 6 carbon atoms, R' represents an alkylene, preferably an alkylene having 1 to 6 carbon atoms and two Rs of $NR_2$ may be the same or different).

As the 2'-modified nucleotide, e.g., 2'-modified nucleotides obtained by substituting the 2'-OH group of the ribose with F and a methoxy group, respectively (referred to as 2'-F modified nucleotide and 2'-O-methyl modified nucleotide, respectively) are preferably used.

An example of the 2'-modified nucleotide is a 2'-modified nucleotide obtained by substituting the 2'-OH group of the ribose with a substituent selected from the group consisting of a 2-(methoxy)ethoxy group, a 3-aminopropoxy group, a 2-[(N,N-dimethylamino)oxy]ethoxy group, a 3-(N,N-dimethylamino)propoxy group, a 2-[2-(N,N-dimethylamino)ethoxy]ethoxy group, 2-(methylamino)-2-oxoethoxy group, 2-(N-methylcarbamoyl)ethoxy group and a 2-cyanoethoxy group An example of the nucleotide modified in the sugar portion is an artificial Bridged Nucleic Acid (BNA) having two ring structures, which are obtained by introducing a cross-linked structure in the sugar portion. Specific examples thereof include an artificial Locked Nucleic Acid (LNA) in which a 2'-position oxygen atom and a 4'-position carbon atom are crosslinked via methylene ([Tetrahedron Letters, 38, 8735, (1997) and Tetrahedron, 54, 3607, (1998)], artificial Ethylene bridged nucleic acid) (ENA) [Nucleic Acid Research, 32, e175 (2004)], Constrained Ethyl (cEt) [The Journal of Organic Chemistry 75, 1569 (2010)], Amido-Bridged Nucleic Acid (AmNA) [Chem Bio Chem 13, 2513 (2012)] and 2'-O, 4'-c-Spirocyclopropylene bridged nucleic acid (scpBNA) [Chem. Commun., 51, 9737 (2015)].

Examples of the nucleotide modified in the sugar portion include a peptide nucleic acid (PNA) [Acc. Chem. Res., 32, 624 (1999)], an oxypeptide nucleic acid (OPNA) [J. Am. Chem. Soc., 123, 4653 (2001)] and a peptide ribonucleic acid (PRNA) [J. Am. Chem. Soc., 122, 6900 (2000)].

As the nucleotide modified in the phosphate diester bond, any nucleotide may be used as long as part or whole of the chemical structure of a phosphate diester bond of the nucleotide is modified or substituted with a substituent or substituted with an atom.

Examples of the nucleotide modified in the phosphate diester bond include a nucleotide obtained by substituting the phosphate diester bond with a phosphorothioate bond, a nucleotide obtained by substituting the phosphate diester bond with a phosphorodithioate bond, a nucleotide obtained by substituting the phosphate diester bond with an alkylphosphonate bond and a nucleotide obtained by substituting the phosphate diester bond with a phosphoramidate bond.

As the nucleotide modified in a base, any nucleotide may be used as long as part or whole of the chemical structure of a base of the nucleotide is modified or substituted with a substituent or substituted with an atom.

Examples of the nucleotide modified in a base include a nucleotide obtained by substituting the oxygen atom in the base with a sulfur atom, a nucleotide obtained by substituting a hydrogen atom with an alkyl group having 1 to 6 carbon atoms or halogen, a nucleotide obtained by substituting the methyl group with hydrogen, hydroxymethyl or an alkyl group having 2 to 6 carbon atoms, and a nucleotide obtained by substituting the amino group with an alkyl group having 1 to 6 carbon atoms, an alkanoyl group having 1 to 6 carbon atoms, an oxo group or a hydroxy group. Note that, using 5-methylcytosine (5-mC) in place of cytosine (C) as a nucleotide modified in a base is a preferable embodiment of the present invention.

Further examples of the nucleotide derivative include nucleotide derivatives obtained by adding, directly or via a linker, to a nucleotide or a nucleotide derivative as mentioned above, a chemical substance such as a ligand; a lipid such as cholesterol, a fatty acid, tocopherol and retinoid; a sugar such as N-acetylgalactosamine (GalNAc), galactose (Gal) and mannose (Man); a full antibody; a fragment antibody such as, Fab, scFv and VHH; a protein such as a low-density lipoprotein (LDL) and human serum albumin; a peptide such as RGD, NGR, R9 and CPP; a low molecule such as phenazine, phenanthridine, anthraquinone and folic acid; a synthetic polymer such as a synthetic polyamino acid; a nucleic acid aptamer; a pigment such as, acridine, fluorescein, rhodamine and coumarin; and a fluorophore such as Cy3 series, Alexa series (registered trademark) and a black hole quencher. Specific examples thereof include a polyamine-added nucleotide derivative, a cholesterol-added nucleotide derivative, a steroid added nucleotide derivative, a GalNAc added nucleotide derivative, a bile acid-added nucleotide derivative, a fatty acid-added nucleotide derivative, a vitamin-added nucleotide derivative, a Cy5 added nucleotide derivative, a Cy3 added nucleotide derivative, a 6-FAM added nucleotide derivative and a biotinylated nucleotide derivative. Preferably, a GalNAc added nucleotide derivative is mentioned. These derivatives can be modified at the 5' end and/or the 3' end, and/or within the sequence by reacting with a reactive modifier on a solid phase during an elongation reaction on the solid phase. Alternatively, a nucleic acid having a functional group such as an amino group, a mercapto group, an azido group, or a triple bond introduced therein, is synthesized and purified in advance; and a modifier may be allowed to react with the functional group.

A nucleotide derivative may have a cross-linked structure, which is formed with another nucleotide within the nucleic acid or a nucleotide derivative, and an alkylene structure, a peptide structure, a nucleotide structure, an ether structure, an ester structure, and a structure consisting of at least two of these, in combination.

The nucleic acid of the present invention includes a nucleic acid obtained by substituting part or all atoms in the nucleic acid molecule with an atom (isotope) different in mass number.

As used herein, "complementary" refers to the relationship between two bases that can be paired, for example, the relationship between adenine and thymine or uracil and the relationship between guanine and cytosine. Likewise, complementary bases are paired through a gentle hydrogen bond and form a double helix structure in the whole double-strand region. In the relationship between adenine and thymine or uracil and the relationship between guanine and cytosine, even though at least one of the bases in each of pairs of A and T (U) and G and C is a modified base, if the base pairing can be formed via a gentle hydrogen bond between two bases, the relationship between these bases can be complementary.

As used herein, "complementary" means not only the case where two nucleotide sequences are completely complementary but also the cases where a mismatch ratio between two nucleotide sequences is 0 to 30%, preferably 0 to 20% and more preferably 0 to 10%. More specifically, an antisense-strand nucleic acid complementary to the APCS mRNA sequence includes a completely complementary base sequence with a partial base sequence of the mRNA or a base sequence having a substitution(s) of one or more bases in the completely complementary base sequence. The antisense-strand nucleic acid may have 1 to 8, preferably 1 to 6, more preferably 1 to 4, further preferably 1 to 3, particularly preferably 1 to 2, particularly more preferably a single mismatch base with the target sequence of a target gene.

More specifically, in the case of the antisense-strand nucleic acid having a chain length of 21 nucleotides (21 base length), the number of mismatch bases with the target nucleotide sequence of a target gene may be 1 to 6, preferably 1 to 5, more preferably 1 to 4, further preferably 1 to 3, particularly preferably 1 to 2 and particularly more preferably a single. The mismatch position may be 5' end or the 3' end of each of the nucleotide sequences of antisense-strands.

As used herein, "complementary" refers to a case where one of the two nucleotide sequences is completely complementary to the other nucleotide sequence; however, the complementary sequence having addition and/or deletion of one or more bases is also included. In the present invention, the antisense-strand nucleic acid is a completely complementary base sequence to the APCS mRNA sequence; however, the antisense-strand nucleic acid may have additional bases, in other words, a single or two bulge bases to a target APCS mRNA sequence.

In the present invention, an antisense-strand nucleic acid or a sense-strand nucleic acid may have a single or two bulge bases.

In the present invention, the "bulge base" refers to a base which does not form a complementary base pair with the other nucleotide sequence.

As the antisense-strand nucleic acid of the present invention, a nucleic acid comprising a completely complementary base sequence with a target APCS mRNA sequence is used; however, the same nucleic acid as the above nucleic acid except that deletion, substitution or addition of 1 to 3 bases, preferably 1 to 2 bases and more preferably a single base are present, may be used.

The nucleic acid that suppresses expression of APCS, which is preferably used is double-stranded nucleic acid, which consists of a single-stranded nucleic acid being a nucleic acid (antisense-strand nucleic acid) comprising a base sequence complementary to a target APCS mRNA sequence or a nucleic acid (antisense-strand nucleic acid) comprising a base sequence complementary to a target APCS mRNA sequence, and a nucleic acid (sense-strand nucleic acid) comprising a base sequence complementary to the base sequence of the nucleic acid.

In the present invention, expression of APCS gene can be suppressed by the antisense-strand nucleic acid.

The double-stranded nucleic acid of the present invention is a double-stranded nucleic acid consisting of a sense-strand nucleic acid and an antisense-strand nucleic acid and comprising a double-strand region having at least 11 base pairs, for suppressing expression of APCS gene, in which an oligonucleotide chain having a chain length of at least 17 nucleotides and at most 30 nucleotides in the antisense-strand nucleic acid, is complementary to a targets APCS mRNA sequence comprising a base sequence set forth in any one of SEQ ID NOS: 1288 to 1930.

The base sequence set forth in any one of SEQ ID NOS: 1288 to 1930 is listed in Table 1.

In the double-stranded nucleic acid of the present invention, the sense-strand nucleic acid and the antisense-strand nucleic acid each may be constituted of any nucleotides or nucleotide derivatives.

The antisense-strand nucleic acid used in the double-stranded nucleic acid of the present invention is a nucleotide chain comprising a base sequence complementary to a target APCS mRNA sequence.

The target APCS mRNA sequence is homologous with SEQ ID NO: 1 and comprises a base sequence set forth in any one of SEQ ID NOS: 1288 to 1930 of the APCS mRNA sequences wherein T in SEQ ID NO: 1 is replaced by U. Preferably, the target APCS mRNA sequence is homologous with SEQ ID NO: 1 and a base sequence set forth in any one of SEQ ID NOS: 1288 to 1930 of the base sequences of APCS mRNA wherein T in SEQ ID NO: 1 is replaced by U.

In the double-stranded nucleic acid of the present invention, an oligonucleotide chain having a chain length of at least 17 nucleotides and at most 30 nucleotides, which constitute the antisense-strand nucleic acid, is complementary to the target APCS mRNA sequence.

In the present invention, an oligonucleotide chain having a chain length of preferably 11 to 27 nucleotides, more preferably 15 to 25 nucleotides, further preferably 15 to 23 nucleotides, particularly preferably 17 to 21 nucleotides, particularly more preferably 17 to 19 nucleotides and particularly further preferably 19 nucleotides, which constitute an antisense-strand nucleic acid, is complementary to the target APCS mRNA sequence.

In the present invention, the antisense-strand nucleic acid and the sense-strand nucleic acid comprise a double-strand region having at least 11 base pairs, usually 11 to 30 nucleotides, preferably 11 to 27 base pairs, more preferably 15 to 25 base pairs, further preferably 15 to 23 base pairs, particularly preferably 17 to 21 base pairs, particularly more preferably 17 to 19 base pairs, and particularly further preferably 19 base pairs.

In the present invention, a 2'-modified nucleotide is preferably contained in the nucleotides in the double-strand region and may be present in any site thereof. The suitable content of the 2'-modified nucleotide may be 10 to 20%, 20 to 40% and 40 to 65% based on the total amount (100%) of the nucleotides.

A specific example of the double-stranded nucleic acid containing a 2'-modified nucleotide is a double-stranded nucleic acid consisting of a pair of sense-strand/antisense-strand sequences selected from the group consisting of the sense-strands/antisense-strands listed in Table 3.

In the present invention, the suitable content of the 2'-modified nucleotide relative to the sense-strand nucleic acid may be 20 to 40%, 40 to 60% or 60% to 100%.

In the present invention, the suitable content of the 2'-modified nucleotide relative to the antisense-strand nucleic acid may be preferably 0 to 40%, 10 to 20% or 20 to 40%.

An antisense-strand nucleic acid and sense-strand nucleic acid (as a single strand) constituting a double-stranded nucleic acid each usually consist of 17 to 30 bases and preferably 17 to 27 bases, more preferably 17 to 25 bases, further preferably 17 to 25 bases and particularly preferably 19 to 25 bases. The base length of the antisense-strand nucleic acid and sense-strand nucleic acid may be the same or different.

In the present invention, the antisense-strand nucleic acid preferably comprises a base sequence set forth in any one of SEQ ID NOS: 645 to 1287 and 1975 to 2018; and the sense-strand nucleic acid preferably comprises a base sequence set forth in any one of SEQ ID NOS: 2 to 644 and 1931 to 1974.

In the present invention, the antisense-strand nucleic acid is more preferably a nucleotide strand having a base sequence set forth in any one of SEQ ID NOS: 645 to 1287 and 1975 to 2018; whereas the sense-strand nucleic acid is more preferably a nucleotide strand having a base sequence set forth in any one of SEQ ID NOS: 2 to 644 and 1931 to 1974.

In the double-stranded nucleic acid of the present invention, the sense-strand nucleic acid comprises a base sequence set forth in any one of SEQ ID NOS: 2 to 644 and 1931 to 1974; and correspondingly thereto, the antisense-strand nucleic acid preferably comprises a base sequence set forth in any one of SEQ ID NOS: 645 to 1287 and 1975 to 2018.

As used herein, the phrase "correspondingly thereto" means a combination of the sense-strand nucleic acid and the antisense-strand nucleic acid described in the each column of double-stranded nucleic acid numbers in Table 1 or Table 3, and SEQ ID NO: n (n=2 to 644) corresponds to SEQ ID NO: n+643. To give a specific example, SEQ ID NO: 2 corresponds to SEQ ID NO: 645.

In the double-stranded nucleic acid of the present invention, it is more preferable that a sense-strand nucleic acid is a nucleotide chain having a base sequence set forth in any one of SEQ ID NOS: 2 to 644 and 1931 to 1974; and correspondingly thereto, the antisense-strand nucleic acid is a nucleotide chain having a base sequence set forth in any one of SEQ ID NOS: 645 to 1287 and 1975 to 2018.

The double-stranded nucleic acid of the present invention has a double-strand region followed by an (additional) nucleotide or nucleotide derivative forming no double strand at the 3'-end side or the 5'-end side, the nucleotide or nucleotide derivative forming no double strand is called as a protrusion (overhang). If an overhang is present, the nucleotides constituting the overhang may be ribonucleotides, deoxyribonucleotides or derivatives of these.

As the double-stranded nucleic acid having an overhang, a double-stranded nucleic acid having an overhang consisting of usually 1 to 6 bases and preferably 1 to 3 bases at the 3' end or the 5' end of at least one of the sense-strand nucleic acid and antisense-strand nucleic acid, is used. A double-stranded nucleic acid having an overhang consisting of 2 bases is more preferably used, and an example thereof is a double-stranded nucleic acid having an overhang consisting of dTdT (dT represents thymidine) or UU. The overhang can be present in an antisense-strand nucleic acid alone or a sense-strand nucleic acid alone and both of the antisense-strand nucleic acid and the sense-strand nucleic acid. In any one of the cases where the overhang is present at an antisense-strand nucleic acid alone, a sense-strand nucleic acid alone and both of the antisense-strand nucleic acid and the sense-strand nucleic acid, the overhang may be present at the 3' end and/or the 5' end of the nucleic acid.

The antisense-strand nucleic acid to be used in the present invention, preferably, an oligonucleotide chain consisting of at least 17 nucleotides and at most 30 nucleotides including a double-strand region with the sense-strand nucleic acid and the following overhang is sufficiently complementary to a target APCS mRNA sequence comprising a base sequence set forth in any one of SEQ ID NOS: 1288 to 1930.

Examples of the double-stranded nucleic acid of the present invention that can be used include a nucleic acid molecule (WO2005/089287) producing the aforementioned double-stranded nucleic acid by the action of a ribonuclease such as Dicer; a double-stranded nucleic acid having a blunt end without an overhang at the 3' end or the 5' end; and a double-stranded nucleic acid (US2012/0040459) having an overhang of only a sense-strand nucleic acid. In the present invention, the "blunt end" means an end of a double-stranded nucleic acid having no overhang. The blunt end refers to, for example, a double-stranded nucleic acid where both the 3' end of a sense-strand nucleic acid and the 5' end of the antisense-strand nucleic acid have no overhang and/or both the 5' end of the sense-strand nucleic acid and the 3' end of the antisense-strand nucleic acid have no overhang.

In the present invention, it is preferable that both of the 3' end of a sense-strand nucleic acid and the 5' end of the antisense-strand nucleic acid and/or both of the 5' end of the sense-strand nucleic acid and the 3' end of the antisense-strand nucleic acid form a blunt end(s). Particularly, it is more preferable that the 3' end of a sense-strand nucleic acid and the 5' end of the antisense-strand nucleic acid, or the 5' end of the sense-strand nucleic acid and the 3' end of the antisense-strand nucleic acid forms a blunt end. If the 3' end of a sense-strand nucleic acid and the 5' end of the antisense-strand nucleic acid and/or the 5' end of the sense-strand nucleic acid and the 3' end of the antisense-strand nucleic acid form a blunt end(s), it is preferable that the sense-strand nucleic acid has a chain length of 21 nucleotides; whereas the antisense-strand nucleic acid has a chain length of 23 nucleotides.

In the present invention, it is also preferable that a double-stranded nucleic acid having an overhang at both of the antisense-strand nucleic acid and sense-strand nucleic acid. It is preferable that the 3' end of the sense-strand nucleic acid and the 3' end of the antisense-strand nucleic acid or the 5' end of the sense-strand nucleic acid and the 5' end of the antisense-strand nucleic acid have an overhang. If both of the antisense-strand nucleic acid and sense-strand nucleic acid have an overhang, it is preferable that the sense-strand nucleic acid has a chain length of 21 nucleotides and the antisense-strand nucleic acid has a chain length of 21 nucleotides.

In the present invention, it is more preferable that both of the 3' end and the 5' end of the sense-strand nucleic acid or both of the 3' end and the 5' end of the antisense-strand nucleic acid have an overhang.

It is preferable that the nucleotide at position 2 counted from the 5' end of an antisense-strand nucleic acid of the present invention is completely complementary to the ribonucleotide at position 2 counted from the 3' end of a target APCS mRNA sequence. It is more preferable that the ribonucleotides at positions 2 to 7 counted from the 5' end of the antisense-strand nucleic acid are completely complementary to the ribonucleotides at positions 2 to 7 counted from the 3' end of the target APCS mRNA sequence, respectively. It is further preferable that the ribonucleotides at positions 2 to 11 counted from the 5' end of the antisense-strand nucleic acid are completely complementary to the ribonucleotides at positions 2 to 11 counted from the 3' end of the target APCS mRNA sequence, respectively.

It is preferable that the nucleotide at position 11 counted from the 5' end of an antisense-strand nucleic acid of the present invention is completely complementary to the ribonucleotide at position 11 counted from the 3' end of a target APCS mRNA sequence. It is more preferable that the ribonucleotides at positions 9 to 13 counted from the 5' end of the antisense-strand nucleic acid are completely complementary to the ribonucleotides at positions 9 to 13 counted from the 3' end of the target APCS mRNA sequence, respectively. It is further preferable that the ribonucleotides at positions 7 to 15 counted from the 5' end of the antisense-strand nucleic acid are completely complementary to the ribonucleotides at positions 7 to 15 counted from the 3' end of the target APCS mRNA sequence, respectively.

A method for producing the nucleic acid of the present invention is not particularly limited, and examples thereof include a method using chemical synthesis known in the art and an enzymatic transcription method.

Examples of the method using chemical synthesis known in the art include a phosphoramidite method, phosphorothioate method, phosphotriester method and CEM method [Nucleic Acid Research, 35, 3287 (2007)]. The nucleic acid of the present invention can be synthesized, for example, by ABI3900 high-throughput nucleic acid synthesizer (manufactured by Applied Biosystems). After completion of synthesis, e.g., detachment from a solid phase, deprotection of a protecting group and purification of a desired product are carried out. It is desirable to obtain a nucleic acid having a purity 90% or more and preferably 95% or more by purification.

In the case of a double-stranded nucleic acid, the sense-strand nucleic acid and antisense-strand nucleic acid synthesized and purified are mixed in an appropriate ratio; for example, 0.1 to 10 equivalents, preferably 0.5 to 2 equivalents, more preferably 0.9 to 1.1 equivalents, and further preferably, 1 equivalent of the sense-strand nucleic acid is mixed with 1 equivalent of the antisense-strand nucleic acid. After mixing, the mixture is usually subjected to annealing; however, the annealing step may be skipped, and the mixture may be directly used.

The annealing may be carried out in any conditions as long as a double-stranded nucleic acid can be formed. The annealing is usually carried out by mixing an antisense-strand nucleic acid and a sense-strand nucleic acid in an almost equimolar ratio, heating the mixture at about 94° C. for about 5 minutes, and slowly cooled up to room temperature.

An example of the enzymatic transcription is a transcription method using phage RNA polymerase such as T7 and T3, or SP6RNA polymerase with a plasmid or DNA having a desired base sequence used as a template.

The nucleic acid of the present invention can be introduced into a cell by use of a transfection carrier, preferably, a cationic carrier such as a cationic liposome or directly introduced into a cell by use of a calcium phosphate method, an electroporation method or microinjection method.

The nucleic acid of the present invention may comprise a ligand. The nucleic acid of the present invention may be modified with one or more ligands or fluorophores at the 5' end and/or the 3' end, and/or within the sequence. The nucleic acid modified with a ligand or a fluorophore is also called as a conjugate nucleic acid. Modification can be made at the 5' end and/or the 3' end and/or within the sequence by allowing a reactive modifier to react on a solid phase during an elongation reaction on the solid phase. Alternatively, a nucleic acid having a functional group such as an amino group, a mercapto group, an azido group, or a triple bond introduced herein, is synthesized and purified in advance; and a modifier is allowed to react with the functional group.

In this manner, a conjugate nucleic acid can be obtained. As the ligand, a molecule having an affinity to a biomolecule may be used. Examples of the ligand include a lipid such as cholesterol, a fatty acid, tocopherol and retinoid; a sugar such as N-acetylgalactosamine (GalNAc), galactose (Gal) and mannose (Man); a full antibody; a fragment antibody such as scFV, Fab and VHH; a protein such as a low density lipoprotein (LDL) and human serum albumin; a peptide such as RGD, NGR, R9 and CPP; a low molecule such as folic acid; a synthetic polymer such as a synthetic polyamino acid; and a nucleic acid aptamer. These may be used in combination. Examples of the fluorophore include Cy3 series, Alexa (registered trademark) series, and black hole quencher (registered trademark). Examples of a method for adding a ligand to the nucleic acid of the present invention include, but are not limited to, a method of allowing a modifier, which is capable of reacting on a solid phase to react, during an elongation reaction on the solid phase to modify 5' end, 3' end and/or within the sequence. Alternatively, a nucleic acid having a functional group such as an amino group, a mercapto group, an azido group, or a triple bond introduced herein, is synthesized and purified in advance; and a modifier may be allowed to react with the functional group.

In place of the nucleic acid of the present invention, a vector which expresses the nucleic acid by introducing the vector into a cell may be used. More specifically, an expression vector is constructed by inserting the sequence encoding the nucleic acid of the present invention to downstream of the promoter within the expression vector and introduced into a cell to allow the nucleic acid to express. Examples of the expression vector include pcDNA6.
2-GW/miR (manufactured by Invitrogen), pSilencer 4.
1-CMV (manufactured by Ambion), pSINsi-hH1 DNA (manufactured by Takara Bio Inc.), pSINsi-hU6 DNA (manufactured by Takara Bio Inc.) and pENTR/U6 (manufactured by Invitrogen).

Since the nucleic acid of the present invention is expressed within a cell, using the vector is included in the technical scope of the nucleic acid of the present invention. A recombinant viral vector, which is produced by introducing the sequence encoding the nucleic acid of the present invention into a virus vector downstream the promoter and introducing the vector into a packaging cell, can be used. Examples of the virus vector include a retro virus vector, a lentiviral vector, an adenovirus vector and an adeno-associated virus vector.

2. Nucleic Acid Having an Activity to Suppress APCS Expression

In the present invention, an antisense-strand nucleic acid and a sense-strand nucleic acid can be designed based on the base sequence (SEQ ID NO: 1) of the APCS 2nd strand cDNA of a full-length mRNA of human APCS, which is registered, for example, in the Genbank, under Accession No. NM_001639.3. Note that, based on the comparison between the base sequence of cDNA of a full-length mRNA of human APCS and the base sequence of cDNA of a full-length mRNA of APCS of a non-human species, an antisense-strand nucleic acid and a sense-strand nucleic acid that suppresses expression of APCS mRNA in a non-human species can be designed.

An example of a nucleic acid having APCS expression-suppressing activity is a double-stranded nucleic acid consisting of an antisense-strand nucleic acid of the present invention comprising a complementary base sequence to the APCS mRNA sequence and a sense-strand nucleic acid of the present invention comprising a complementary base sequence to the base sequence of the antisense-strand nucleic acid, and having APCS expression-suppressing activity.

Expression of APCS can be suppressed by introducing the double-stranded nucleic acid of the present invention into a cell. For example, the double-stranded nucleic acid of the present invention is introduced into a cell in a concentration of several pM to several nM and then cultured for 24 hours or more. For example, at the time point of 48 hours after initiation of culture, expression of mRNA of APCS can be suppressed.

The activity to suppress APCS mRNA expression of the double-stranded nucleic acid of the present invention can be evaluated by transfecting e.g., a human cell strain with, e.g., the nucleic acid, by use of, e.g., a cationic liposome, culturing the human cell strain for a predetermined time and thereafter quantifying the expression level of APCS mRNA in the human cell strain.

The activity to suppress APCS mRNA expression of the double-stranded nucleic acid of the present invention can be evaluated by transfecting, e.g., a human cell strain with, e.g., the nucleic acid by use of, e.g., a cationic liposome and culturing for a predetermined time and thereafter quantifying the expression level of APCS mRNA in the human cell strain.

Examples of the nucleic acid having APCS expression-suppressing activity include, other than the above double-stranded nucleic acid, a single-stranded nucleic acid having a base sequence complementary to a part of the base sequence of the APCS mRNA, wherein the single-stranded nucleic acid suppresses expression of APCS. The single-stranded nucleic acid usually consists of 8 to 30 bases, preferably of 12 to 30 bases and more preferably 12 to 20 bases.

An example of the single-stranded nucleic acid is a single-stranded nucleic acid that is the antisense-strand nucleic acid of the double-stranded nucleic acid of the present invention.

Expression of APCS can be suppressed by introducing the antisense-strand nucleic acid of the present invention as a single-stranded nucleic acid into a cell. For example, the single-stranded nucleic acid of the present invention is introduced into a cell in a concentration of several pM to several μM and cultured for 24 hours or more. For example, at the time point of 48 hours after initiation of culture, expression of mRNA of APCS can be suppressed.

The activity to suppress APCS mRNA expression of the antisense-strand nucleic acid of the present invention can be evaluated by transfecting, e.g., a human cell strain with, e.g., the nucleic acid by use of, e.g., a cationic liposome, culturing the human cell strain for a predetermined time and thereafter quantifying the expression level of APCS mRNA in the human cell strain.

3. Pharmaceutical Composition of the Present Invention

The present invention also relates to a pharmaceutical composition comprising a nucleic acid such as a double-stranded nucleic acid and a single-stranded nucleic acid according to the present invention, as an active ingredient. The pharmaceutical composition of the present invention can be used as a therapeutic or prophylactic agent for amyloid-related diseases.

The present invention also provides a method for treating a disorder mediated by APCS-containing amyloid fibrils. In the method of treatment, the nucleic acid of the present invention or the pharmaceutical composition of the present invention is administered to a human in need of such a treatment to successfully treat a disorder mediated by APCS-containing amyloid fibrils.

An example of the disorder mediated by APCS-containing amyloid fibrils is an amyloid-related disease. The double-stranded nucleic acid of the present invention can be used alone in the treatment method; however, the nucleic acid is administered as an active ingredient of the pharmaceutical composition of the present invention to human to successfully produce a medicinal effect, as shown below.

The pharmaceutical composition of the present invention further comprises a carrier effective for allowing the nucleic acid of the present invention to migrate into a cell. Examples of the carrier effective for allowing the nucleic acid to migrate into a cell include a cationic carrier. Examples of the cationic carrier include a cationic liposome and a cationic polymer. As the carrier effective for allowing the nucleic acid to migrate into a cell, a carrier using a virus envelope may be used. Examples of the cationic polymer include JetSI (Qbiogene) and Jet-PEI (polyethyleneimine; Qbiogene). Examples of the carrier using a virus envelope include GenomeOne (HVJ-E liposome; manufactured by Ishihara Sangyo Kaisha, Ltd.).

A pharmaceutical composition comprising the nucleic acid of the present invention and a carrier as mentioned above can be prepared by a method known to those skilled in the art, for example, by mixing an appropriate concentration of a carrier dispersion with a nucleic acid solution. If a cationic carrier is used, since the nucleic acid is usually negatively charged in an aqueous solution, the carrier and the nucleic acid are mixed in an aqueous solution by a routine method to easily and successfully prepare the pharmaceutical composition of the present invention. Examples of the aqueous solvent to be used for preparing a pharmaceutical composition include an electrolyte solution such as water for injection, distilled water for injection and physiological saline; and a sugar solution such as a glucose solution and maltose solution. The conditions such as pH and temperature for preparing the pharmaceutical composition of the present invention can be appropriately selected by those skilled in the art. The pharmaceutical composition is, if necessary, subjected to a dispersion treatment using an ultrasonic disperser or a high pressure emulsifier etc. to obtain a homogeneous composition. Since the optimal method and conditions for preparing a pharmaceutical composition comprising the nucleic acid of the present invention and a carrier vary depending on the carrier to be used, those skilled in the art can select an optimal method depending on the carrier to be used regardless of the above method.

As the pharmaceutical composition of the present invention, for example, composite particles constituted of a nucleic acid and lead particles as components and a composition constituted of composite particles and, if desired, lipid membrane coating the composite particles, can be suitably used. Examples of the lead particles include a lipid assembly, liposomes, emulsion particles, high molecules, metal colloid and a fine particle preparation. Preferably, a liposome is used and more preferably a cationic liposome is used. In the present invention, lead particles may be constituted of a composite of two or more elements selected from, e.g., a lipid assembly, liposomes, emulsion particles, high molecules, metal colloid and a fine particle preparation or a composite constituted of, e.g., a lipid assembly, liposomes, emulsion particles, high molecules, metal colloid and/or a fine particle preparation or another compound (for example, sugar, lipid, and inorganic compound).

Examples of the lipid membrane coating the composite particles include membrane using, e.g., a non-cationic lipid, a lipid inhibiting agglomeration of particles, and a cationic lipid as a constitution component.

The pharmaceutical composition of the present invention can be prepared, for example, in accordance with the method described in International Publication No. WO2006/080118 etc.

With respect to the blending ratio of a nucleic acid and a carrier comprised in the pharmaceutical composition of the present invention, usually 1 to 200 parts by weight of the carrier relative to 1 part by mass of the nucleic acid is appropriate. The blending ratio is preferably 2.5 to 100 parts by mass of a carrier and more preferably 7 to 25 parts by mass of carrier relative to 1 part by mass of the nucleic acid.

The size of the particles constituting the pharmaceutical composition of the present invention in average is preferably about 10 nm to 300 nm, more preferably about 30 nm to 200 nm and further preferably about 50 nm to 150 nm.

The pharmaceutical composition of the present invention may comprise, other than the above carrier, e.g., a pharmaceutically acceptable carrier or a diluent. The pharmaceutically acceptable carrier or diluent is basically a chemically inactive and harmless compound (including a composition) and having no influence on the biological activity of the pharmaceutical composition of the present invention. Examples of the pharmaceutically acceptable carrier or diluent include, but are not particularly limited to, a salt solution, a sugar solution, a glycerol solution and ethanol.

The pharmaceutical composition of the present invention comprises a nucleic acid in an amount effective for treating or preventing a disease and is provided in a form appropriate for administering to patients. Examples of the dosage form of the pharmaceutical composition of the present invention may include a liquid such as an injection, an eye drop and an inhalation; and a topical preparation such as an ointment and a lotion.

In the case of a liquid, the concentration of the nucleic acid of the present invention serving as an active ingredient in the pharmaceutical composition of the present invention usually falls within the range of 0.001 to 25% (w/v), preferably 0.1 to 10% (w/v) and more preferably 0.5 to 5% (w/v). The pharmaceutical composition of the present invention may comprise any pharmaceutically acceptable additives such as an emulsifying aid, a stabilizer, a tonicity agent and/or a pH regulator in appropriate amounts. The pharmaceutically acceptable additives can be added in an appropriate step before and after dispersion of the composite.

The pH of the liquid is usually controlled within the range of about 5.0 to about 8.5 and preferably about 6.0 to about 8.0.

The liquid is preferably subjected to a sterilization treatment such as sterilization by filtration using, e.g., a membrane filter.

The pharmaceutical composition of the present invention can be prepared as a lyophilized preparation. The lyophilized preparation can be prepared by dispersing a nucleic acid and a carrier and lyophilizing the dispersion. The lyophilization can be carried out by a routine method. For example, a predetermined amount of a complex solution dispersed is dispensed in vials in aseptic conditions. The vials are subjected to a pre-drying process at about −40 to −20° C. for about 2 hours, a primary drying process at about 0 to 10° C. under reduced pressure and then a secondary drying process at about 15 to 25° C. under reduced pressure. In this manner, freeze drying can be carried out. Subsequently, the inner atmosphere of the vials is purged with nitrogen gas and a stopper is put on the vials. In this manner, the lyophilized preparation of the pharmaceutical composition of the present invention can be obtained.

The lyophilized preparation can be dissolved again by adding an appropriate solution and put in use. Examples of the solution include water for injection, an electrolyte solution such as and physiological saline; and a glucose solution and other general infusion. The volume of the solution to be used, which varies depending on, e.g., the application. Although it is not particularly limited, the volume is preferably 0.5 to 2 fold as large as the volume before freeze-drying, or 500 mL or less.

The pharmaceutical composition of the present invention can be dosed by intravenous administration, intraarterial administration, oral administration, intra-tissue administration, transdermal administration, transmucosal administration, or rectal administration; however, the composition is preferably dosed by a method appropriate for the symptom of the patient. Particularly intravenous administration, transdermal administration, and transmucosal administration are preferably used. Topical administration such as local administration within, e.g., cancer, can be made. Examples of the dosage form suitable for these administration methods include injections, oral preparations, intravenous fluids, absorbing agents, eye-drops, ointments, lotions and suppositories.

The dose of the pharmaceutical composition of the present invention is desirably determined in consideration of, e.g., the type of drug, dosage form, the state of the patient such as age and body weight; route of administration, and the nature and condition of the disease; however, the dose is usually 0.1 mg to 10 g/day per adult, preferably 1 mg to 500 mg/day per adult, in terms of mass of the nucleic acid. In some cases, the above dose or less is sufficient; on the contrary, the above dose or more is required in other cases. The pharmaceutical composition of the present invention can be administered once to several times at intervals of a single to several days.

EXAMPLES

Now, the present invention will be described by way of Examples; however, the present invention is not limited by these Examples.

Example 1: Synthesis of Double-Stranded Nucleic Acid

Synthesis of sense-strand nucleic acids consisting of the ribonucleotides set forth in SEQ ID NOS: 2 to 644 and antisense-strand nucleic acids consisting of the ribonucleotides set forth in SEQ ID NOS: 645 to 1287 were outsourced to Sigma Aldrich and double-stranded nucleic acids were prepared by annealing them (the sense-strand nucleic acids set forth in SEQ ID NO: n (n=2 to 644) and the antisense-strand nucleic acids set forth in SEQ ID NO: [n+643] are paired).

Example 2: Measurement of APCS mRNA Knockdown Activity

To 384-well culture plates, the double-stranded nucleic acids synthesized in Example 1 and a siRNA/RNAiMax mixture (20 µL) prepared by diluting RNAiMax transfection reagent (manufactured by Thermo Fisher Scientific, catalog number 13778150) with Opti-MEM I Reduced Serum Medium culture medium (manufactured by Thermo Fisher Scientific, catalog number 31985070) were added. A human ovarian cancer-derived cell strain, RMG-I cells (JCRB cell bank, JCRB0172) were seeded so as to be 10,000 cells/40 µL/well to each of the 384-well culture plates and incubated at 37° C. in 5% $CO_2$ condition for 24 hours. The culture medium used herein was Ham's F-12 Nutrient Mix culture medium (manufactured by Thermo Fisher Scientific, catalog number 11765-047) containing 10% fetal bovine serum (manufactured by Thermo Fisher Scientific, catalog number 10091-148). The final concentration of each of the double-stranded nucleic acids was set at 1 nM. Thereafter, the cells were washed with DPBS (no calcium, no magnesium) (manufactured by Thermo Fisher Scientific, catalog number 14190-144), and then, cDNA was synthesized from each of the plates by TaqMan (registered trademark) Fast Cells-to-CT (trademark) kit (manufactured by Thermo Fisher Scientific, catalog number 4399003) in accordance with the following method. A solution, which was prepared by mixing Lysis solution (contained in the kit) and DNase I (contained in the kit) in a ratio of 100:1, was added by 10 µL for each and the mixture was stirred for 5 minutes. Stop Solution (contained in the kit) was added by 1 µL for each. The mixture was stirred for 2 minutes to obtain an RNA extract. Then, 5 µL of 2×RT Buffer (contained in the kit), 0.5 µL of 20×RT Enzyme Mix (contained in the kit), 2.5 µL of Nuclease-free Water and 2 µL of the RNA extract were mixed. The mixture was allowed to react at 37° C. for 60 minutes and at 95° C. for 5 minutes to synthesize cDNA. The cDNA (2 µL) was added to MicroAmp (registered trademark) EnduraPlate (trademark) Optical 384-Well Clear Reaction Plates with Barcode (manufactured by Thermo Fisher Scientific, catalog number 4483285), and further 5 µL of TaqMan (registered trademark) Fast Universal PCR Master Mix (manufactured by Thermo Fisher Scientific, catalog number 4352042), 2.5 µL of DISTILLED WATER (ULTRAPURE) (manufactured by Thermo Fisher Scientific, catalog number 10977015), 0.25 µL of human APCS probe and 0.25 µL of human ACTB probe were added. Using QuantStudio (trademark) 7 Flex, human APCS gene and human ACTB (actin beta) gene were subjected to real time PCR. The expression level of ACTB as an expressible constituent gene was measured as the internal control and the APCS gene-expression level was corrected. Based on the APCS mRNA amount, which was obtained in the case where RMG-I cells were treated by a transfection reagent alone without using siRNA and specified as 1.0, the relative expression levels of APCS mRNAs of the cells to which individual siRNAs were introduced, were calculated. This experiment was repeated twice. The smallest relative expression levels of APCS mRNAs are shown in Table 1. For convenience sake, Table 1 will be separately shown as follows.

TABLE 1

| Double stranded nucleic acid No. | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|
| AH0001 | GCAUGAAUAUCAGACGCUAGG | SEQ ID NO: 2 | UAGCGUCUGAUAUUCAUGCCC | SEQ ID NO: 645 | GCAUGAAUAUCAGACGCUA | 0.305 |
| AH0002 | CAUGAAUAUCAGACGCUAGGG | SEQ ID NO: 3 | CUUAGCGUCUGAUAUUCAUGCC | SEQ ID NO: 646 | CAUGAAUAUCAGACGCUAG | 0.391 |
| AH0003 | AUAUCAGACGCUAGGGGACA | SEQ ID NO: 4 | UCCCCCUAGCGUCUGAUAUUC | SEQ ID NO: 647 | AUAUCAGACGCUAGGGGGA | 0.427 |
| AH0004 | CUAGGGGACAGCCACUGUGU | SEQ ID NO: 5 | ACAGUGGCUGUCCCCCUAGCG | SEQ ID NO: 648 | CUAGGGGACAGCCACUGU | 0.405 |
| AH0005 | AGGGGACAGCCACUGUGUUG | SEQ ID NO: 6 | ACCACAGUGGCUGUCCCCUAG | SEQ ID NO: 649 | AGGGGACAGCCACUGUGU | 0.401 |
| AH0006 | GGGGACAGCCACUGUGUUGUC | SEQ ID NO: 7 | CAACACAGUGGCUGUCCCCCU | SEQ ID NO: 650 | GGGGACAGCCACUGUGUUG | 0.456 |
| AH0007 | GGGACAGCCACUGUGUUGUCU | SEQ ID NO: 8 | ACAACACAGUGGCUGUCCCCC | SEQ ID NO: 651 | GGGACAGCCACUGUGUGU | 0.435 |
| AH0008 | GGACAGCCACUGUGUUGUCUG | SEQ ID NO: 9 | GACAACACAGUGGCUGUCCCC | SEQ ID NO: 652 | GGACAGCCACUGUGUUGUC | 0.436 |
| AH0009 | GACAGCCACUGUGUUGUCUGC | SEQ ID NO: 10 | AGACAACACAGUGGCUGUCCC | SEQ ID NO: 653 | GACAGCCACUGUGUUGUCU | 0.487 |
| AH0010 | GCCACUGUGUUGUCUGCUACC | SEQ ID NO: 11 | UAGCAGACAACACAGUGGCUG | SEQ ID NO: 654 | GCCACUGUGUUGUCUGCUA | 0.288 |
| AH0011 | CCACUGUGUUGUCUGCUACCC | SEQ ID NO: 12 | GUAGCAGACAACACAGUGGCU | SEQ ID NO: 655 | CCACUGUGUUGUCUGCUAC | 0.382 |
| AH0012 | CACUGUGUUGUCUGCUACCCU | SEQ ID NO: 13 | GGUAGCAGACAACACAGUGGC | SEQ ID NO: 656 | CACUGUGUUGUCUGCUACC | 0.490 |
| AH0013 | CUGUGUUGUCUGCUACCCUCA | SEQ ID NO: 14 | AGGGUAGCAGACAACACAGUG | SEQ ID NO: 657 | CUGUGUUGUCUGCUACCCU | 0.315 |
| AH0014 | UGUGUUGUCUGCUACCCUCAU | SEQ ID NO: 15 | GAGGGUAGCAGACAACACAGU | SEQ ID NO: 658 | UGUGUUGUCUGCUACCCUC | 0.360 |
| AH0015 | GUGUUGUCUGCUACCCUCAUC | SEQ ID NO: 16 | UGAGGGUAGCAGACAACACAG | SEQ ID NO: 659 | GUGUUGUCUGCUACCCUCA | 0.275 |
| AH0016 | UGUUGUCUGCUACCCUCAUCC | SEQ ID NO: 17 | AUGAGGGUAGCAGACAACACA | SEQ ID NO: 660 | UGUUGUCUGCUACCCUCAU | 0.259 |
| AH0017 | GUUGUCUGCUACCCUCAUCCU | SEQ ID NO: 18 | GAUGAGGGUAGCAGACAACAC | SEQ ID NO: 661 | GUUGUCUGCUACCCUCAUC | 0.345 |
| AH0018 | GUCUGCUACCCUCAUCCUGGU | SEQ ID NO: 19 | CAGGAUGAGGGUAGCAGACAA | SEQ ID NO: 662 | GUCUGCUACCCUCAUCCUG | 0.406 |
| AH0019 | CUGCUACCCUCAUCCUGGUCA | SEQ ID NO: 20 | ACCAGGAUGAGGGUAGCAGAC | SEQ ID NO: 663 | CUGCUACCCUCAUCCUGGU | 0.229 |
| AH0020 | GCUACCCUCAUCCUGGUCACU | SEQ ID NO: 21 | UGACCAGGAUGAGGGUAGCAG | SEQ ID NO: 664 | GCUACCCUCAUCCUGGUCA | 0.278 |
| AH0021 | CUACCCUCAUCCUGGUCACUG | SEQ ID NO: 22 | GUGACCAGGAUGAGGGUAGCA | SEQ ID NO: 665 | CUACCCUCAUCCUGGUCAC | 0.284 |
| AH0022 | UACCCUCAUCCUGGUCACUGC | SEQ ID NO: 23 | AGUGACCAGGAUGAGGGUAGC | SEQ ID NO: 666 | UACCCUCAUCCUGGUCACU | 0.234 |
| AH0023 | ACCCUCAUCCUGGUCACUGCU | SEQ ID NO: 24 | CAGUGACCAGGAUGAGGGUAG | SEQ ID NO: 667 | ACCCUCAUCCUGGUCACUG | 0.413 |

TABLE 1-continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0024 | SEQ ID NO: 25 | CCCUCAUCCUGGUCACUGCUU | SEQ ID NO: 668 | GCAGUGACCAGGAUGAGGGUA | SEQ ID NO: 1311 | CCCUCAUCCUGGUCACUGC | 0.268 |
| AH0025 | SEQ ID NO: 26 | CCUCAUCCUGGUCACUGCUUC | SEQ ID NO: 669 | AGCAGUGACCAGGAUGAGGGU | SEQ ID NO: 1312 | CCUCAUCCUGGUCACUGCU | 0.232 |
| AH0026 | SEQ ID NO: 27 | CUCAUCCUGGUCACUGCUUCU | SEQ ID NO: 670 | AAGCAGUGACCAGGAUGAGGG | SEQ ID NO: 1313 | CUCAUCCUGGUCACUGCUU | 0.293 |
| AH0027 | SEQ ID NO: 28 | CAUCCUGGUCACUGCUUCUC | SEQ ID NO: 671 | AGAAGCAGUGACCAGGAUGAG | SEQ ID NO: 1314 | CAUCCUGGUCACUGCUUCU | 0.158 |
| AH0028 | SEQ ID NO: 29 | AUCCUGGUCACUGCUUCUCU | SEQ ID NO: 672 | CAGAAGCAGUGACCAGGAUGA | SEQ ID NO: 1315 | AUCCUGGUCACUGCUUCUC | 0.286 |
| AH0029 | SEQ ID NO: 30 | UCCUGGUCACUGCUUCUCUA | SEQ ID NO: 673 | GCAGAAGCAGUGACCAGGAUG | SEQ ID NO: 1316 | UCCUGGUCACUGCUUCUCUG | 0.304 |
| AH0030 | SEQ ID NO: 31 | CCUGGUCACUGCUUCUCUAU | SEQ ID NO: 674 | AGCAGAAGCAGUGACCAGGA | SEQ ID NO: 1317 | CCUGGUCACUGCUUCUCUGCU | 0.083 |
| AH0031 | SEQ ID NO: 32 | CUGGUCACUGCUUCUCUAUA | SEQ ID NO: 675 | UAGCAGAAGCAGUGACCAGGA | SEQ ID NO: 1318 | CUGGUCACUGCUUCUCUGCUA | 0.132 |
| AH0032 | SEQ ID NO: 33 | UGGUCACUGCUUCUCUAUAA | SEQ ID NO: 676 | AUAGCAGAAGCAGUGACCAGG | SEQ ID NO: 1319 | UGGUCACUGCUUCUCUGCUAU | 0.172 |
| AH0033 | SEQ ID NO: 34 | GGUCACUGCUUCUCUAUAAC | SEQ ID NO: 677 | UAUAGCAGAAGCAGUGACCAG | SEQ ID NO: 1320 | GGUCACUGCUUCUCUGCUAUA | 0.117 |
| AH0034 | SEQ ID NO: 35 | GUCACUGCUUCUCUAUAACA | SEQ ID NO: 678 | UUAUAGCAGAAGCAGUGACCA | SEQ ID NO: 1321 | GUCACUGCUUCUCUGCUAUAA | 0.174 |
| AH0035 | SEQ ID NO: 36 | CACUGCUUCUCUAUAACAGC | SEQ ID NO: 679 | UGUUAUAGCAGAAGCAGUGAC | SEQ ID NO: 1322 | CACUGCUUCUCUGCUAUAACA | 0.082 |
| AH0036 | SEQ ID NO: 37 | ACUGCUUCUCUAUAACAGCC | SEQ ID NO: 680 | CUGUUAUAGCAGAAGCAGUGA | SEQ ID NO: 1323 | ACUGCUUCUCUGCUAUAACAG | 0.215 |
| AH0037 | SEQ ID NO: 38 | CUGCUUCUCUAUAACAGCCC | SEQ ID NO: 681 | GCUGUUAUAGCAGAAGCAGUG | SEQ ID NO: 1324 | CUGCUUCUCUGCUAUAACAGC | 0.082 |
| AH0038 | SEQ ID NO: 39 | GCUUCUCUAUAACAGCCCUA | SEQ ID NO: 682 | GGGCUGUUAUAGCAGAAGCAG | SEQ ID NO: 1325 | GCUUCUCUGCUAUAACAGCCC | 0.205 |
| AH0039 | SEQ ID NO: 40 | CUUCUCUAUAACAGCCCUAG | SEQ ID NO: 683 | AGGGCUGUUAUAGCAGAAGCA | SEQ ID NO: 1326 | CUUCUCUGCUAUAACAGCCCU | 0.165 |
| AH0040 | SEQ ID NO: 41 | UUCUCUAUAACAGCCCUAGG | SEQ ID NO: 684 | UAGGGCUGUUAUAGCAGAAGC | SEQ ID NO: 1327 | UUCUCUGCUAUAACAGCCCUA | 0.148 |
| AH0041 | SEQ ID NO: 42 | UCUCUAUAACAGCCCUAGGC | SEQ ID NO: 685 | CUAGGGCUGUUAUAGCAGAAG | SEQ ID NO: 1328 | UCUCUGCUAUAACAGCCCUAG | 0.371 |
| AH0042 | SEQ ID NO: 43 | CUCUAUAACAGCCCUAGGCC | SEQ ID NO: 686 | CCUAGGGCUGUUAUAGCAGAA | SEQ ID NO: 1329 | CUCUGCUAUAACAGCCCUAGG | 0.203 |
| AH0043 | SEQ ID NO: 44 | UCUAUAACAGCCCUAGGCCA | SEQ ID NO: 687 | GCCUAGGGCUGUUAUAGCAGA | SEQ ID NO: 1330 | UCUGCUAUAACAGCCCUAGGC | 0.419 |
| AH0044 | SEQ ID NO: 45 | CUAUAACAGCCCUAGGCCAG | SEQ ID NO: 688 | GGCCUAGGGCUGUUAUAGCAG | SEQ ID NO: 1331 | CUGCUAUAACAGCCCUAGGCC | 0.457 |
| AH0045 | SEQ ID NO: 46 | CUAUAACAGCCCUAGGCCAGG | SEQ ID NO: 689 | UGGCCUAGGGCUGUUUAUAGCA | SEQ ID NO: 1332 | CUAUAACAGCCCUAGGCCA | 0.115 |
| AH0046 | SEQ ID NO: 47 | UAUAACAGCCCUAGGCCAGGA | SEQ ID NO: 690 | CUGGCCUAGGGCUGUUUAUAG | SEQ ID NO: 1333 | UAUAACAGCCCUAGGCCAG | 0.300 |
| AH0047 | SEQ ID NO: 48 | AUAACAGCCCUAGGCCAGGAA | SEQ ID NO: 691 | CCUGGCCUAGGGCUGUUAUAG | SEQ ID NO: 1334 | AUAACAGCCCUAGGCCAGG | 0.396 |

TABLE 1-continued

| Double stranded nucleic acid No. | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|
| AH0048 | UAACAGCCCUAGGCCAGGAAU | SEQ ID NO: 49 | UCCUGGCCUAGGGCUGUUAUA | SEQ ID NO: 692 | UAACAGCCCUAGGCCAGGA | 0.479 |
| AH0049 | ACACAGCCCUAGGCCAGGAAUAU | SEQ ID NO: 50 | AUAUCCUGGCCUAGGGCUGUUA | SEQ ID NO: 693 | ACAGCCCUAGGCCAGGAAU | 0.283 |
| AH0050 | CAGCCCUAGGCCAGGAAUAUG | SEQ ID NO: 51 | UAUUCCUGGCCUAGGGCUGUU | SEQ ID NO: 694 | CAGCCCUAGGCCAGGAAUA | 0.293 |
| AH0051 | AGCCCUAGGCCAGGAAUAUGA | SEQ ID NO: 52 | AUAUUCCUGGCCUAGGGCUGU | SEQ ID NO: 695 | AGCCCUAGGCCAGGAAUAU | 0.220 |
| AH0052 | GCCCUAGGCCAGGAAUAUGAA | SEQ ID NO: 53 | CAUAUUCCUGGCCUAGGGCUG | SEQ ID NO: 696 | GCCCUAGGCCAGGAAUAUG | 0.189 |
| AH0053 | CCCUAGGCCAGGAAUAUGAAC | SEQ ID NO: 54 | UCAUAUUCCUGGCCUAGGGCU | SEQ ID NO: 697 | CCCUAGGCCAGGAAUAUGA | 0.158 |
| AH0054 | CCUAGGCCAGGAAUAUGAACA | SEQ ID NO: 55 | UUCAUAUUCCUGGCCUAGGGC | SEQ ID NO: 698 | CUAGGCCAGGAAUAUGAA | 0.188 |
| AH0055 | CUAGGCCAGGAAUAUGAACAA | SEQ ID NO: 56 | GUUCAUAUUCCUGGCCUAGGG | SEQ ID NO: 699 | CUAGGCCAGGAAUAUGAAC | 0.433 |
| AH0056 | UAGGCCAGGAAUAUGAACAAG | SEQ ID NO: 57 | UGUUCAUAUUCCUGGCCUAGG | SEQ ID NO: 700 | UAGGCCAGGAAUAUGAACA | 0.242 |
| AH0057 | AGGCCAGGAAUAUGAACAAGC | SEQ ID NO: 58 | UUGUUCAUAUUCCUGGCCUA | SEQ ID NO: 701 | AGGCCAGGAAUAUGAACAA | 0.107 |
| AH0058 | GGCCAGGAAUAUGAACAAGCC | SEQ ID NO: 59 | CUUGUUCAUAUUCCUGGCCUA | SEQ ID NO: 702 | GGCCAGGAAUAUGAACAAG | 0.428 |
| AH0059 | GCCAGGAAUAUGAACAAGCCG | SEQ ID NO: 60 | GCUUGUUCAUAUUCCUGGCC | SEQ ID NO: 703 | GCCAGGAAUAUGAACAAGC | 0.221 |
| AH0060 | CCAGGAAUAUGAACAAGCCGU | SEQ ID NO: 61 | GGCUUGUUCAUAUUCCUGGC | SEQ ID NO: 704 | CCAGGAAUAUGAACAAGCC | 0.242 |
| AH0061 | CAGGAAUAUGAACAAGCCGCU | SEQ ID NO: 62 | CGGCUUGUUCAUAUUCCUGGC | SEQ ID NO: 705 | CAGGAAUAUGAACAAGCCG | 0.299 |
| AH0062 | AGGAAUAUGAACAAGCCGCUG | SEQ ID NO: 63 | GCGCUUGUUCAUAUUCCUG | SEQ ID NO: 706 | AGGAAUAUGAACAAGCCGC | 0.309 |
| AH0063 | GGAAUAUGAACAAGCCGCUGC | SEQ ID NO: 64 | AGCGGCUUGUUCAUAUUCCU | SEQ ID NO: 707 | GGAAUAUGAACAAGCCGCU | 0.113 |
| AH0064 | GAAUAUGAACAAGCCGCUGCU | SEQ ID NO: 65 | CAGCGGCUUGUUCAUAUUCC | SEQ ID NO: 708 | GAAUAUGAACAAGCCGCUG | 0.103 |
| AH0065 | AAUAUGAACAAGCCGCUGCUU | SEQ ID NO: 66 | GCAGCGGCUUGUUCAUAUUCC | SEQ ID NO: 709 | AAUAUGAACAAGCCGCUGC | 0.444 |
| AH0066 | AUAUGAACAAGCCGCUGCUUU | SEQ ID NO: 67 | AGCAGCGGCUUGUUCAUAUUC | SEQ ID NO: 710 | AUAUGAACAAGCCGCUGCU | 0.198 |
| AH0067 | UAUGAACAAGCCGCUGCUUUG | SEQ ID NO: 68 | AAGCAGCGGCUUGUUCAUAUU | SEQ ID NO: 711 | UAUGAACAAGCCGCUGCUU | 0.464 |
| AH0068 | AUGAACAAGCCGCUGCUUUGG | SEQ ID NO: 69 | AAAGCAGCGGCUUGUUCAUAU | SEQ ID NO: 712 | AUGAACAAGCCGCUGCUUU | 0.190 |
| AH0069 | UGAACAAGCCGCUGCUUUGGA | SEQ ID NO: 70 | CAAAGCAGCGGCUUGUUCAUA | SEQ ID NO: 713 | UGAACAAGCCGCUGCUUUG | 0.150 |
| AH0070 | GAACAAGCCGCUGCUUUGGAU | SEQ ID NO: 71 | CCAAAGCAGCGGCUUGUUCAU | SEQ ID NO: 714 | GAACAAGCCGCUGCUUUGG | 0.149 |
| AH0071 | AACAAGCCGCUGCUUUGGAUC | SEQ ID NO: 72 | UCCAAAGCAGCGGCUUGUUCA | SEQ ID NO: 715 | AACAAGCCGCUGCUUUGGA | 0.180 |

TABLE 1 -continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0072 | SEQ ID NO: 73 | ACAAGCCGCUGCUUUGGAUCU | SEQ ID NO: 716 | AUCCAAAGCAGCCGGCUUGUUC | SEQ ID NO: 1359 | ACAAGCCGCUGCUUUGGAU | 0.078 |
| AH0073 | SEQ ID NO: 74 | CAAGCCGCUGCUUUGGAUCUC | SEQ ID NO: 717 | GAUCCAAAGCAGCGGCUUGUU | SEQ ID NO: 1360 | CAAGCCGCUGCUUUGGAUC | 0.100 |
| AH0074 | SEQ ID NO: 75 | AAGCCGCUGCUUUGGAUCUCU | SEQ ID NO: 718 | AGAUCCAAAGCAGCGGCUUGU | SEQ ID NO: 1361 | AAGCCGCUGCUUUGGAUCU | 0.127 |
| AH0075 | SEQ ID NO: 76 | AGCCGCUGCUUUGGAUCUCUG | SEQ ID NO: 719 | GAGAUCCAAAGCAGCGGCUUG | SEQ ID NO: 1362 | AGCCGCUGCUUUGGAUCUC | 0.123 |
| AH0076 | SEQ ID NO: 77 | GCCGCUGCUUUGGAUCUCUGU | SEQ ID NO: 720 | AGAGAUCCAAAGCAGCCGCUU | SEQ ID NO: 1363 | GCCGCUGCUUUGGAUCUCU | 0.047 |
| AH0077 | SEQ ID NO: 78 | CCGCUGCUUUGGAUCUCUGUC | SEQ ID NO: 721 | CAGAGAUCCAAAGCAGCCGCU | SEQ ID NO: 1364 | CCGCUGCUUUGGAUCUCUG | 0.054 |
| AH0078 | SEQ ID NO: 79 | CGCUGCUUUGGAUCUCUGUCC | SEQ ID NO: 722 | ACAGAGAUCCAAAGCAGCGCGG | SEQ ID NO: 1365 | CGCUGCUUUGGAUCUCUGU | 0.064 |
| AH0079 | SEQ ID NO: 80 | GCUGCUUUGGAUCUCUGUCCU | SEQ ID NO: 723 | GACAGAGAUCCAAAGCAGCG | SEQ ID NO: 1366 | GCUGCUUUGGAUCUCUGUC | 0.090 |
| AH0080 | SEQ ID NO: 81 | CUGCUUUGGAUCUCUGUCCUC | SEQ ID NO: 724 | GGACAGAGAUCCAAAGCAGC | SEQ ID NO: 1367 | CUGCUUUGGAUCUCUGUCC | 0.296 |
| AH0081 | SEQ ID NO: 82 | UGCUUUGGAUCUCUGUCCUCA | SEQ ID NO: 725 | AGGACAGAGAUCCAAAGCAG | SEQ ID NO: 1368 | UGCUUUGGAUCUCUGUCCU | 0.088 |
| AH0082 | SEQ ID NO: 83 | GCUUUGGAUCUCUGUCCUCAC | SEQ ID NO: 726 | GAGGACAGAGAUCCAAAGCA | SEQ ID NO: 1369 | GCUUUGGAUCUCUGUCCUC | 0.131 |
| AH0083 | SEQ ID NO: 84 | CUUUGGAUCUCUGUCCUCACC | SEQ ID NO: 727 | UGAGGACAGAGAUCCAAAGC | SEQ ID NO: 1370 | CUUUGGAUCUCUGUCCUCA | 0.070 |
| AH0084 | SEQ ID NO: 85 | UUUGGAUCUCUGUCCUCACCA | SEQ ID NO: 728 | GUGAGGACAGAGAUCCAAAG | SEQ ID NO: 1371 | UUUGGAUCUCUGUCCUCAC | 0.300 |
| AH0085 | SEQ ID NO: 86 | GGAUCUCUGUCCUCACCAGCC | SEQ ID NO: 729 | CUGGUGAGGACAGAGAUCCAA | SEQ ID NO: 1372 | GGAUCUCUGUCCUCACCAG | 0.129 |
| AH0086 | SEQ ID NO: 87 | GAUCUCUGUCCUCACCAGCCU | SEQ ID NO: 730 | GCUGGUGAGGACAGAGAUCCA | SEQ ID NO: 1373 | GAUCUCUGUCCUCACCAGC | 0.483 |
| AH0087 | SEQ ID NO: 88 | CUCUGUCCUCACCAGCCUCCU | SEQ ID NO: 731 | GAGGCUGGUGAGGACAGAGAU | SEQ ID NO: 1374 | CUCUGUCCUCACCAGCCUC | 0.263 |
| AH0088 | SEQ ID NO: 89 | CUGUCCUCACCAGCCUCCUGG | SEQ ID NO: 732 | AGGAGGCUGGUGAGGACAGAG | SEQ ID NO: 1375 | CUGUCCUCACCAGCCUCCU | 0.413 |
| AH0089 | SEQ ID NO: 90 | UGUCCUCACCAGCCUCCUGA | SEQ ID NO: 733 | CAGGAGGCUGGUGAGGACAGA | SEQ ID NO: 1376 | UGUCCUCACCAGCCUCCUG | 0.334 |
| AH0090 | SEQ ID NO: 91 | GUCCUCACCAGCCUCCUCCUGGAA | SEQ ID NO: 734 | CCAGGAGGCUGGUGAGGACA | SEQ ID NO: 1377 | GUCCUCACCAGCCUCCUGG | 0.295 |
| AH0091 | SEQ ID NO: 92 | UCCUCACCAGCCUCCUGGAAG | SEQ ID NO: 735 | UCCAGGAGGCUGGUGAGGACA | SEQ ID NO: 1378 | UCCUCACCAGCCUCCUGGA | 0.300 |
| AH0092 | SEQ ID NO: 93 | CUCACCAGCCUCCUGGAAGCC | SEQ ID NO: 736 | CUUCCAGGAGGCUGGUGAGGA | SEQ ID NO: 1379 | CUCACCAGCCUCCUGGAAG | 0.243 |
| AH0093 | SEQ ID NO: 94 | UCACCAGCCUCCUGGAAGCCU | SEQ ID NO: 737 | GCUUCCAGGAGGCUGGUGAGG | SEQ ID NO: 1380 | UCACCAGCCUCCUGGAAGC | 0.286 |
| AH0094 | SEQ ID NO: 95 | ACCAGCCUCCUGGAAGCCUU | SEQ ID NO: 738 | AGGCUUCCAGGAGGCUGGUGA | SEQ ID NO: 1381 | ACCAGCCUCCUGGAAGCCU | 0.365 |
| AH0095 | SEQ ID NO: 96 | CCAGCCUCCUGGAAGCCUUG | SEQ ID NO: 739 | AAGGCUUCCAGGAGGCUGGUG | SEQ ID NO: 1382 | CCAGCCUCCUGGAAGCCUU | 0.060 |

TABLE 1-continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0096 | SEQ ID NO: 97 | CAGCCUCCUGGAAGCCUUUGC | SEQ ID NO: 740 | AAAGGCUUCCAGGAGGCUGGU | SEQ ID NO: 1383 | CAGCCUCCUGGAAGCCUUUU | 0.066 |
| AH0097 | SEQ ID NO: 98 | AGCCUCCUGGAAGCCUUUGCU | SEQ ID NO: 741 | CAAAGGCUUCCAGGAGGCUGG | SEQ ID NO: 1384 | AGCCUCCUGGAAGCCUUUUG | 0.486 |
| AH0098 | SEQ ID NO: 99 | GCCUCCUGGAAGCCUUUGCUC | SEQ ID NO: 742 | GCAAAGGCUUCCAGGAGGCUG | SEQ ID NO: 1385 | GCCUCCUGGAAGCCUUUUGC | 0.374 |
| AH0099 | SEQ ID NO: 100 | CCUCCUGGAAGCCUUUGCUCA | SEQ ID NO: 743 | AGCAAAGGCUUCCAGGAGGCU | SEQ ID NO: 1386 | CCUCCUGGAAGCCUUUUGCU | 0.111 |
| AH0100 | SEQ ID NO: 101 | CUCCUGGAAGCCUUUGCUCAC | SEQ ID NO: 744 | GAGCAAAGGCUUCCAGGAGGC | SEQ ID NO: 1387 | CUCCUGGAAGCCUUUUGCUC | 0.310 |
| AH0101 | SEQ ID NO: 102 | UCCUGGAAGCCUUUGCUCACA | SEQ ID NO: 745 | UGAGCAAAGGCUUCCAGGAGG | SEQ ID NO: 1388 | UCCUGGAAGCCUUUUGCUCA | 0.053 |
| AH0102 | SEQ ID NO: 103 | CCUGGAAGCCUUUGCUCACAC | SEQ ID NO: 746 | GUGAGCAAAGGCUUCCAGGAG | SEQ ID NO: 1389 | CCUGGAAGCCUUUUGCUCAC | 0.086 |
| AH0103 | SEQ ID NO: 104 | CUGGAAGCCUUUGCUCACACA | SEQ ID NO: 747 | UGUGAGCAAAGGCUUCCAGGA | SEQ ID NO: 1390 | CUGGAAGCCUUUUGCUCACA | 0.121 |
| AH0104 | SEQ ID NO: 105 | GGAAGCCUUUGCUCACACAGA | SEQ ID NO: 748 | UCUGUGAGCAAAGGCUUCCAG | SEQ ID NO: 1391 | GGAAGCCUUUUGCUCACACA | 0.161 |
| AH0105 | SEQ ID NO: 106 | GAAGCCUUUGCUCACACAGAC | SEQ ID NO: 749 | GUCUGUGAGCAAAGGCUUCCA | SEQ ID NO: 1392 | GAAGCCUUUUGCUCACACAG | 0.291 |
| AH0106 | SEQ ID NO: 107 | AAGCCUUUGCUCACACAGACC | SEQ ID NO: 750 | GGUCUGUGAGCAAAGGCUUCC | SEQ ID NO: 1393 | AAGCCUUUUGCUCACACAGA | 0.065 |
| AH0107 | SEQ ID NO: 108 | AGCCUUUGCUCACACAGACCU | SEQ ID NO: 751 | AGGUCUGUGAGCAAAGGCUUC | SEQ ID NO: 1394 | AGCCUUUUGCUCACACAGAC | 0.136 |
| AH0108 | SEQ ID NO: 109 | GCCUUUGCUCACACAGACCUC | SEQ ID NO: 752 | GAGGUCUGUGAGCAAAGGCUU | SEQ ID NO: 1395 | GCCUUUUGCUCACACAGACC | 0.094 |
| AH0109 | SEQ ID NO: 110 | CCUUUGCUCACACAGACCUCA | SEQ ID NO: 753 | UGAGGUCUGUGAGCAAAGGCU | SEQ ID NO: 1396 | CCUUUGCUCACACAGACCU | 0.107 |
| AH0110 | SEQ ID NO: 111 | CUUUGCUCACACAGACCUCAG | SEQ ID NO: 754 | CUGAGGUCUGUGAGCAAAGGC | SEQ ID NO: 1397 | CUUUGCUCACACAGACCUC | 0.254 |
| AH0111 | SEQ ID NO: 112 | UUUGCUCACACAGACCUCAGU | SEQ ID NO: 755 | ACUGAGGUCUGUGAGCAAAGG | SEQ ID NO: 1398 | UUUGCUCACACAGACCUCA | 0.334 |
| AH0112 | SEQ ID NO: 113 | UGCUCACACAGACCUCAGUGG | SEQ ID NO: 756 | CCACUGAGGUCUGUGAGCAA | SEQ ID NO: 1399 | UGCUCACACAGACCUCAGU | 0.302 |
| AH0113 | SEQ ID NO: 114 | CUCACACAGACCUCAGUGGGA | SEQ ID NO: 757 | UCCCACUGAGGUCUGUGAGCA | SEQ ID NO: 1400 | CUCACACAGACCUCAGUGG | 0.490 |
| AH0114 | SEQ ID NO: 115 | CACACAGACCUCAGUGGGAAG | SEQ ID NO: 758 | CUUCCCACUGAGGUCUGUGAG | SEQ ID NO: 1401 | CACACAGACCUCAGUGGGA | 0.109 |
| AH0115 | SEQ ID NO: 116 | ACACAGACCUCAGUGGGAAGG | SEQ ID NO: 759 | CCUUCCCACUGAGGUCUGUGA | SEQ ID NO: 1402 | ACACAGACCUCAGUGGGAA | 0.105 |
| AH0116 | SEQ ID NO: 117 | CACAGACCUCAGUGGGAAGGA | SEQ ID NO: 760 | UCCUUCCCACUGAGGUCUGUG | SEQ ID NO: 1403 | CACAGACCUCAGUGGGAAG | 0.478 |
| AH0117 | SEQ ID NO: 118 | AGACCUCAGUGGGAAGGAAGG | SEQ ID NO: 761 | CCUUCCUUCCCACUGAGGUCU | SEQ ID NO: 1404 | AGACCUCAGUGGGAAGGUG | 0.157 |
| AH0118 | SEQ ID NO: 119 | GACCUCAGUGGGAAGGAAGGU | SEQ ID NO: 762 | ACCUUCCUUCCCACUGAGGUC | SEQ ID NO: 1405 | GACCUCAGUGGGAAGGUGU | 0.149 |
| AH0119 | SEQ ID NO: 120 | ACCUCAGUGGGAAGGAAGGUU | SEQ ID NO: 763 | AACACCUUCCUUCCCACUGAGGUCU | SEQ ID NO: 1406 | ACCUCAGUGGGAAGGUGUU | 0.123 |

TABLE 1-continued

| Double stranded nucleic acid No. | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|
| AH0120 | CCUCAGUGGGAAGGUGUUUGU | SEQ ID NO: 121 | AAACACCUUCCCACUGAGGUC | SEQ ID NO: 764 | CCUCAGUGGGAAGGUGUUU | 0.261 |
| AH0121 | CUCAGUGGGAAGGUGUUUGUA | SEQ ID NO: 122 | CAAACACCUUCCCACUGAGGU | SEQ ID NO: 765 | CUCAGUGGGAAGGUGUUUG | 0.316 |
| AH0122 | UCAGUGGGAAGGUGUUUGUAU | SEQ ID NO: 123 | ACAAACACCUUCCCACUGAGG | SEQ ID NO: 766 | UCAGUGGGAAGGUGUUUGU | 0.125 |
| AH0123 | CAGUGGGAAGGUGUUUGUAUU | SEQ ID NO: 124 | UACAAACACCUUCCCACUGAG | SEQ ID NO: 767 | CAGUGGGAAGGUGUUUGUA | 0.185 |
| AH0124 | AGUGGGAAGGUGUUUGUAUUU | SEQ ID NO: 125 | AUACAAACACCUUCCCACUGA | SEQ ID NO: 768 | AGUGGGAAGGUGUUUGUAU | 0.105 |
| AH0125 | GUGGGAAGGUGUUUGUAUUUC | SEQ ID NO: 126 | AAUACAAACACCUUCCCACUG | SEQ ID NO: 769 | GUGGGAAGGUGUUUGUAUU | 0.101 |
| AH0126 | UGGGAAGGUGUUUGUAUUUCC | SEQ ID NO: 127 | AAAUACAAACACCUUCCCACU | SEQ ID NO: 770 | UGGGAAGGUGUUUGUAUUU | 0.150 |
| AH0127 | GGGAAGGUGUUUGUAUUUCCU | SEQ ID NO: 128 | GAAAUACAAACACCUUCCCAC | SEQ ID NO: 771 | GGGAAGGUGUUUGUAUUUC | 0.386 |
| AH0128 | GGAAGGUGUUUGUAUUUCCUA | SEQ ID NO: 129 | GGAAAUACAAACACCUUCCCA | SEQ ID NO: 772 | GGAAGGUGUUUGUAUUUCC | 0.127 |
| AH0129 | GAAGGUGUUUGUAUUUCCUAG | SEQ ID NO: 130 | AGGAAAUACAAACACCUUCCC | SEQ ID NO: 773 | GAAGGUGUUUGUAUUUCCU | 0.077 |
| AH0130 | AAGGUGUUUGUAUUUCCUAGA | SEQ ID NO: 131 | UAGGAAAUACAAACACCUUCC | SEQ ID NO: 774 | AAGGUGUUUGUAUUUCCUA | 0.213 |
| AH0131 | AGGUGUUUGUAUUUCCUAGAG | SEQ ID NO: 132 | CUAGGAAAUACAAACACCUUC | SEQ ID NO: 775 | AGGUGUUUGUAUUUCCUAG | 0.084 |
| AH0132 | GGUGUUUGUAUUUCCUAGAGA | SEQ ID NO: 133 | UCUAGGAAAUACAAACACCUU | SEQ ID NO: 776 | GGUGUUUGUAUUUCCUAGA | 0.112 |
| AH0133 | GUGUUUGUAUUUCCUAGAGAA | SEQ ID NO: 134 | CUCUAGGAAAUACAAACACCU | SEQ ID NO: 777 | GUGUUUGUAUUUCCUAGAG | 0.153 |
| AH0134 | UGUUUGUAUUUCCUAGAGAAU | SEQ ID NO: 135 | UCUCUAGGAAAUACAAACACC | SEQ ID NO: 778 | UGUUUGUAUUUCCUAGAGA | 0.139 |
| AH0135 | GUUUGUAUUUCCUAGAGAAUC | SEQ ID NO: 136 | UUCUCUAGGAAAUACAAACAC | SEQ ID NO: 779 | GUUUGUAUUUCCUAGAGAA | 0.070 |
| AH0136 | UUUGUAUUUCCUAGAGAAUCU | SEQ ID NO: 137 | AUUCUCUAGGAAAUACAAACA | SEQ ID NO: 780 | UUUGUAUUUCCUAGAGAAU | 0.125 |
| AH0137 | UUGUAUUUCCUAGAGAAUCUG | SEQ ID NO: 138 | GAUUCUCUAGGAAAUACAAAC | SEQ ID NO: 781 | UUGUAUUUCCUAGAGAAUC | 0.451 |
| AH0138 | UGUAUUUCCUAGAGAAUCUGU | SEQ ID NO: 139 | AGAUUCUCUAGGAAAUACAAA | SEQ ID NO: 782 | UGUAUUUCCUAGAGAAUCU | 0.204 |
| AH0139 | GUAUUUCCUAGAGAAUCUGUU | SEQ ID NO: 140 | CAGAUUCUCUAGGAAAUACAA | SEQ ID NO: 783 | GUAUUUCCUAGAGAAUCUG | 0.071 |
| AH0140 | UAUUUCCUAGAGAAUCUGUUA | SEQ ID NO: 141 | ACAGAUUCUCUAGGAAAUACA | SEQ ID NO: 784 | UAUUUCCUAGAGAAUCUGU | 0.242 |
| AH0141 | AUUUCCUAGAGAAUCUGUUAC | SEQ ID NO: 142 | AACAGAUUCUCUAGGAAAUAC | SEQ ID NO: 785 | AUUUCCUAGAGAAUCUGUU | 0.123 |
| AH0142 | UUUCCUAGAGAAUCUGUUACU | SEQ ID NO: 143 | UAACAGAUUCUCUAGGAAAUA | SEQ ID NO: 786 | UUUCCUAGAGAAUCUGUUA | 0.179 |
| AH0143 | UUCCUAGAGAAUCUGUUACUA | SEQ ID NO: 144 | AGUAACAGAUUCUCUAGGAAA | SEQ ID NO: 787 | UCCUAGAGAAUCUGUUACU | 0.311 |

TABLE 1-continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0144 | SEQ ID NO: 145 | CCUAGAGAAUCUGUUACUGAU | SEQ ID NO: 788 | CAGUAACAGAUUCUCUAGGAA | SEQ ID NO: 1431 | CCUAGAGAAUCUGUUACUG | 0.137 |
| AH0145 | SEQ ID NO: 146 | CUAGAGAAUCUGUUACUGAUC | SEQ ID NO: 789 | UCAGUAACAGAUUCUCUAGGA | SEQ ID NO: 1432 | CUAGAGAAUCUGUUACUGA | 0.039 |
| AH0146 | SEQ ID NO: 147 | UAGAGAAUCUGUUACUGAUCA | SEQ ID NO: 790 | AUCAGUAACAGAUUCUCUAGG | SEQ ID NO: 1433 | UAGAGAAUCUGUUACUGAU | 0.051 |
| AH0147 | SEQ ID NO: 148 | AGAGAAUCUGUUACUGAUCAU | SEQ ID NO: 791 | GAUCAGUAACAGAUUCUCUAG | SEQ ID NO: 1434 | AGAGAAUCUGUUACUGAUC | 0.361 |
| AH0148 | SEQ ID NO: 149 | GAGAAUCUGUUACUGAUCAUG | SEQ ID NO: 792 | UGAUCAGUAACAGAUUCUCUA | SEQ ID NO: 1435 | GAGAAUCUGUUACUGAUCA | 0.090 |
| AH0149 | SEQ ID NO: 150 | AGAAUCUGUUACUGAUCAUGU | SEQ ID NO: 793 | AUGAUCAGUAACAGAUUCUCU | SEQ ID NO: 1436 | AGAAUCUGUUACUGAUCAU | 0.211 |
| AH0150 | SEQ ID NO: 151 | GAAUCUGUUACUGAUCAUGUA | SEQ ID NO: 794 | CAUGAUCAGUAACAGAUUCUC | SEQ ID NO: 1437 | GAAUCUGUUACUGAUCAUG | 0.183 |
| AH0151 | SEQ ID NO: 152 | AAUCUGUUACUGAUCAUGUAA | SEQ ID NO: 795 | ACAUGAUCAGUAACAGAUUCU | SEQ ID NO: 1438 | AAUCUGUUACUGAUCAUGU | 0.477 |
| AH0152 | SEQ ID NO: 153 | AUCUGUUACUGAUCAUGUAAA | SEQ ID NO: 796 | UACAUGAUCAGUAACAGAUUC | SEQ ID NO: 1439 | AUCUGUUACUGAUCAUGUA | 0.103 |
| AH0153 | SEQ ID NO: 154 | UCUGUUACUGAUCAUGUAAAC | SEQ ID NO: 797 | UUACAUGAUCAGUAACAGAUU | SEQ ID NO: 1440 | UCUGUUACUGAUCAUGUAA | 0.166 |
| AH0154 | SEQ ID NO: 155 | CUGUUACUGAUCAUGUAAACU | SEQ ID NO: 798 | UUUACAUGAUCAGUAACAGA | SEQ ID NO: 1441 | CUGUUACUGAUCAUGUAAA | 0.155 |
| AH0155 | SEQ ID NO: 156 | UGUUACUGAUCAUGUAAACUG | SEQ ID NO: 799 | GUUUACAUGAUCAGUAACAGA | SEQ ID NO: 1442 | UGUUACUGAUCAUGUAAAC | 0.260 |
| AH0156 | SEQ ID NO: 157 | GUUACUGAUCAUGUAAACUUG | SEQ ID NO: 800 | AGUUUACAUGAUCAGUAACAG | SEQ ID NO: 1443 | GUUACUGAUCAUGUAAACU | 0.213 |
| AH0157 | SEQ ID NO: 158 | UUACUGAUCAUGUAAACUUGA | SEQ ID NO: 801 | UCAAGUUUACAUGAUCAGUAA | SEQ ID NO: 1444 | UUACUGAUCAUGUAAACUUG | 0.365 |
| AH0158 | SEQ ID NO: 159 | UACUGAUCAUGUAAACUUGAU | SEQ ID NO: 802 | AUCAAGUUUACAUGAUCAGUA | SEQ ID NO: 1445 | UACUGAUCAUGUAAACUUGA | 0.167 |
| AH0159 | SEQ ID NO: 160 | ACUGAUCAUGUAAACUUGAUC | SEQ ID NO: 803 | GAUCAAGUUUACAUGAUCAGU | SEQ ID NO: 1446 | ACUGAUCAUGUAAACUUGAU | 0.457 |
| AH0160 | SEQ ID NO: 161 | CUGAUCAUGUAAACUUGAUCA | SEQ ID NO: 804 | UGAUCAAGUUUACAUGAUCAG | SEQ ID NO: 1447 | CUGAUCAUGUAAACUUGAUC | 0.338 |
| AH0161 | SEQ ID NO: 162 | UGAUCAUGUAAACUUGAUCAC | SEQ ID NO: 805 | UGUGAUCAAGUUUACAUGAUC | SEQ ID NO: 1448 | UGAUCAUGUAAACUUGAUCA | 0.286 |
| AH0162 | SEQ ID NO: 163 | GAUCAUGUAAACUUGAUCACC | SEQ ID NO: 806 | GUGUGAUCAAGUUUACAUGAU | SEQ ID NO: 1449 | GAUCAUGUAAACUUGAUCAC | 0.485 |
| AH0163 | SEQ ID NO: 164 | AUCAUGUAAACUUGAUCACCG | SEQ ID NO: 807 | AGCGGUGAUCAAGUUUACAUGA | SEQ ID NO: 1450 | AUCAUGUAAACUUGAUCACC | 0.355 |
| AH0164 | SEQ ID NO: 165 | UCAUGUAAACUUGAUCACCGCU | SEQ ID NO: 808 | UGAUCAAGUUUACAUGAUCAGU | SEQ ID NO: 1451 | UCAUGUAAACUUGAUCACCGCU | 0.360 |
| AH0165 | SEQ ID NO: 166 | CAUGUAAACUUGAUCACCGCGA | SEQ ID NO: 809 | CAGCGGUGAUCAAGUUUACAUGA | SEQ ID NO: 1452 | CAUGUAAACUUGAUCACCGCUG | 0.212 |
| AH0166 | SEQ ID NO: 167 | AUGUAAACUUGAUCACCGCGUGGA | SEQ ID NO: 810 | UCCAGCGGUGAUCAAGUUUACAUGA | SEQ ID NO: 1453 | AUGUAAACUUGAUCACCGCUGGA | 0.493 |
| AH0167 | SEQ ID NO: 168 | UGAUCACCGCGUGGAGAGCU | SEQ ID NO: 811 | UUCUCCAGCGGUGAUCAAGU | SEQ ID NO: 1454 | UGAUCACCGCGUGGAGAA | 0.078 |

TABLE 1-continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0168 | SEQ ID NO: 169 | GAUCACACCGCUGGAGAAGCC | SEQ ID NO: 812 | CUUCUCCAGCGGUGUGAUCAA | SEQ ID NO: 1455 | GAUCACACCGCUGGAGAAG | 0.465 |
| AH0169 | SEQ ID NO: 170 | CACACCGCUGGAGAAGCCUCU | SEQ ID NO: 813 | AGGGCUUCUCCAGCGGUGUGAU | SEQ ID NO: 1456 | CACACCGCUGGAGAAGCCU | 0.312 |
| AH0170 | SEQ ID NO: 171 | ACACCGCUGGAGAAGCCUCUA | SEQ ID NO: 814 | GAGGCUUCUCCAGCGGUGUGA | SEQ ID NO: 1457 | ACACCGCUGGAGAAGCCUC | 0.208 |
| AH0171 | SEQ ID NO: 172 | CACCGCUGGAGAAGCCUCUAC | SEQ ID NO: 815 | AGAGGCUUCUCCAGCGGUGUG | SEQ ID NO: 1458 | CACCGCUGGAGAAGCCUCU | 0.190 |
| AH0172 | SEQ ID NO: 173 | ACCGCUGGAGAAGCCUCUACA | SEQ ID NO: 816 | UAGAGGCUUCUCCAGCGGUGU | SEQ ID NO: 1459 | ACCGCUGGAGAAGCCUCUA | 0.276 |
| AH0173 | SEQ ID NO: 174 | CCGCUGGAGAAGCCUCUACAG | SEQ ID NO: 817 | GUAGAGGCUUCUCCAGCGGUG | SEQ ID NO: 1460 | CCGCUGGAGAAGCCUCUAC | 0.397 |
| AH0174 | SEQ ID NO: 175 | CGCUGGAGAAGCCUCUACAGA | SEQ ID NO: 818 | UGUAGAGGCUUCUCCAGCGGU | SEQ ID NO: 1461 | CGCUGGAGAAGCCUCUACA | 0.056 |
| AH0175 | SEQ ID NO: 176 | GCUGGAGAAGCCUCUACAGAA | SEQ ID NO: 819 | CUGUAGAGGCUUCUCCAGCGG | SEQ ID NO: 1462 | GCUGGAGAAGCCUCUACAG | 0.335 |
| AH0176 | SEQ ID NO: 177 | CUGGAGAAGCCUCUACAGAAC | SEQ ID NO: 820 | UCUGUAGAGGCUUCUCCAGCG | SEQ ID NO: 1463 | CUGGAGAAGCCUCUACAGA | 0.080 |
| AH0177 | SEQ ID NO: 178 | UGGAGAAGCCUCUACAGAACU | SEQ ID NO: 821 | UUCUGUAGAGGCUUCUCCAGC | SEQ ID NO: 1464 | UGGAGAAGCCUCUACAGAA | 0.088 |
| AH0178 | SEQ ID NO: 179 | GGAGAAGCCUCUACAGAACUU | SEQ ID NO: 822 | GUUCUGUAGAGGCUUCUCCAG | SEQ ID NO: 1465 | GGAGAAGCCUCUACAGAAC | 0.142 |
| AH0179 | SEQ ID NO: 180 | GAGAAGCCUCUACAGAACUUA | SEQ ID NO: 823 | AGUUCUGUAGAGGCUUCUCCA | SEQ ID NO: 1466 | GAGAAGCCUCUACAGAACU | 0.276 |
| AH0180 | SEQ ID NO: 181 | AGAAGCCUCUACAGAACUUUA | SEQ ID NO: 824 | AAGUUCUGUAGAGGCUUCUCC | SEQ ID NO: 1467 | AGAAGCCUCUACAGAACUU | 0.160 |
| AH0181 | SEQ ID NO: 182 | GAAGCCUCUACAGAACUUUAC | SEQ ID NO: 825 | AAAGUUCUGUAGAGGCUUCUC | SEQ ID NO: 1468 | GAAGCCUCUACAGAACUUU | 0.156 |
| AH0182 | SEQ ID NO: 183 | AAGCCUCUACAGAACUUUACC | SEQ ID NO: 826 | UAAAGUUCUGUAGAGGCUUCU | SEQ ID NO: 1469 | AAGCCUCUACAGAACUUUA | 0.210 |
| AH0183 | SEQ ID NO: 184 | AGCCUCUACAGAACUUUACCU | SEQ ID NO: 827 | GUAAAGUUCUGUAGAGGCUUC | SEQ ID NO: 1470 | AGCCUCUACAGAACUUUAC | 0.305 |
| AH0184 | SEQ ID NO: 185 | GCCUCUACAGAACUUUACCUU | SEQ ID NO: 828 | GGUAAAGUUCUGUAGAGGCUU | SEQ ID NO: 1471 | GCCUCUACAGAACUUUACC | 0.343 |
| AH0185 | SEQ ID NO: 186 | CCUCUACAGAACUUUACCUUG | SEQ ID NO: 829 | AGGUAAAGUUCUGUAGAGGCU | SEQ ID NO: 1472 | CCUCUACAGAACUUUACCU | 0.178 |
| AH0186 | SEQ ID NO: 187 | CUCUACAGAACUUUACCUUGU | SEQ ID NO: 830 | AAGGUAAAGUUCUGUAGAGGC | SEQ ID NO: 1473 | CUCUACAGAACUUUACCUU | 0.183 |
| AH0187 | SEQ ID NO: 188 | UCUACAGAACUUUACCUUGUG | SEQ ID NO: 831 | CAAGGUAAAGUUCUGUAGAGG | SEQ ID NO: 1474 | UCUACAGAACUUUACCUUG | 0.244 |
| AH0188 | SEQ ID NO: 189 | CUACAGAACUUUACCUUGUGU | SEQ ID NO: 832 | ACAAGGUAAAGUUCUGUAGAG | SEQ ID NO: 1475 | CUACAGAACUUUACCUUGU | 0.079 |
| AH0189 | SEQ ID NO: 190 | UACAGAACUUUACCUUGUGUG | SEQ ID NO: 833 | CACAAGGUAAAGUUCUGUAGA | SEQ ID NO: 1476 | UACAGAACUUUACCUUGUG | 0.219 |
| AH0190 | SEQ ID NO: 191 | ACAGAACUUUACCUUGUGUGU | SEQ ID NO: 834 | ACACAAGGUAAAGUUCUGUAG | SEQ ID NO: 1477 | ACAGAACUUUACCUUGUGU | 0.387 |
| AH0191 | SEQ ID NO: 192 | CAGAACUUUACCUUGUGUGUU | SEQ ID NO: 835 | AACACAAGGUAAAGUUCUGUA | SEQ ID NO: 1478 | CAGAACUUUACCUUGUGUU | 0.171 |

TABLE 1-continued

| Double stranded nucleic acid No. | Sense strand sequence (5'--->3') | SEQ ID NO: | Antisense strand sequence (5'--->3') | SEQ ID NO: | Target APCS mRNA sequence | SEQ ID NO: | APCS relative expression level |
|---|---|---|---|---|---|---|---|
| AH0192 | AGAACUUUACCUUGUGUUUC | 193 | AAACACAAGGUAAAGUUCUGU | 836 | AGAACUUUACCUUGUGUUU | 1479 | 0.133 |
| AH0193 | GAACUUUACCUUGUGUUUCG | 194 | AAAACACAAGGUAAAGUUCUG | 837 | GAACUUUACCUUGUGUUUU | 1480 | 0.081 |
| AH0194 | AACUUUACCUUGUGUUUUCC | 195 | GAAAACACAAGGUAAAGUUCU | 838 | AACUUUACCUUGUGUUUUC | 1481 | 0.347 |
| AH0195 | CUUUACCUUGUGUUUUCGAGC | 196 | UCGAAAACACAAGGUAAAGUU | 839 | CUUUACCUUGUGUUUUCGA | 1482 | 0.453 |
| AH0196 | ACCUUGUGUUUUCGAGCCUAU | 197 | AGGCUCGAAAACACAAGGUAA | 840 | ACCUUGUGUUUUCGAGCCU | 1483 | 0.164 |
| AH0197 | CCUUGUGUUUUCGAGCCUAUA | 198 | UAGGCUCGAAAACACAAGGUA | 841 | CCUUGUGUUUUCGAGCCUA | 1484 | 0.081 |
| AH0198 | CUUGUGUUUUCGAGCCUAUAG | 199 | AUAGGCUCGAAAACACAAGGU | 842 | CUUGUGUUUUCGAGCCUAU | 1485 | 0.110 |
| AH0199 | UUGUGUUUUCGAGCCUAUAGU | 200 | UAUAGGCUCGAAAACACAAGG | 843 | UUGUGUUUUCGAGCCUAUA | 1486 | 0.137 |
| AH0200 | GUGUGUUUUCGAGCCUAUAGUGA | 201 | ACUAUAGGCUCGAAAACACAA | 844 | GUGUGUUUUCGAGCCUAUAGU | 1487 | 0.125 |
| AH0201 | GUUUUCGAGCCUAUAGUGAUC | 202 | UCACUAUAGGCUCGAAAACAC | 845 | GUUUUCGAGCCUAUAGUGA | 1488 | 0.074 |
| AH0202 | UUUUCGAGCCUAUAGUGAUCU | 203 | AUCACUAUAGGCUCGAAAACA | 846 | UUUUCGAGCCUAUAGUGAU | 1489 | 0.136 |
| AH0203 | CGAGCCUAUAGUGAUCUCUCU | 204 | AGAGAUCACUAUAGGCUCGAA | 847 | CGAGCCUAUAGUGAUCUCU | 1490 | 0.119 |
| AH0204 | GAGCCUAUAGUGAUCUCUCUC | 205 | GAGAGAUCACUAUAGGCUCGA | 848 | GAGCCUAUAGUGAUCUCUC | 1491 | 0.127 |
| AH0205 | AGCCUAUAGUGAUCUCUCUCG | 206 | AGAGAGAUCACUAUAGGCUCG | 849 | AGCCUAUAGUGAUCUCUCU | 1492 | 0.091 |
| AH0206 | CCUAUAGUGAUCUCUCUCGUG | 207 | GAGAGAGAUCACUAUAGGCUC | 850 | GCCUAUAGUGAUCUCUCUC | 1493 | 0.090 |
| AH0207 | CUAUAGUGAUCUCUCUCGUGG | 208 | CGAGAGAGAUCACUAUAGGCU | 851 | CCUAUAGUGAUCUCUCUCG | 1494 | 0.287 |
| AH0208 | UAUAGUGAUCUCUCUCGUGGC | 209 | ACGAGAGAGAUCACUAUAGGC | 852 | CUAUAGUGAUCUCUCUCGU | 1495 | 0.088 |
| AH0209 | AGUGAUCUCUCUCGUGGCC | 210 | CACGAGAGAGAUCACUAUAGG | 853 | UAUAGUGAUCUCUCUCGUG | 1496 | 0.355 |
| AH0210 | AGUGAUCUCUCUCGUGGCCUAC | 211 | AGGCCACGAGAGAGAUCACUAU | 854 | AGUGAUCUCUCUCGUGCCU | 1497 | 0.089 |
| AH0211 | GUGAUCUCUCUCGUGCCUACA | 212 | UAGGCCACGAGAGAGAUCACUA | 855 | GUGAUCUCUCUCGUGCCUA | 1498 | 0.072 |
| AH0212 | UGAUCUCUCUCGUGCCUACAG | 213 | GUAGGCCACGAGAGAGAUCACU | 856 | UGAUCUCUCUCGUGCCUAC | 1499 | 0.158 |
| AH0213 | GAUCUCUCUCGUGCCUACAGC | 214 | UGUAGGCCACGAGAGAGAUCAC | 857 | GAUCUCUCUCGUGCCUACA | 1500 | 0.126 |
| AH0214 | CUCUCUCGUGCCUACAGCCUCU | 215 | GAGGCUGUAGGCACGAGAGAG | 858 | CUCUCUCGUGCCUACAGCC | 1501 | 0.196 |
| AH0215 | UCUCGUGCCUACAGCCUCUUC | 216 | AGAGGCUGUAGGCACGAGAGA | 859 | UCUCGUGCCUACAGCCUCU | 1502 | 0.140 |

TABLE 1-continued

| Double stranded nucleic acid No. | Sense strand sequence (5'--->3') | SEQ ID NO: | Antisense strand sequence (5'--->3') | SEQ ID NO: | Target APCS mRNA sequence | SEQ ID NO: | APCS relative expression level |
|---|---|---|---|---|---|---|---|
| AH0216 | CUCGUGCCUACAGCCUCUCU | SEQ ID NO: 217 | AAGAGGCUGUAGGCACGAGAG | SEQ ID NO: 860 | CUCGUGCCUACAGCCCUCUU | SEQ ID NO: 1503 | 0.198 |
| AH0217 | CGUGCCUACAGCCUCUUCCC | SEQ ID NO: 218 | AGAAGAGGCUGUAGGCACGAG | SEQ ID NO: 861 | CGUGCCUACAGCCUCUUCUCU | SEQ ID NO: 1504 | 0.181 |
| AH0218 | GUGCCUACAGCCUCUUCUCCU | SEQ ID NO: 219 | GAGAAGAGGCUGUAGGCACGA | SEQ ID NO: 862 | GUGCCUACAGCCUCUUCUCUC | SEQ ID NO: 1505 | 0.101 |
| AH0219 | GCCUACAGCCUCUUCUCCUAC | SEQ ID NO: 220 | AGGAGAAGAGGCUGUAGGCAC | SEQ ID NO: 863 | GCCUACAGCCUCUUCUCUCCU | SEQ ID NO: 1506 | 0.100 |
| AH0220 | CCUACAGCCUCUUCUCCUACA | SEQ ID NO: 221 | UAGGAGAAGAGGCUGUAGGCA | SEQ ID NO: 864 | CCUACAGCCUCUUCUCUCCUA | SEQ ID NO: 1507 | 0.086 |
| AH0221 | CUACAGCCUCUUCUCCUACAA | SEQ ID NO: 222 | GUAGGAGAAGAGGCUGUAGGC | SEQ ID NO: 865 | CUACAGCCUCUUCUCUCCUAC | SEQ ID NO: 1508 | 0.153 |
| AH0222 | UACAGCCUCUUCUCCUACAAU | SEQ ID NO: 223 | UGUAGGAGAAGAGGCUGUAGG | SEQ ID NO: 866 | UACAGCCUCUUCUCCUACA | SEQ ID NO: 1509 | 0.221 |
| AH0223 | ACAGCCUCUUCUCCUACAAUA | SEQ ID NO: 224 | UUGUAGGAGAAGAGGCUGUAG | SEQ ID NO: 867 | ACAGCCCUCUUCUCCUACAA | SEQ ID NO: 1510 | 0.137 |
| AH0224 | CAGCCUCUUCUCCUACAAUAC | SEQ ID NO: 225 | AUUGUAGGAGAAGAGGCUGUA | SEQ ID NO: 868 | CAGCCUCUUCUCCUACAAU | SEQ ID NO: 1511 | 0.184 |
| AH0225 | AGCCUCUUCUCCUACAAUACC | SEQ ID NO: 226 | UAUUGUAGGAGAAGAGGCUGU | SEQ ID NO: 869 | AGCCUCUUCUCCUACAAUA | SEQ ID NO: 1512 | 0.036 |
| AH0226 | GCCUCUUCUCCUACAAUACCC | SEQ ID NO: 227 | GUAUUGUAGGAGAAGAGGCUG | SEQ ID NO: 870 | GCCUCUUCUCCUACAAUAC | SEQ ID NO: 1513 | 0.172 |
| AH0227 | CCUCUUCUCCUACAAUACCCA | SEQ ID NO: 228 | GGUAUUGUAGGAGAAGAGGCU | SEQ ID NO: 871 | CCUUCUUCUCCUACAAUACC | SEQ ID NO: 1514 | 0.116 |
| AH0228 | UCUUCUCCUACAAUACCCAAG | SEQ ID NO: 229 | UGGGUAUUGUAGGAGAAGAGG | SEQ ID NO: 872 | UCUUCUCCUACAAUACCCA | SEQ ID NO: 1515 | 0.450 |
| AH0229 | UCUCCUACAAUACCCAAGGCA | SEQ ID NO: 230 | CCUUGGGUAUUGUAGGAGAAG | SEQ ID NO: 873 | UCUCCUACAAUACCCAAGG | SEQ ID NO: 1516 | 0.486 |
| AH0230 | CUCCUACAAUACCCAAGGCAG | SEQ ID NO: 231 | GCCUUGGGUAUUGUAGGAGAA | SEQ ID NO: 874 | CUCCUACAAUACCCAAGGC | SEQ ID NO: 1517 | 0.303 |
| AH0231 | UCCUACAAUACCCAAGGCAGG | SEQ ID NO: 232 | UGCCUUGGGUAUUGUAGGAGA | SEQ ID NO: 875 | UCCUACAAUACCCAAGGCA | SEQ ID NO: 1518 | 0.206 |
| AH0232 | CCUACAAUACCCAAGGCAGGG | SEQ ID NO: 233 | CUGCCUUGGGUAUUGUAGGAG | SEQ ID NO: 876 | CCUACAAUACCCAAGGCAG | SEQ ID NO: 1519 | 0.324 |
| AH0233 | CUACAAUACCCAAGGCAGGGA | SEQ ID NO: 234 | CCUGCCUUGGGUAUUGUAGGA | SEQ ID NO: 877 | CUACAAUACCCAAGGCAGG | SEQ ID NO: 1520 | 0.223 |
| AH0234 | CAAUACCCAAGGCAGGGAUAU | SEQ ID NO: 235 | AUCCCUGCCUUGGGUAUUGUA | SEQ ID NO: 878 | CAAUACCCAAGGCAGGGAU | SEQ ID NO: 1521 | 0.323 |
| AH0235 | AUACCCAAGGCAGGGAUAUAUG | SEQ ID NO: 236 | UUAUCCCUGCCUUGGGUAUUG | SEQ ID NO: 879 | AUACCCAAGGCAGGGAUAA | SEQ ID NO: 1522 | 0.207 |
| AH0236 | UACCCAAGGCAGGGAUAUAUGA | SEQ ID NO: 237 | AUUAUCCCUGCCUUGGGUAUU | SEQ ID NO: 880 | UACCCAAGGCAGGGAUAUAU | SEQ ID NO: 1523 | 0.450 |
| AH0237 | CCAAGGCAGGGAUAUAUGAGCU | SEQ ID NO: 238 | CUCAUAUAUCCCUGCCUUGGGU | SEQ ID NO: 881 | CCAAGGCAGGGAUAAUGAG | SEQ ID NO: 1524 | 0.424 |
| AH0238 | AAGGCAGGGAUAUAUGAGCUAC | SEQ ID NO: 239 | AGCUCAUAUAUCCCUGCCUUGG | SEQ ID NO: 882 | AAGGCAGGGAUAUAAUGAGCU | SEQ ID NO: 1525 | 0.172 |
| AH0239 | AGGCAGGGAUAUAUGAGCUACU | SEQ ID NO: 240 | UAGCUCAUAUAUCCCUGCCUUG | SEQ ID NO: 883 | AGGCAGGGAUAUAUGAGCUA | SEQ ID NO: 1526 | 0.396 |

TABLE 1-continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0240 | SEQ ID NO: 241 | GCAGGGAUAAUGAGCUACUAG | SEQ ID NO: 884 | AGUAGCUCAUUAUCCCUGCCU | SEQ ID NO: 1527 | GCAGGGAUAAUGAGCUACU | 0.280 |
| AH0241 | SEQ ID NO: 242 | CAGGGAUAAUGAGCUACUAGU | SEQ ID NO: 885 | UAGUAGCUCAUUAUCCCUGCC | SEQ ID NO: 1528 | CAGGGAUAAUGAGCUACUA | 0.143 |
| AH0242 | SEQ ID NO: 243 | AGGGAUAAUGAGCUACUAGUU | SEQ ID NO: 886 | CUAGUAGCUCAUUAUCCCUGC | SEQ ID NO: 1529 | AGGGAUAAUGAGCUACUAG | 0.325 |
| AH0243 | SEQ ID NO: 244 | GGGAUAAUGAGCUACUAGUUU | SEQ ID NO: 887 | ACUAGUAGCUCAUUAUCCCUG | SEQ ID NO: 1530 | GGGAUAAUGAGCUACUAGU | 0.085 |
| AH0244 | SEQ ID NO: 245 | GGAUAAUGAGCUACUAGUUUA | SEQ ID NO: 888 | AACUAGUAGCUCAUUAUCCCU | SEQ ID NO: 1531 | GGAUAAUGAGCUACUAGUU | 0.073 |
| AH0245 | SEQ ID NO: 246 | GAUAAUGAGCUACUAGUUUAU | SEQ ID NO: 889 | AAACUAGUAGCUCAUUAUCCC | SEQ ID NO: 1532 | GAUAAUGAGCUACUAGUUU | 0.085 |
| AH0246 | SEQ ID NO: 247 | AUAAUGAGCUACUAGUUUAUA | SEQ ID NO: 890 | UAAACUAGUAGCUCAUUAUCC | SEQ ID NO: 1533 | AUAAUGAGCUACUAGUUUA | 0.115 |
| AH0247 | SEQ ID NO: 248 | UAAUGAGCUACUAGUUUAUAA | SEQ ID NO: 891 | AUAAACUAGUAGCUCAUUAUC | SEQ ID NO: 1534 | UAAUGAGCUACUAGUUUAU | 0.115 |
| AH0248 | SEQ ID NO: 249 | AAUGAGCUACUAGUUUAUAAA | SEQ ID NO: 892 | UUAUAAACUAGUAGCUCAUUA | SEQ ID NO: 1535 | AAUGAGCUACUAGUUUAUA | 0.195 |
| AH0249 | SEQ ID NO: 250 | UGAGCUACUAGUUUAUAAAGA | SEQ ID NO: 893 | UUUAUAAACUAGUAGCUCAUU | SEQ ID NO: 1536 | UGAGCUACUAGUUUAUAAA | 0.124 |
| AH0250 | SEQ ID NO: 251 | GAGCUACUAGUUUAUAAAGAA | SEQ ID NO: 894 | CUUUAUAAACUAGUAGCUCAU | SEQ ID NO: 1537 | GAGCUACUAGUUUAUAAAG | 0.449 |
| AH0251 | SEQ ID NO: 252 | AGCUACUAGUUUAUAAAGAAA | SEQ ID NO: 895 | UCUUUAUAAACUAGUAGCUCA | SEQ ID NO: 1538 | AGCUACUAGUUUAUAAAGA | 0.131 |
| AH0252 | SEQ ID NO: 253 | GCUACUAGUUUAUAAAGAAAG | SEQ ID NO: 896 | UUCUUUAUAAACUAGUAGCUC | SEQ ID NO: 1539 | GCUACUAGUUUAUAAAGAA | 0.092 |
| AH0253 | SEQ ID NO: 254 | CUACUAGUUUAUAAAGAAAGA | SEQ ID NO: 897 | UUUCUUUAUAAACUAGUAGCU | SEQ ID NO: 1540 | CUACUAGUUUAUAAAGAAA | 0.091 |
| AH0254 | SEQ ID NO: 255 | AGUUUAUAAAGAAAGAGUUGG | SEQ ID NO: 898 | AACUCUUUCUUUAUAAACUAG | SEQ ID NO: 1541 | AGUUUAUAAAGAAAGAGUU | 0.327 |
| AH0255 | SEQ ID NO: 256 | AGCUACUAGUUGGAGUAUA | SEQ ID NO: 899 | UACUCCAACUCUUUCUUUA | SEQ ID NO: 1542 | AAGAAAGAGUUGGAGAGUA | 0.114 |
| AH0256 | SEQ ID NO: 257 | AGAAAGAGUUGGAGAGUAUAG | SEQ ID NO: 900 | AUACUCUCCAACUCUUUCUUU | SEQ ID NO: 1543 | AGAAAGAGUUGGAGAGUAU | 0.142 |
| AH0257 | SEQ ID NO: 258 | GAAAGAGUUGGAGAGUAUAGU | SEQ ID NO: 901 | UAUACUCUCCAACUCUUUCUU | SEQ ID NO: 1544 | GAAAGAGUUGGAGAGUAUA | 0.089 |
| AH0258 | SEQ ID NO: 259 | AAGAGUUGGAGAGUAUAGUCU | SEQ ID NO: 902 | ACUAUACUCUCCAACUCUUUC | SEQ ID NO: 1545 | AAGAGUUGGAGAGUAUAGU | 0.292 |
| AH0259 | SEQ ID NO: 260 | AGAGUUGGAGAGUAUAGUCUA | SEQ ID NO: 903 | GACUAUACUCUCCAACUCUUU | SEQ ID NO: 1546 | AGAGUUGGAGAGUAUAGUC | 0.178 |
| AH0260 | SEQ ID NO: 261 | GAGUUGGAGAGUAUAGUCUAU | SEQ ID NO: 904 | AGACUAUACUCUCCAACUCUU | SEQ ID NO: 1547 | GAGUUGGAGAGUAUAGUCU | 0.088 |
| AH0261 | SEQ ID NO: 262 | AGUUGGAGAGUAUAGUCUAUA | SEQ ID NO: 905 | UAGACUAUACUCUCCAACUCU | SEQ ID NO: 1548 | AGUUGGAGAGUAUAGUCUA | 0.034 |
| AH0262 | SEQ ID NO: 263 | GUUGGAGAGUAUAGUCUAUAC | SEQ ID NO: 906 | AUAGACUAUACUCUCCAACUC | SEQ ID NO: 1549 | GUUGGAGAGUAUAGUCUAU | 0.046 |
| AH0263 | SEQ ID NO: 264 | UUGGAGAGUAUAGUCUAUACA | SEQ ID NO: 907 | UAUAGACUAUACUCUCCAACU | SEQ ID NO: 1550 | UUGGAGAGUAUAGUCUAUA | 0.187 |

TABLE 1-continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0264 | SEQ ID NO: 265 | UGGAGAGUAUAGUCUAUACAU | SEQ ID NO: 908 | GUAUAGACUAUACUCUCCAAC | SEQ ID NO: 1551 | UGGAGAGUAUAGUCUAUAC | 0.357 |
| AH0265 | SEQ ID NO: 266 | GGAGAGUAUAGUCUAUACAUU | SEQ ID NO: 909 | UGUAUAGACUAUACUCUCCAA | SEQ ID NO: 1552 | GGAGAGUAUAGUCUAUACA | 0.133 |
| AH0266 | SEQ ID NO: 267 | GAGAGUAUAGUCUAUACAUUG | SEQ ID NO: 910 | AUGUAUAGACUAUACUCUCCA | SEQ ID NO: 1553 | GAGAGUAUAGUCUAUACAU | 0.430 |
| AH0267 | SEQ ID NO: 268 | AGAGUAUAGUCUAUACAUUGG | SEQ ID NO: 911 | AAUGUAUAGACUAUACUCUCC | SEQ ID NO: 1554 | AGAGUAUAGUCUAUACAUU | 0.079 |
| AH0268 | SEQ ID NO: 269 | GAGUAUAGUCUAUACAUUGGA | SEQ ID NO: 912 | CAAUGUAUAGACUAUACUCUC | SEQ ID NO: 1555 | GAGUAUAGUCUAUACAUUG | 0.139 |
| AH0269 | SEQ ID NO: 270 | AGUAUAGUCUAUACAUUGGAA | SEQ ID NO: 913 | CCAAUGUAUAGACUAUACUCU | SEQ ID NO: 1556 | AGUAUAGUCUAUACAUUGG | 0.291 |
| AH0270 | SEQ ID NO: 271 | GUAUAGUCUAUACAUUGGAAG | SEQ ID NO: 914 | UCCAAUGUAUAGACUAUACUC | SEQ ID NO: 1557 | GUAUAGUCUAUACAUUGGA | 0.145 |
| AH0271 | SEQ ID NO: 272 | GUCUAUACAUUGGAAGACACA | SEQ ID NO: 915 | UGUCUUCCAAUGUAUAGACUA | SEQ ID NO: 1558 | GUCUAUACAUUGGAAGACA | 0.249 |
| AH0272 | SEQ ID NO: 273 | CUAUACAUUGGAAGACACAAA | SEQ ID NO: 916 | UUGUCUUCCAAUGUAUAGAC | SEQ ID NO: 1559 | CUAUACAUUGGAAGACACA | 0.165 |
| AH0273 | SEQ ID NO: 274 | UAUACAUUGGAAGACACAAAG | SEQ ID NO: 917 | UUUGUGUCUUCCAAUGUAUAG | SEQ ID NO: 1560 | UAUACAUUGGAAGACACAA | 0.312 |
| AH0274 | SEQ ID NO: 275 | AUACAUUGGAAGACACAAAGU | SEQ ID NO: 918 | UUUUGUGUCUUCCAAUGUAUA | SEQ ID NO: 1561 | AUACAUUGGAAGACACAAA | 0.296 |
| AH0275 | SEQ ID NO: 276 | ACAUUGGAAGACACAAAGUUA | SEQ ID NO: 919 | ACUUUGUGUCUUCCAAUGUAU | SEQ ID NO: 1562 | ACAUUGGAAGACACAAAGU | 0.362 |
| AH0276 | SEQ ID NO: 277 | CAUUGGAAGACACAAAGUUAC | SEQ ID NO: 920 | AACUUUGUGUCUUCCAAUGUA | SEQ ID NO: 1563 | CAUUGGAAGACACAAAGUU | 0.098 |
| AH0277 | SEQ ID NO: 278 | AUUGGAAGACACAAAGUUACA | SEQ ID NO: 921 | UAACUUUGUGUCUUCCAAUGU | SEQ ID NO: 1564 | AUUGGAAGACACAAAGUUA | 0.165 |
| AH0278 | SEQ ID NO: 279 | UGGAAGACACAAAGUUACAUC | SEQ ID NO: 922 | UGUAACUUUGUGUCUUCCAAU | SEQ ID NO: 1565 | UGGAAGACACAAAGUUACA | 0.257 |
| AH0279 | SEQ ID NO: 280 | GGAAGACACAAAGUUACAUCC | SEQ ID NO: 923 | AUGUAACUUUGUGUCUUCCAA | SEQ ID NO: 1566 | GGAAGACACAAAGUUACAU | 0.191 |
| AH0280 | SEQ ID NO: 281 | GAAGACACAAAGUUACAUCCA | SEQ ID NO: 924 | GAUGUAACUUUGUGUCUUCCA | SEQ ID NO: 1567 | GAAGACACAAAGUUACAUC | 0.353 |
| AH0281 | SEQ ID NO: 282 | AAGACACAAAGUUACAUCCAA | SEQ ID NO: 925 | GGAUGUAACUUUGUGUCUUCC | SEQ ID NO: 1568 | AAGACACAAAGUUACAUCC | 0.390 |
| AH0282 | SEQ ID NO: 283 | AGACACAAAGUUACAUCCAAA | SEQ ID NO: 926 | UGGAUGUAACUUUGUGUCUUC | SEQ ID NO: 1569 | AGACACAAAGUUACAUCCA | 0.281 |
| AH0283 | SEQ ID NO: 284 | GACACAAAGUUACAUCCAAAG | SEQ ID NO: 927 | UUGGAUGUAACUUUGUGUCUU | SEQ ID NO: 1570 | GACACAAAGUUACAUCCAA | 0.059 |
| AH0284 | SEQ ID NO: 285 | ACACAAAGUUACAUCCAAAGU | SEQ ID NO: 928 | UUUGGAUGUAACUUUGUGUCU | SEQ ID NO: 1571 | ACACAAAGUUACAUCCAAA | 0.047 |
| AH0285 | SEQ ID NO: 286 | CACAAAGUUACAUCCAAAGUU | SEQ ID NO: 929 | CUUUGGAUGUAACUUUGUGUC | SEQ ID NO: 1572 | CACAAAGUUACAUCCAAAG | 0.246 |
| AH0286 | SEQ ID NO: 287 | CAAAGUUACAUCCAAAGUAU | SEQ ID NO: 930 | AACUUUGGAUGUAACUUUGUG | SEQ ID NO: 1573 | CAAAGUUACAUCCAAAGUU | 0.225 |
| AH0287 | SEQ ID NO: 288 | AAAGUUACAUCCAAAGUAUAC | SEQ ID NO: 931 | UAACUUUGGAUGUAACUUUGU | SEQ ID NO: 1574 | AAAGUUACAUCCAAAGUUA | 0.071 |

TABLE 1-continued

| Double stranded nucleic acid No. | Sense strand sequence (5'--->3') | SEQ ID NO: | Antisense strand sequence (5'--->3') | SEQ ID NO: | Target APCS mRNA sequence | SEQ ID NO: | APCS relative expression level |
|---|---|---|---|---|---|---|---|
| AH0288 | AAGUUACAUCCAAAGUUAUCG | SEQ ID NO: 289 | AUAAACUUUGGAUGUAACUUUG | SEQ ID NO: 932 | AAGUUACAUCCAAAGUUAU | SEQ ID NO: 1575 | 0.088 |
| AH0289 | AGUUACAUCCAAAGUUAUCGA | SEQ ID NO: 290 | GAUAAACUUUGGAUGUAACUUU | SEQ ID NO: 933 | AGUUACAUCCAAAGUUAUC | SEQ ID NO: 1576 | 0.276 |
| AH0290 | GUUACAUCCAAAGUUAUCGAA | SEQ ID NO: 291 | CGAUAACUUUGGAUGUAACUU | SEQ ID NO: 934 | GUUACAUCCAAAGUUAUCG | SEQ ID NO: 1577 | 0.240 |
| AH0291 | UUACAUCCAAAGUUAUCGAAA | SEQ ID NO: 292 | UCGAUAACUUUGGAUGUAACU | SEQ ID NO: 935 | UUACAUCCAAAGUUAUCGA | SEQ ID NO: 1578 | 0.352 |
| AH0292 | UACAUCCAAAGUUAUCGAAAA | SEQ ID NO: 293 | UUCGAUAACUUUGGAUGUAAC | SEQ ID NO: 936 | UACAUCCAAAGUUAUCGAA | SEQ ID NO: 1579 | 0.250 |
| AH0293 | ACAUCCAAAGUUAUCGAAAAG | SEQ ID NO: 294 | UUUCGAUAACUUUGGAUGUAA | SEQ ID NO: 937 | ACAUCCAAAGUUAUCGAAA | SEQ ID NO: 1580 | 0.266 |
| AH0294 | CAUCCAAAGUUAUCGAAAAGU | SEQ ID NO: 295 | UUUUCGAUAACUUUGGAUGUA | SEQ ID NO: 938 | CAUCCAAAGUUAUCGAAAA | SEQ ID NO: 1581 | 0.052 |
| AH0295 | AUCCAAAGUUAUCGAAAAGUU | SEQ ID NO: 296 | CUUUUCGAUAACUUUGGAUGU | SEQ ID NO: 939 | AUCCAAAGUUAUCGAAAAG | SEQ ID NO: 1582 | 0.245 |
| AH0296 | UCCAAAGUUAUCGAAAAGUUC | SEQ ID NO: 297 | ACUUUUCGAUAACUUUGGAUG | SEQ ID NO: 940 | UCCAAAGUUAUCGAAAAGU | SEQ ID NO: 1583 | 0.378 |
| AH0297 | CCAAAGUUAUCGAAAAGUUCC | SEQ ID NO: 298 | AACUUUUCGAUAACUUUGGA | SEQ ID NO: 941 | CCAAAGUUAUCGAAAAGUU | SEQ ID NO: 1584 | 0.131 |
| AH0298 | CAAAGUUAUCGAAAAGUUCCC | SEQ ID NO: 299 | GAACUUUUCGAUAACUUUGGA | SEQ ID NO: 942 | CAAAGUUAUCGAAAAGUUC | SEQ ID NO: 1585 | 0.062 |
| AH0299 | AAAGUUAUCGAAAAGUUCCCG | SEQ ID NO: 300 | UGGAGCCGGGAACUUUUCGAU | SEQ ID NO: 943 | AAAGUUAUCGAAAAGUUCC | SEQ ID NO: 1586 | 0.329 |
| AH0300 | AAGUUAUCGAAAAGUUCCCGG | SEQ ID NO: 301 | ACUGGAGCCGGGAACUUUUCG | SEQ ID NO: 944 | AAGUUAUCGAAAAGUUCCC | SEQ ID NO: 1587 | 0.346 |
| AH0301 | AGUUAUCGAAAAGUUCCCGGA | SEQ ID NO: 302 | GAUGUGGAGCCGGGAACUUUUC | SEQ ID NO: 945 | AGUUAUCGAAAAGUUCCCG | SEQ ID NO: 1588 | 0.368 |
| AH0302 | GUUAUCGAAAAGUUCCCGGAG | SEQ ID NO: 303 | CAGAUGUGGAGCCGGGAACUUU | SEQ ID NO: 946 | GUUAUCGAAAAGUUCCCGG | SEQ ID NO: 1589 | 0.296 |
| AH0303 | UUAUCGAAAAGUUCCCGGAGC | SEQ ID NO: 304 | ACAGAUGUGGAGCCGGGAACUUG | SEQ ID NO: 947 | UUAUCGAAAAGUUCCCGGA | SEQ ID NO: 1590 | 0.273 |
| AH0304 | UAUCGAAAAGUUCCCGGAGCC | SEQ ID NO: 305 | CACAGAUGUGGAGCCGGGAACG | SEQ ID NO: 948 | UAUCGAAAAGUUCCCGGAG | SEQ ID NO: 1591 | 0.075 |
| AH0305 | AUCGAAAAGUUCCCGGAGCCG | SEQ ID NO: 306 | ACACAGAUGUGGAGCCGGGACC | SEQ ID NO: 949 | AUCGAAAAGUUCCCGGAGCC | SEQ ID NO: 1592 | 0.280 |
| AH0306 | UCGAAAAGUUCCCGGAGCCGG | SEQ ID NO: 307 | UCACAGAUGUGGAGCCGGGAG | SEQ ID NO: 950 | UCGAAAAGUUCCCGGAGCC | SEQ ID NO: 1593 | 0.479 |
| AH0307 | CGAAAAGUUCCCGGAGCCGGG | SEQ ID NO: 308 | UCACACAGAUGUGGAGCCGGG | SEQ ID NO: 951 | CGAAAAGUUCCCGGAGCC | SEQ ID NO: 1594 | 0.452 |
| AH0308 | GAAAAGUUCCCGGAGCCGGGA | SEQ ID NO: 309 | AGCUCACACAGAUGUGGAGCUG | SEQ ID NO: 952 | GAAAAGUUCCCGGAGCCGG | SEQ ID NO: 1595 | 0.377 |
| AH0309 | AAAAGUUCCCGGAGCCGGGAAG | SEQ ID NO: 310 | CCAGCUCACACAGAUGUGGAC | SEQ ID NO: 953 | AAAAGUUCCCGGAGCCGGGA | SEQ ID NO: 1596 | 0.255 |
| AH0310 | AAAGUUCCCGGAGCCGGGAGU | SEQ ID NO: 311 | UCCCAGCUCACACAGAUGUGC | SEQ ID NO: 954 | AAAGUUCCCGGAGCCGGGAGU | SEQ ID NO: 1597 | 0.317 |
| AH0311 | AGUUCCCGGAGCCGGGAGUCC | SEQ ID NO: 312 | ACUCCCAGCUCACACAGAUGU | SEQ ID NO: 955 | AGUUCCCGGAGCCGGGAGUCCC | SEQ ID NO: 1598 | 0.234 |

TABLE 1-continued

| Double stranded nucleic acid No. | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|
| AH0312 | GUGUGAGCUGGGAGUCCUCAU | SEQ ID NO: 313 | GAGGACUCCCAGCUCACACAG | SEQ ID NO: 956 | GUGUGAGCUGGGAGUCCUC | SEQ ID NO: 1599 | 0.139 |
| AH0313 | AGCUGGGAGUCCUCCAGCAGGU | SEQ ID NO: 314 | CUGAUGGAGGACUCCCAGCUCA | SEQ ID NO: 957 | AGCUGGGAGUCCUCCAUCAG | SEQ ID NO: 1600 | 0.237 |
| AH0314 | GCUGGGAGUCCUCCAUCAGGUA | SEQ ID NO: 315 | CCUGAUGAGGAGACUCCCAGCUC | SEQ ID NO: 958 | GCUGGGAGUCCUCCAUCAGG | SEQ ID NO: 1601 | 0.223 |
| AH0315 | CUGGGAGUCCUCCAUCAGGUAU | SEQ ID NO: 316 | ACCUGAUGAGGAGACUCCCAGCU | SEQ ID NO: 959 | CUGGGAGUCCUCCAUCAGGU | SEQ ID NO: 1602 | 0.093 |
| AH0316 | UGGGAGUCCUCCAUCAGGUAUU | SEQ ID NO: 317 | UACCUGAUGAGGAGACUCCCAGC | SEQ ID NO: 960 | UGGGAGUCCUCCAUCAGGUA | SEQ ID NO: 1603 | 0.062 |
| AH0317 | GGGAGUCCUCCAUCAGGUAUUG | SEQ ID NO: 318 | AUACCUGAUGAGGAGACUCCCAG | SEQ ID NO: 961 | GGGAGUCCUCCAUCAGGUAU | SEQ ID NO: 1604 | 0.218 |
| AH0318 | GGAGUCCUCCAUCAGGUAUUGC | SEQ ID NO: 319 | AAUACCUGAUGAGGACUCCCA | SEQ ID NO: 962 | GGAGUCCUCCAUCAGGUAUU | SEQ ID NO: 1605 | 0.117 |
| AH0319 | GAGUCCUCCAUCAGGUAUUGCU | SEQ ID NO: 320 | CAAUACCUGAUGAGGAGACUCCC | SEQ ID NO: 963 | GAGUCCUCCAUCAGGUAUUG | SEQ ID NO: 1606 | 0.271 |
| AH0320 | GUCCUCCAUCAGGUAUUGCUGA | SEQ ID NO: 321 | AGCAAUACCUGAUGAGGAGACUC | SEQ ID NO: 964 | GUCCUCCAUCAGGUAUUGCU | SEQ ID NO: 1607 | 0.076 |
| AH0321 | UCCUCCAUCAGGUAUUGCUGAA | SEQ ID NO: 322 | CAGCAAUACCUGAUGAGGAGACU | SEQ ID NO: 965 | UCCUCCAUCAGGUAUUGCUG | SEQ ID NO: 1608 | 0.343 |
| AH0322 | CCUCCAUCAGGUAUUGCUGAAU | SEQ ID NO: 323 | UCAGCAAUACCUGAUGAGGAGAC | SEQ ID NO: 966 | CCUCCAUCAGGUAUUGCUGA | SEQ ID NO: 1609 | 0.104 |
| AH0323 | CUCCAUCAGGUAUUGCUGAAUU | SEQ ID NO: 324 | UUCAGCAAUACCUGAUGAGGAGA | SEQ ID NO: 967 | CUCCAUCAGGUAUUGCUGAA | SEQ ID NO: 1610 | 0.105 |
| AH0324 | UCAUCAGGUAUUGCUGAAUUUG | SEQ ID NO: 325 | AUUCAGCAAUACCUGAUGAGGAG | SEQ ID NO: 968 | UCAUCAGGUAUUGCUGAAU | SEQ ID NO: 1611 | 0.246 |
| AH0325 | CAUCAGGUAUUGCUGAAUUUUG | SEQ ID NO: 326 | AAUUCAGCAAUACCUGAUGAG | SEQ ID NO: 969 | CAUCAGGUAUUGCUGAAUU | SEQ ID NO: 1612 | 0.137 |
| AH0326 | AUCAGGUAUUGCUGAAUUUUGG | SEQ ID NO: 327 | AAAUUCAGCAAUACCUGAUGA | SEQ ID NO: 970 | AUCAGGUAUUGCUGAAUUU | SEQ ID NO: 1613 | 0.067 |
| AH0327 | UCAGGUAUUGCUGAAUUUUGGA | SEQ ID NO: 328 | AAAAUUCAGCAAUACCUGAUG | SEQ ID NO: 971 | UCAGGUAUUGCUGAAUUUU | SEQ ID NO: 1614 | 0.243 |
| AH0328 | CAGGUAUUGCUGAAUUUUGGAU | SEQ ID NO: 329 | CAAAAUUCAGCAAUACCUGAU | SEQ ID NO: 972 | CAGGUAUUGCUGAAUUUUG | SEQ ID NO: 1615 | 0.240 |
| AH0329 | AGGUAUUGCUGAAUUUUGGAUC | SEQ ID NO: 330 | CCAAAAUUCAGCAAUACCUGA | SEQ ID NO: 973 | AGGUAUUGCUGAAUUUUGG | SEQ ID NO: 1616 | 0.069 |
| AH0330 | GGUAUUGCUGAAUUUUGGAUCA | SEQ ID NO: 331 | UCCAAAAUUCAGCAAUACCUG | SEQ ID NO: 974 | GGUAUUGCUGAAUUUUGGA | SEQ ID NO: 1617 | 0.078 |
| AH0331 | GUAUUGCUGAAUUUUGGAUCAU | SEQ ID NO: 332 | AUCCAAAAUUCAGCAAUACCU | SEQ ID NO: 975 | GUAUUGCUGAAUUUUGGAU | SEQ ID NO: 1618 | 0.165 |
| AH0332 | AUUGCUGAAUUUUGGAUCAAU | SEQ ID NO: 333 | UGAUCCAAAAUUCAGCAAUAC | SEQ ID NO: 976 | AUUGCUGAAUUUUGGAUCA | SEQ ID NO: 1619 | 0.178 |
| AH0333 | UGCUGAAUUUUGGAUCAAUGG | SEQ ID NO: 334 | AUUGAUCCAAAAUUCAGCAA | SEQ ID NO: 977 | UGCUGAAUUUUGGAUCAAU | SEQ ID NO: 1620 | 0.220 |
| AH0334 | GCUGAAUUUUGGAUCAAUGGGA | SEQ ID NO: 335 | CAUUGAUCCAAAAUUCAGCA | SEQ ID NO: 978 | GCUGAAUUUUGGAUCAAUG | SEQ ID NO: 1621 | 0.160 |
| AH0335 | CUGAAUUUUGGAUCAAUGGAA | SEQ ID NO: 336 | CCAUUGAUCCAAAAUUCAGCA | SEQ ID NO: 979 | CUGAAUUUUGGAUCAAUGG | SEQ ID NO: 1622 | 0.311 |

TABLE 1 -continued

| Double stranded nucleic acid No. | Sense strand sequence (5'--->3') | SEQ ID NO: | Antisense strand sequence (5'--->3') | SEQ ID NO: | Target APCS mRNA sequence | SEQ ID NO: | APCS relative expression level |
|---|---|---|---|---|---|---|---|
| AH0336 | GAAUUUGGAUCAUGGGACA | SEQ ID NO: 337 | UCCCAUUGAUCCAAAAUUCAG | SEQ ID NO: 980 | GAAUUUGGAUCAAUGGGA | SEQ ID NO: 1623 | 0.130 |
| AH0337 | GGAUCAAUGGGACACCUUGG | SEQ ID NO: 338 | AAAGGUGUCCCAUUGAUCCAA | SEQ ID NO: 981 | GGAUCAAUGGGACACCUUU | SEQ ID NO: 1624 | 0.129 |
| AH0338 | CAAUGGGACACCUUUGGUGAA | SEQ ID NO: 339 | CACCAAAGGUGUCCCAUUGAU | SEQ ID NO: 982 | CAAUGGGACACCUUUGGUG | SEQ ID NO: 1625 | 0.365 |
| AH0339 | AAUGGGACACCUUUGGUGAAA | SEQ ID NO: 340 | UCACCAAAGGUGUCCCAUUGA | SEQ ID NO: 983 | AAUGGGACACCUUUGGUGA | SEQ ID NO: 1626 | 0.257 |
| AH0340 | AUGGGACACCUUUGGUGAAAA | SEQ ID NO: 341 | UUCACCAAAGGUGUCCCAUUG | SEQ ID NO: 984 | AUGGGACACCUUUGGUGAA | SEQ ID NO: 1627 | 0.333 |
| AH0341 | UGGGACACCUUUGGUGAAAAA | SEQ ID NO: 342 | UUUCACCAAAGGUGUCCCAU | SEQ ID NO: 985 | UGGGACACCUUUGGUGAAA | SEQ ID NO: 1628 | 0.326 |
| AH0342 | GGGACACCUUUGGUGAAAAAG | SEQ ID NO: 343 | UUUUCACCAAAGGUGUCCCA | SEQ ID NO: 986 | GGGACACCUUUGGUGAAAA | SEQ ID NO: 1629 | 0.195 |
| AH0343 | GGACACCUUUGGUGAAAAAGG | SEQ ID NO: 344 | UUUUUCACCAAAGGUGUCCCA | SEQ ID NO: 987 | GGACACCUUUGGUGAAAAA | SEQ ID NO: 1630 | 0.122 |
| AH0344 | ACCUUUGGUGAAAAAGGGUCU | SEQ ID NO: 345 | ACCCUUUUUCACCAAAGGUGU | SEQ ID NO: 988 | ACCUUUGGUGAAAAAGGGU | SEQ ID NO: 1631 | 0.253 |
| AH0345 | CCUUUGGUGAAAAAGGGUCUG | SEQ ID NO: 346 | GACCCUUUUUCACCAAAGGU | SEQ ID NO: 989 | CCUUUGGUGAAAAAGGGUC | SEQ ID NO: 1632 | 0.440 |
| AH0346 | CUUUGGUGAAAAAGGGUCUGC | SEQ ID NO: 347 | AGACCCUUUUUCACCAAAGGU | SEQ ID NO: 990 | CUUUGGUGAAAAAGGGUCU | SEQ ID NO: 1633 | 0.125 |
| AH0347 | GGUGAAAAAGGGUCUGCGACA | SEQ ID NO: 348 | UCGCAGACCCUUUUUCACCAA | SEQ ID NO: 991 | GGUGAAAAAGGGUCUGCGA | SEQ ID NO: 1634 | 0.082 |
| AH0348 | GUGAAAAAGGGUCUGCGACAG | SEQ ID NO: 349 | GUCGCAGACCCUUUUUCACCA | SEQ ID NO: 992 | GUGAAAAAGGGUCUGCGAC | SEQ ID NO: 1635 | 0.270 |
| AH0349 | UGAAAAAGGGUCUGCGACAGG | SEQ ID NO: 350 | UGUCGCAGACCCUUUUUCACC | SEQ ID NO: 993 | UGAAAAAGGGUCUGCGACA | SEQ ID NO: 1636 | 0.375 |
| AH0350 | GAAAAAGGGUCUGCGACAGGG | SEQ ID NO: 351 | CUGUCGCAGACCCUUUUUCAC | SEQ ID NO: 994 | GAAAAAGGGUCUGCGACAG | SEQ ID NO: 1637 | 0.376 |
| AH0351 | AAAGGGUCUGCGACAGGGUUA | SEQ ID NO: 352 | ACCCUGUCGCAGACCCUUUUU | SEQ ID NO: 995 | AAAGGGUCUGCGACAGGGU | SEQ ID NO: 1638 | 0.326 |
| AH0352 | AAGGGUCUGCGACAGGGUUAC | SEQ ID NO: 353 | AACCCUGUCGCAGACCCUUUU | SEQ ID NO: 996 | AAGGGUCUGCGACAGGGUU | SEQ ID NO: 1639 | 0.192 |
| AH0353 | AGGGUCUGCGACAGGGUUACU | SEQ ID NO: 354 | UAACCCUGUCGCAGACCCUUU | SEQ ID NO: 997 | AGGGUCUGCGACAGGGUUA | SEQ ID NO: 1640 | 0.106 |
| AH0354 | GGGUCUGCGACAGGGUUACUU | SEQ ID NO: 355 | GUAACCCUGUCGCAGACCCUU | SEQ ID NO: 998 | GGGUCUGCGACAGGGUUAC | SEQ ID NO: 1641 | 0.098 |
| AH0355 | GGUCUGCGACAGGGUUACUUU | SEQ ID NO: 356 | AGUAACCCUGUCGCAGACCCU | SEQ ID NO: 999 | GGUCUGCGACAGGGUUACU | SEQ ID NO: 1642 | 0.195 |
| AH0356 | GUCUGCGACAGGGUUACUUUG | SEQ ID NO: 357 | AAGUAACCCUGUCGCAGACCC | SEQ ID NO: 1000 | GUCUGCGACAGGGUUACUU | SEQ ID NO: 1643 | 0.154 |
| AH0357 | UCUGCGACAGGGUUACUUUGU | SEQ ID NO: 358 | AAAGUAACCCUGUCGCAGACC | SEQ ID NO: 1001 | UCUGCGACAGGGUUACUUU | SEQ ID NO: 1644 | 0.126 |
| AH0358 | CUGCGACAGGGUUACUUUGUA | SEQ ID NO: 359 | CAAAGUAACCCUGUCGCAGAC | SEQ ID NO: 1002 | CUGCGACAGGGUUACUUUG | SEQ ID NO: 1645 | 0.120 |
| AH0359 | UGCGACAGGGUUACUUUGUAG | SEQ ID NO: 360 | ACAAAGUAACCCUGUCGCAGA | SEQ ID NO: 1003 | UGCGACAGGGUUACUUUGU | SEQ ID NO: 1646 | 0.438 |

TABLE 1-continued

| Double stranded nucleic acid No. | Sense strand sequence (5'--->3') | SEQ ID NO: | Antisense strand sequence (5'--->3') | SEQ ID NO: | Target APCS mRNA sequence | SEQ ID NO: | APCS relative expression level |
|---|---|---|---|---|---|---|---|
| AH0360 | GCGACAGGGUUACUUUGUAGA | SEQ ID NO: 361 | UACAAAGUAACCCUGUCGCAG | SEQ ID NO: 1004 | GCGACAGGGUUACUUUGUA | SEQ ID NO: 1647 | 0.104 |
| AH0361 | CGACAGGGUUACUUUGUAGAA | SEQ ID NO: 362 | CUACAAAGUAACCCUGUCGCA | SEQ ID NO: 1005 | CGACAGGGUUACUUUGUAG | SEQ ID NO: 1648 | 0.290 |
| AH0362 | GACAGGGUUACUUUGUAGAAG | SEQ ID NO: 363 | UCUACAAAGUAACCCUGUCGC | SEQ ID NO: 1006 | GACAGGGUUACUUUGUAGA | SEQ ID NO: 1649 | 0.453 |
| AH0363 | ACAGGGUUACUUUGUAGAAGC | SEQ ID NO: 364 | UUCUACAAAGUAACCCUGUCG | SEQ ID NO: 1007 | ACAGGGUUACUUUGUAGAA | SEQ ID NO: 1650 | 0.467 |
| AH0364 | CAGGGUUACUUUGUAGAAGCU | SEQ ID NO: 365 | CUUCUACAAAGUAACCCUGUC | SEQ ID NO: 1008 | CAGGGUUACUUUGUAGAAG | SEQ ID NO: 1651 | 0.156 |
| AH0365 | AGGGUUACUUUGUAGAAGCUC | SEQ ID NO: 366 | GCUUCUACAAAGUAACCCUGU | SEQ ID NO: 1009 | AGGGUUACUUUGUAGAAGC | SEQ ID NO: 1652 | 0.280 |
| AH0366 | GGGUUACUUUGUAGAAGCUCA | SEQ ID NO: 367 | AGCUUCUACAAAGUAACCCUG | SEQ ID NO: 1010 | GGGUUACUUUGUAGAAGCU | SEQ ID NO: 1653 | 0.179 |
| AH0367 | GGUUACUUUGUAGAAGCUCAG | SEQ ID NO: 368 | GAGCUUCUACAAAGUAACCCU | SEQ ID NO: 1011 | GGUUACUUUGUAGAAGCUC | SEQ ID NO: 1654 | 0.222 |
| AH0368 | GUUACUUUGUAGAAGCUCAGC | SEQ ID NO: 369 | UGAGCUUCUACAAAGUAACCC | SEQ ID NO: 1012 | GUUACUUUGUAGAAGCUCA | SEQ ID NO: 1655 | 0.083 |
| AH0369 | UUACUUUGUAGAAGCUCAGCU | SEQ ID NO: 370 | CUGAGCUUCUACAAAGUAACC | SEQ ID NO: 1013 | UUACUUUGUAGAAGCUCAG | SEQ ID NO: 1656 | 0.313 |
| AH0370 | UACUUUGUAGAAGCUCAGCUC | SEQ ID NO: 371 | GCUGAGCUUCUACAAAGUAAC | SEQ ID NO: 1014 | UACUUUGUAGAAGCUCAGC | SEQ ID NO: 1657 | 0.088 |
| AH0371 | ACUUUGUAGAAGCUCAGCUCA | SEQ ID NO: 372 | AGCUGAGCUUCUACAAAGUAA | SEQ ID NO: 1015 | ACUUUGUAGAAGCUCAGCU | SEQ ID NO: 1658 | 0.093 |
| AH0372 | CUUUGUAGAAGCUCAGCUCAG | SEQ ID NO: 373 | CAGCUGAGCUUCUACAAAGUA | SEQ ID NO: 1016 | CUUUGUAGAAGCUCAGCUC | SEQ ID NO: 1659 | 0.142 |
| AH0373 | UUUGUAGAAGCUCAGCUCAGG | SEQ ID NO: 374 | UCAGCUGAGCUUCUACAAAGU | SEQ ID NO: 1017 | UUUGUAGAAGCUCAGCUCA | SEQ ID NO: 1660 | 0.255 |
| AH0374 | UUGUAGAAGCUCAGCUCAGGG | SEQ ID NO: 375 | CUCAGCUGAGCUUCUACAAAG | SEQ ID NO: 1018 | UUGUAGAAGCUCAGCUCAG | SEQ ID NO: 1661 | 0.308 |
| AH0375 | UGUAGAAGCUCAGCUCAGGGC | SEQ ID NO: 376 | CCUCAGCUGAGCUUCUACAAA | SEQ ID NO: 1019 | UGUAGAAGCUCAGCUCAGG | SEQ ID NO: 1662 | 0.097 |
| AH0376 | GUAGAAGCUCAGCUCAGGGCA | SEQ ID NO: 377 | CCCUCAGCUGAGCUUCUACAA | SEQ ID NO: 1020 | GUAGAAGCUCAGCUCAGGG | SEQ ID NO: 1663 | 0.316 |
| AH0377 | UAGAAGCUCAGCUCAGGGCAG | SEQ ID NO: 378 | CCCCUCAGCUGAGCUUCUACA | SEQ ID NO: 1021 | UAGAAGCUCAGCUCAGGGC | SEQ ID NO: 1664 | 0.116 |
| AH0378 | AGAAGCUCAGCUCAGGGCAGG | SEQ ID NO: 379 | CCCCCUCAGCUGAGCUUCUAC | SEQ ID NO: 1022 | AGAAGCUCAGCUCAGGGCA | SEQ ID NO: 1665 | 0.193 |
| AH0379 | GAAGCUCAGCUCAGGGCAGGA | SEQ ID NO: 380 | UCCCCCUCAGCUGAGCUUCUA | SEQ ID NO: 1023 | GAAGCUCAGCUCAGGGCAG | SEQ ID NO: 1666 | 0.432 |
| AH0380 | AAGCUCAGCUCAGGGCAGGAU | SEQ ID NO: 381 | AUCCCCCUCAGCUGAGCUUCU | SEQ ID NO: 1024 | AAGCUCAGCUCAGGGCAGG | SEQ ID NO: 1667 | 0.170 |
| AH0381 | AGCUCAGCUCAGGGCAGGAUU | SEQ ID NO: 382 | AAUCCCCCUCAGCUGAGCUUC | SEQ ID NO: 1025 | AGCUCAGCUCAGGGCAGGA | SEQ ID NO: 1668 | 0.448 |
| AH0382 | GCUCAGCUCAGGGCAGGAUUC | SEQ ID NO: 383 | GAAUCCCCCUCAGCUGAGCUU | SEQ ID NO: 1026 | GCUCAGCUCAGGGCAGGAU | SEQ ID NO: 1669 | 0.494 |
| AH0383 | CUCAGCUCAGGGCAGGAUUCC | SEQ ID NO: 384 | GGAAUCCCCCUCAGCUGAGCU | SEQ ID NO: 1027 | CUCAGCUCAGGGCAGGAUU | SEQ ID NO: 1670 | 0.244 |

TABLE 1 -continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0384 | SEQ ID NO: 385 | GGCAGGAACAGGAUUCCUAUG | SEQ ID NO: 1028 | UAGGAAUCCUGUUCCUGCCCC | SEQ ID NO: 1671 | GGCAGGAACAGGAUUCCUA | 0.074 |
| AH0385 | SEQ ID NO: 386 | GCAGGAACAGGAUUCCUAUGG | SEQ ID NO: 1029 | AUAGGAAUCCUGUUCCUGCCC | SEQ ID NO: 1672 | GCAGGAACAGGAUUCCUAU | 0.146 |
| AH0386 | SEQ ID NO: 387 | CAGGAACAGGAUUCCUAUGGG | SEQ ID NO: 1030 | CAUAGGAAUCCUGUUCCUGCC | SEQ ID NO: 1673 | CAGGAACAGGAUUCCUAUG | 0.280 |
| AH0387 | SEQ ID NO: 388 | GGAACAGGAUUCCUAUGGGGG | SEQ ID NO: 1031 | CCCCAUAGGAAUCCUGUUCCUG | SEQ ID NO: 1674 | GGAACAGGAUUCCUAUGGG | 0.260 |
| AH0388 | SEQ ID NO: 389 | GAACAGGAUUCCUAUGGGGGC | SEQ ID NO: 1032 | CCCCCAUAGGAAUCCUGUUCC | SEQ ID NO: 1675 | GAACAGGAUUCCUAUGGGG | 0.437 |
| AH0389 | SEQ ID NO: 390 | ACAGGAUUCCUAUGGGGGCAA | SEQ ID NO: 1033 | GCCCCCAUAGGAAUCCUGUUC | SEQ ID NO: 1676 | ACAGGAUUCCUAUGGGGGC | 0.349 |
| AH0390 | SEQ ID NO: 391 | CAGGAUUCCUAUGGGGGCAAG | SEQ ID NO: 1034 | UGCCCCCAUAGGAAUCCUGUU | SEQ ID NO: 1677 | CAGGAUUCCUAUGGGGGCA | 0.279 |
| AH0391 | SEQ ID NO: 392 | GGAUUCCUAUGGGGGCAAGUU | SEQ ID NO: 1035 | CUUGCCCCCAUAGGAAUCCUG | SEQ ID NO: 1678 | GGAUUCCUAUGGGGGCAAG | 0.153 |
| AH0392 | SEQ ID NO: 393 | GAUUCCUAUGGGGGCAAGUUU | SEQ ID NO: 1036 | ACUUGCCCCCAUAGGAAUCCU | SEQ ID NO: 1679 | GAUUCCUAUGGGGGCAAGU | 0.257 |
| AH0393 | SEQ ID NO: 394 | AUUCCUAUGGGGGCAAGUUUG | SEQ ID NO: 1037 | AACUUGCCCCCAUAGGAAUCC | SEQ ID NO: 1680 | AUUCCUAUGGGGGCAAGUU | 0.373 |
| AH0394 | SEQ ID NO: 395 | UUCCUAUGGGGGCAAGUUUGA | SEQ ID NO: 1038 | AAACUUGCCCCCAUAGGAAUC | SEQ ID NO: 1681 | UUCCUAUGGGGGCAAGUUU | 0.481 |
| AH0395 | SEQ ID NO: 396 | UCCUAUGGGGGCAAGUUUGAU | SEQ ID NO: 1039 | CAAACUUGCCCCCAUAGGAAU | SEQ ID NO: 1682 | UCCUAUGGGGGCAAGUUUG | 0.395 |
| AH0396 | SEQ ID NO: 397 | CCUAUGGGGGCAAGUUUGAUA | SEQ ID NO: 1040 | UCAAACUUGCCCCCAUAGGAA | SEQ ID NO: 1683 | CCUAUGGGGGCAAGUUUGA | 0.272 |
| AH0397 | SEQ ID NO: 398 | CUAUGGGGGCAAGUUUGAUAG | SEQ ID NO: 1041 | AUCAAACUUGCCCCCAUAGGA | SEQ ID NO: 1684 | CUAUGGGGGCAAGUUUGAU | 0.198 |
| AH0398 | SEQ ID NO: 399 | UAUGGGGGCAAGUUUGAUAGG | SEQ ID NO: 1042 | UAUCAAACUUGCCCCCAUAGG | SEQ ID NO: 1685 | UAUGGGGGCAAGUUUGAUA | 0.481 |
| AH0399 | SEQ ID NO: 400 | GGGGGCAAGUUUGAUAGGAGC | SEQ ID NO: 1043 | UCCUAUCAAACUUGCCCCCAU | SEQ ID NO: 1686 | GGGGGCAAGUUUGAUAGGA | 0.268 |
| AH0400 | SEQ ID NO: 401 | GGGCAAGUUUGAUAGGAGCC | SEQ ID NO: 1044 | CUCCUAUCAAACUUGCCCCCA | SEQ ID NO: 1687 | GGGCAAGUUUGAUAGGAG | 0.100 |
| AH0401 | SEQ ID NO: 402 | GGGCAAGUUUGAUAGGAGCCA | SEQ ID NO: 1045 | GCUCCUAUCAAACUUGCCCCC | SEQ ID NO: 1688 | GGGCAAGUUUGAUAGGAGC | 0.114 |
| AH0402 | SEQ ID NO: 403 | GGCAAGUUUGAUAGGAGCCAG | SEQ ID NO: 1046 | GGCUCCUAUCAAACUUGCCCC | SEQ ID NO: 1689 | GGCAAGUUUGAUAGGAGCC | 0.314 |
| AH0403 | SEQ ID NO: 404 | GCAAGUUUGAUAGGAGCCAGU | SEQ ID NO: 1047 | UGGCUCCUAUCAAACUUGCCC | SEQ ID NO: 1690 | GCAAGUUUGAUAGGAGCCA | 0.235 |
| AH0404 | SEQ ID NO: 405 | CAAGUUUGAUAGGAGCCAGUC | SEQ ID NO: 1048 | CUGGCUCCUAUCAAACUUGCC | SEQ ID NO: 1691 | CAAGUUUGAUAGGAGCCAG | 0.274 |
| AH0405 | SEQ ID NO: 406 | AAGUUUGAUAGGAGCCAGUCC | SEQ ID NO: 1049 | ACUGGCUCCUAUCAAACUUGC | SEQ ID NO: 1692 | AAGUUUGAUAGGAGCCAGU | 0.085 |
| AH0406 | SEQ ID NO: 407 | UUGAUAGGAGCCAGUCCUUUG | SEQ ID NO: 1050 | AAGGACUGGCUCCUAUCAAAC | SEQ ID NO: 1693 | UUGAUAGGAGCCAGUCCUU | 0.242 |
| AH0407 | SEQ ID NO: 408 | UGAUAGGAGCCAGUCCUUUGU | SEQ ID NO: 1051 | AAAGGACUGGCUCCUAUCAAA | SEQ ID NO: 1694 | UGAUAGGAGCCAGUCCUUU | 0.239 |

TABLE 1 -continued

| Double stranded nucleic acid No. | Sense strand SEQ ID NO | Sense strand sequence (5'--->3') | Antisense SEQ ID NO | Antisense strand sequence (5'--->3') | Target SEQ ID NO | Target APCS mRNA sequence | APCS relative expression level |
|---|---|---|---|---|---|---|---|
| AH0408 | SEQ ID NO: 409 | GAUAGGAGCCAGUCCUUUGUG | SEQ ID NO: 1052 | CAAAGGACUGGCUCCUAUCAA | SEQ ID NO: 1695 | GAUAGGAGCCAGUCCUUUG | 0.160 |
| AH0409 | SEQ ID NO: 410 | AUAGGAGCCAGUCCUUUGUGG | SEQ ID NO: 1053 | ACAAAGGACUGGCUCCUAUCA | SEQ ID NO: 1696 | AUAGGAGCCAGUCCUUUGU | 0.159 |
| AH0410 | SEQ ID NO: 411 | AGGAGCCAGUCCUUUGUGGGA | SEQ ID NO: 1054 | CCCACAAAGGACUGGCUCCUAU | SEQ ID NO: 1697 | AGGAGCCAGUCCUUUGUGG | 0.313 |
| AH0411 | SEQ ID NO: 412 | GGAGCCAGUCCUUUGUGGGAG | SEQ ID NO: 1055 | CCCACAAAGGACUGGCUCCUA | SEQ ID NO: 1698 | GGAGCCAGUCCUUUGUGGG | 0.232 |
| AH0412 | SEQ ID NO: 413 | GAGCCAGUCCUUUGUGGGAGA | SEQ ID NO: 1056 | UCCCACAAAGGACUGGCUCCU | SEQ ID NO: 1699 | GAGCCAGUCCUUUGUGGGA | 0.098 |
| AH0413 | SEQ ID NO: 414 | AGCCAGUCCUUUGUGGGAGAG | SEQ ID NO: 1057 | CUCCCACAAAGGACUGGCUCC | SEQ ID NO: 1700 | AGCCAGUCCUUUGUGGGAG | 0.325 |
| AH0414 | SEQ ID NO: 415 | GCCAGUCCUUUGUGGGAGAGA | SEQ ID NO: 1058 | UCUCCCACAAAGGACUGGCUC | SEQ ID NO: 1701 | GCCAGUCCUUUGUGGGAGA | 0.109 |
| AH0415 | SEQ ID NO: 416 | CCAGUCCUUUGUGGGAGAGAU | SEQ ID NO: 1059 | CUCUCCCACAAAGGACUGGCU | SEQ ID NO: 1702 | CCAGUCCUUUGUGGGAGAG | 0.367 |
| AH0416 | SEQ ID NO: 417 | CAGUCCUUUGUGGGAGAGAUU | SEQ ID NO: 1060 | UCUCUCCCACAAAGGACUGGC | SEQ ID NO: 1703 | CAGUCCUUUGUGGGAGAGA | 0.119 |
| AH0417 | SEQ ID NO: 418 | AGUCCUUUGUGGGAGAGAUUG | SEQ ID NO: 1061 | AAUCUCUCCCACAAAGGACUGG | SEQ ID NO: 1704 | AGUCCUUUGUGGGAGAGAU | 0.074 |
| AH0418 | SEQ ID NO: 419 | GUCCUUUGUGGGAGAGAUUGG | SEQ ID NO: 1062 | AAUCUCUCCCACAAAGGACUG | SEQ ID NO: 1705 | GUCCUUUGUGGGAGAGAUU | 0.095 |
| AH0419 | SEQ ID NO: 420 | UCCUUUGUGGGAGAGAUUGGG | SEQ ID NO: 1063 | CAAUCUCUCCCACAAAGGAC | SEQ ID NO: 1706 | UCCUUUGUGGGAGAGAUUG | 0.358 |
| AH0420 | SEQ ID NO: 421 | CCUUUGUGGGAGAGAUUGGGA | SEQ ID NO: 1064 | CCAAUCUCUCCCACAAAGGA | SEQ ID NO: 1707 | CCUUUGUGGGAGAGAUUGG | 0.315 |
| AH0421 | SEQ ID NO: 422 | CUUUGUGGGAGAGAUUGGGAA | SEQ ID NO: 1065 | CCCAAUCUCUCCCACAAAGG | SEQ ID NO: 1708 | CUUUGUGGGAGAGAUUGGG | 0.301 |
| AH0422 | SEQ ID NO: 423 | UUUGUGGGAGAGAUUGGGGAA | SEQ ID NO: 1066 | UCCCAAUCUCUCCCACAAAG | SEQ ID NO: 1709 | UUGUGGGAGAGAUUGGGGA | 0.214 |
| AH0423 | SEQ ID NO: 424 | UGUGGGAGAGAUUGGGGAUU | SEQ ID NO: 1067 | AUCCCAAUCUCUCCCACAAA | SEQ ID NO: 1710 | UGUGGGAGAGAUUGGGGAU | 0.087 |
| AH0424 | SEQ ID NO: 425 | GUGGGAGAGAUUGGGGAUUU | SEQ ID NO: 1068 | AAUCCCAAUCUCUCCCACAC | SEQ ID NO: 1711 | GUGGGAGAGAUUGGGGAUU | 0.099 |
| AH0425 | SEQ ID NO: 426 | UGGGAGAGAUUGGGGAUUUGU | SEQ ID NO: 1069 | AAAUCCCAAUCUCUCCCACA | SEQ ID NO: 1712 | UGGGAGAGAUUGGGGAUUU | 0.109 |
| AH0426 | SEQ ID NO: 427 | GGGAGAGAUUGGGGAUUUGUA | SEQ ID NO: 1070 | CAAAUCCCAAUCUCUCCCAC | SEQ ID NO: 1713 | GGGAGAGAUUGGGGAUUUG | 0.068 |
| AH0427 | SEQ ID NO: 428 | GGAGAGAUUGGGGAUUUGUAC | SEQ ID NO: 1071 | ACAAAUCCCAAUCUCUCCCA | SEQ ID NO: 1714 | GGAGAGAUUGGGGAUUUGU | 0.071 |
| AH0428 | SEQ ID NO: 429 | GAGAGAUUGGGGAUUUGUACA | SEQ ID NO: 1072 | UACAAAUCCCAAUCUCUCCC | SEQ ID NO: 1715 | GAGAGAUUGGGGAUUUGUA | 0.047 |
| AH0429 | SEQ ID NO: 430 | AGAGAUUGGGGAUUUGUACAU | SEQ ID NO: 1073 | GUACAAAUCCCAAUCUCUCC | SEQ ID NO: 1716 | AGAGAUUGGGGAUUUGUAC | 0.175 |
| AH0430 | SEQ ID NO: 431 | GAGAUUGGGGAUUUGUACAUG | SEQ ID NO: 1074 | UGUACAAAUCCCAAUCUCUC | SEQ ID NO: 1717 | GAGAUUGGGGAUUUGUACA | 0.079 |
| AH0431 | SEQ ID NO: 432 | AGAUUGGGGAUUUGUACAUGU | SEQ ID NO: 1075 | AUGUACAAAUCCCAAUCUCU | SEQ ID NO: 1718 | AGAUUGGGGAUUUGUACAU | 0.391 |

TABLE 1-continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0432 | SEQ ID NO: 433 | GGGGAUUUGUACAUGUGGGAC | SEQ ID NO: 1076 | CCCACACUGUACAAAUCCCCAA | SEQ ID NO: 1719 | GGGGAUUUGUACAUGUGGG | 0.154 |
| AH0433 | SEQ ID NO: 434 | GGGAUUUGUACAUGUGGGACU | SEQ ID NO: 1077 | UCCCACACUGUACAAAUCCCCA | SEQ ID NO: 1720 | GGGAUUUGUACAUGUGGGA | 0.087 |
| AH0434 | SEQ ID NO: 435 | GGAUUUGUACAUGUGGGACUC | SEQ ID NO: 1078 | GUCCCACACUGUACAAAUCCCC | SEQ ID NO: 1721 | GGAUUUGUACAUGUGGGAC | 0.324 |
| AH0435 | SEQ ID NO: 436 | GAUUUGUACAUGUGGGACUCU | SEQ ID NO: 1079 | AGUCCCACACUGUACAAAUCCC | SEQ ID NO: 1722 | GAUUUGUACAUGUGGGACU | 0.308 |
| AH0436 | SEQ ID NO: 437 | UGUACAUGUGGGACUCUGUGU | SEQ ID NO: 1080 | ACAGAGUCCCACAUGUACAAA | SEQ ID NO: 1723 | UGUACAUGUGGGACUCUGU | 0.210 |
| AH0437 | SEQ ID NO: 438 | GUACAUGUGGGACUCUGUGCU | SEQ ID NO: 1081 | CACAGAGUCCCACAUGUACAA | SEQ ID NO: 1724 | GUACAUGUGGGACUCUGUG | 0.384 |
| AH0438 | SEQ ID NO: 439 | ACAUGUGGGACUCUGUGCUGC | SEQ ID NO: 1082 | AGCACAGAGUCCCACAUGUAC | SEQ ID NO: 1725 | ACAUGUGGGACUCUGUGCU | 0.269 |
| AH0439 | SEQ ID NO: 440 | GGGACUCUGUGCUGCCCCCAG | SEQ ID NO: 1083 | GGGGGCAGCACAGAGUCCCAC | SEQ ID NO: 1726 | GGGACUCUGUGCUGCCCCC | 0.463 |
| AH0440 | SEQ ID NO: 441 | GGACUCUGUGCUGCCCCCAGA | SEQ ID NO: 1084 | UGGGGGCAGCACAGAGUCCCA | SEQ ID NO: 1727 | GGACUCUGUGCUGCCCCCA | 0.500 |
| AH0441 | SEQ ID NO: 442 | ACUCUGUGCUGCCCCCAGAAA | SEQ ID NO: 1085 | UCUGGGGGCAGCACAGAGUCC | SEQ ID NO: 1728 | ACUCUGUGCUGCCCCCAGA | 0.308 |
| AH0442 | SEQ ID NO: 443 | CUCUGUGCUGCCCCCAGAAAA | SEQ ID NO: 1086 | UUCUGGGGGCAGCACAGAGUC | SEQ ID NO: 1729 | CUCUGUGCUGCCCCCAGAA | 0.459 |
| AH0443 | SEQ ID NO: 444 | CUGUGCUGCCCCCAGAAAAAU | SEQ ID NO: 1087 | UUUUCUGGGGGCAGCACAGAG | SEQ ID NO: 1730 | CUGUGCUGCCCCCAGAAAA | 0.134 |
| AH0444 | SEQ ID NO: 445 | UGUGCUGCCCCCAGAAAAAUA | SEQ ID NO: 1088 | AUUUUCUGGGGGCAGCACAGA | SEQ ID NO: 1731 | UGUGCUGCCCCCAGAAAAU | 0.063 |
| AH0445 | SEQ ID NO: 446 | GUGCUGCCCCCAGAAAAAUAU | SEQ ID NO: 1089 | UAUUUUCUGGGGGCAGCACAG | SEQ ID NO: 1732 | GUGCUGCCCCCAGAAAAUA | 0.433 |
| AH0446 | SEQ ID NO: 447 | GCUGCCCCCAGAAAAAUAUCC | SEQ ID NO: 1090 | GAUAUUUUCUGGGGGCAGCAC | SEQ ID NO: 1733 | GCUGCCCCCAGAAAAAUAUC | 0.414 |
| AH0447 | SEQ ID NO: 448 | CCCCCAGAAAAAUAUCCUGUCU | SEQ ID NO: 1091 | ACAGGAUAUUUUCUGGGGGCA | SEQ ID NO: 1734 | CCCCCAGAAAAAUAUCCUGU | 0.189 |
| AH0448 | SEQ ID NO: 449 | CCCCAGAAAAAUAUCCUGUCUG | SEQ ID NO: 1092 | AGACAGGAUAUUUUCUGGGGG | SEQ ID NO: 1735 | CCCCAGAAAAAUAUCCUGUCU | 0.489 |
| AH0449 | SEQ ID NO: 450 | CCAGAAAAAUAUCCUGUCUGCC | SEQ ID NO: 1093 | CAGACAGGAUAUUUUCUGGGG | SEQ ID NO: 1736 | CCAGAAAAAUAUCCUGUCUG | 0.353 |
| AH0450 | SEQ ID NO: 451 | CAGAAAAAUAUCCUGUCUGCCU | SEQ ID NO: 1094 | GCAGACAGGAUAUUUUCUGGG | SEQ ID NO: 1737 | CAGAAAAAUAUCCUGUCUGC | 0.293 |
| AH0451 | SEQ ID NO: 452 | GAAAAAUAUCCUGUCUGCCUAU | SEQ ID NO: 1095 | AGGCAGACAGGAUAUUUUCUG | SEQ ID NO: 1738 | GAAAAAUAUCCUGUCUGCCU | 0.121 |
| AH0452 | SEQ ID NO: 453 | AAAAAUAUCCUGUCUGCCUAUC | SEQ ID NO: 1096 | UAGGCAGACAGGAUAUUUUCU | SEQ ID NO: 1739 | AAAAAUAUCCUGUCUGCCUA | 0.053 |
| AH0453 | SEQ ID NO: 454 | AAAUAUCCUGUCUGCCUAUCA | SEQ ID NO: 1097 | AUAGGCAGACAGGAUAUUUUC | SEQ ID NO: 1740 | AAAUAUCCUGUCUGCCUAU | 0.109 |
| AH0454 | SEQ ID NO: 455 | CCUGUCUGCCUAUCAGGGUAC | SEQ ID NO: 1098 | ACCCUGAUAGGCAGACAGGAU | SEQ ID NO: 1741 | CCUGUCUGCCUAUCAGGGU | 0.298 |
| AH0455 | SEQ ID NO: 456 | CUGUCUGCCUAUCAGGGUACC | SEQ ID NO: 1099 | UACCCUGAUAGGCAGACAGGA | SEQ ID NO: 1742 | CUGUCUGCCUAUCAGGGUA | 0.113 |

TABLE 1 -continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0456 | SEQ ID NO: 457 | GUCUGCCUAUCAGGGUACCCC | SEQ ID NO: 1100 | GGUACCCUGAUAGGCAGACAG | SEQ ID NO: 1743 | GUCUGCCUAUCAGGGUACC | 0.336 |
| AH0457 | SEQ ID NO: 458 | UGCCUAUCAGGGUACCCCUCU | SEQ ID NO: 1101 | AGGGGUACCCUGAUAGGCAGA | SEQ ID NO: 1744 | UGCCUAUCAGGGUACCCCU | 0.251 |
| AH0458 | SEQ ID NO: 459 | GCCUAUCAGGGUACCCCUCUC | SEQ ID NO: 1102 | GAGGGGUACCCUGAUAGGCAG | SEQ ID NO: 1745 | GCCUAUCAGGGUACCCUC | 0.218 |
| AH0459 | SEQ ID NO: 460 | CCUAUCAGGGUACCCCUCUCC | SEQ ID NO: 1103 | AGAGGGGUACCCUGAUAGGCA | SEQ ID NO: 1746 | CCUAUCAGGGUACCCCUCU | 0.403 |
| AH0460 | SEQ ID NO: 461 | CUAUCAGGGUACCCCUCUCCC | SEQ ID NO: 1104 | GAGAGGGGUACCCUGAUAGGC | SEQ ID NO: 1747 | CUAUCAGGGUACCCCUCUC | 0.104 |
| AH0461 | SEQ ID NO: 462 | CAGGGUACCCCUCUCCCUGCC | SEQ ID NO: 1105 | CAGGGAGAGGGGUACCCUGAU | SEQ ID NO: 1748 | CAGGGUACCCCUCUCCCUG | 0.300 |
| AH0462 | SEQ ID NO: 463 | GGGUACCCCUCUCCCUGCCA | SEQ ID NO: 1106 | GGCAGGGAGAGGGGUACCCUG | SEQ ID NO: 1749 | GGGUACCCCUCUCCCUGCC | 0.463 |
| AH0463 | SEQ ID NO: 464 | GGUACCCCUCUCCCUGCCAAU | SEQ ID NO: 1107 | UGGCAGGGAGAGGGGUACCCU | SEQ ID NO: 1750 | GGUACCCCUCUCCCUGCCA | 0.476 |
| AH0464 | SEQ ID NO: 465 | GUACCCCUCUCCCUGCCAAUA | SEQ ID NO: 1108 | UUGGCAGGGAGAGGGGUACCC | SEQ ID NO: 1751 | GUACCCCUCUCCCUGCCAA | 0.159 |
| AH0465 | SEQ ID NO: 466 | UACCCCUCUCCCUGCCAAUAU | SEQ ID NO: 1109 | AUUGGCAGGGAGAGGGGUACC | SEQ ID NO: 1752 | UACCCCUCUCCCUGCCAAU | 0.391 |
| AH0466 | SEQ ID NO: 467 | CCCCUCUCCCUGCCAAUAUCC | SEQ ID NO: 1110 | AUAUUGGCAGGGAGAGGGGUA | SEQ ID NO: 1753 | CCCCUCUCCCUGCCAAUAUC | 0.389 |
| AH0467 | SEQ ID NO: 468 | CCCUCUCCCUGCCAAUAUCCU | SEQ ID NO: 1111 | GAUAUUGCAGGGAGAGGGGU | SEQ ID NO: 1754 | CCCUCUCCCUGCCAAUAUC | 0.208 |
| AH0468 | SEQ ID NO: 469 | CUGCCAAUAUCCUGGACUGCG | SEQ ID NO: 1112 | CAGUCCAGGAUAUUGGCAGGG | SEQ ID NO: 1755 | CUGCCAAUAUCCUGGACUG | 0.333 |
| AH0469 | SEQ ID NO: 470 | CCAAUAUCCUGGACUGGCAGG | SEQ ID NO: 1113 | UGCCAGUCCAGGAUAUUGGCA | SEQ ID NO: 1756 | CCAAUAUCCUGGACUGGCA | 0.120 |
| AH0470 | SEQ ID NO: 471 | CAAUAUCCUGGACUGGCAGC | SEQ ID NO: 1114 | CUGCCAGUCCAGGAUAUUGGC | SEQ ID NO: 1757 | CAAUAUCCUGGACUGGCAG | 0.299 |
| AH0471 | SEQ ID NO: 472 | UCCUGGACUGGCAGCCUCUGA | SEQ ID NO: 1115 | AGAGCCUGCCAGUCCAGGAUA | SEQ ID NO: 1758 | UCCUGGACUGGCAGGCUCU | 0.386 |
| AH0472 | SEQ ID NO: 473 | CCUGGACUGGCAGCCUCUGAA | SEQ ID NO: 1116 | CAGAGGCCUGCCAGUCCAGGAU | SEQ ID NO: 1759 | CCUGGACUGGCAGGCUCUG | 0.463 |
| AH0473 | SEQ ID NO: 474 | CUGGACUGGCAGCCUCUGA | SEQ ID NO: 1117 | UCAGAGGCCUGCCAGUCCAGGA | SEQ ID NO: 1760 | CUGGACUGGCAGCCUCUGA | 0.454 |
| AH0474 | SEQ ID NO: 475 | UGGACUGGCAGCCUCUGAACU | SEQ ID NO: 1118 | UUCAGAGGCCUGCCAGUCCAGG | SEQ ID NO: 1761 | UGGACUGGCAGCCUCUGAA | 0.085 |
| AH0475 | SEQ ID NO: 476 | GGACUGGCAGCCUCUGAACUA | SEQ ID NO: 1119 | GUUCAGAGGCCUGCCAGUCCAG | SEQ ID NO: 1762 | GGACUGGCAGCCUCUGAAC | 0.383 |
| AH0476 | SEQ ID NO: 477 | GACUGGCAGCCUCUGAACUAU | SEQ ID NO: 1120 | AGUUCAGAGGCCUGCCAGUCCA | SEQ ID NO: 1763 | GACUGGCAGCCUCUGAACU | 0.308 |
| AH0477 | SEQ ID NO: 478 | ACUGGCAGCCUCUGAACUAUG | SEQ ID NO: 1121 | UAGUUCAGAGCCUGCCAGUCC | SEQ ID NO: 1764 | ACUGGCAGCCUCUGAACUA | 0.177 |
| AH0478 | SEQ ID NO: 479 | CUGGCAGCCUCUGAACUAUGA | SEQ ID NO: 1122 | AUAGUUCAGAGCCUGCCAGUC | SEQ ID NO: 1765 | CUGGCAGCCUCUGAACUAU | 0.096 |
| AH0479 | SEQ ID NO: 480 | UGGCAGCCUCUGAACUAUGAA | SEQ ID NO: 1123 | CAUAGUUCAGAGCCUGCCAGU | SEQ ID NO: 1766 | UGGCAGCCUCUGAACUAUG | 0.306 |

TABLE 1 -continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0480 | SEQ ID NO: 481 | GGCAGGCUCUGAACUAUGAAA | SEQ ID NO: 1124 | UCAUAGUUCAGAGCCUGCCAG | SEQ ID NO: 1767 | GGCAGGCUCUGAACUAUGA | 0.077 |
| AH0481 | SEQ ID NO: 482 | GCAGGCUCUGAACUAUGAAAU | SEQ ID NO: 1125 | UUCAUAGUUCAGAGCCUGCCA | SEQ ID NO: 1768 | GCAGGCUCUGAACUAUGAA | 0.406 |
| AH0482 | SEQ ID NO: 483 | CAGGCUCUGAACUAUGAAAUC | SEQ ID NO: 1126 | UUUCAUAGUUCAGAGCCUGCC | SEQ ID NO: 1769 | CAGGCUCUGAACUAUGAAA | 0.133 |
| AH0483 | SEQ ID NO: 484 | AGGCUCUGAACUAUGAAAUCA | SEQ ID NO: 1127 | AUUUCAUAGUUCAGAGCCUGC | SEQ ID NO: 1770 | AGGCUCUGAACUAUGAAAU | 0.137 |
| AH0484 | SEQ ID NO: 485 | GGCUCUGAACUAUGAAAUCAG | SEQ ID NO: 1128 | GAUUUCAUAGUUCAGAGCCUG | SEQ ID NO: 1771 | GGCUCUGAACUAUGAAAUC | 0.085 |
| AH0485 | SEQ ID NO: 486 | GCUCUGAACUAUGAAAUCAGA | SEQ ID NO: 1129 | UGAUUUCAUAGUUCAGAGCC | SEQ ID NO: 1772 | GCUCUGAACUAUGAAAUCA | 0.217 |
| AH0486 | SEQ ID NO: 487 | CUCUGAACUAUGAAAUCAGAG | SEQ ID NO: 1130 | CUGAUUUCAUAGUUCAGAGCC | SEQ ID NO: 1773 | CUCUGAACUAUGAAAUCAG | 0.197 |
| AH0487 | SEQ ID NO: 488 | UCUGAACUAUGAAAUCAGAGG | SEQ ID NO: 1131 | UCUGAUUUCAUAGUUCAGAGC | SEQ ID NO: 1774 | UCUGAACUAUGAAAUCAGA | 0.296 |
| AH0488 | SEQ ID NO: 489 | GAACUAUGAAAUCAGAGGAUA | SEQ ID NO: 1132 | UCCUCUGAUUUCAUAGUUCAG | SEQ ID NO: 1775 | GAACUAUGAAAUCAGAGGA | 0.128 |
| AH0489 | SEQ ID NO: 490 | AACUAUGAAAUCAGAGGAUAU | SEQ ID NO: 1133 | AUCCUCUGAUUUCAUAGUUCA | SEQ ID NO: 1776 | AACUAUGAAAUCAGAGGAU | 0.230 |
| AH0490 | SEQ ID NO: 491 | ACUAUGAAAUCAGAGGAUAUG | SEQ ID NO: 1134 | UAUCCUCUGAUUUCAUAGUU | SEQ ID NO: 1777 | ACUAUGAAAUCAGAGGAUA | 0.125 |
| AH0491 | SEQ ID NO: 492 | CUAUGAAAUCAGAGGAUAUGU | SEQ ID NO: 1135 | AUAUCCUCUGAUUUCAUAGU | SEQ ID NO: 1778 | CUAUGAAAUCAGAGGAUAU | 0.104 |
| AH0492 | SEQ ID NO: 493 | UAUGAAAUCAGAGGAUAUGUC | SEQ ID NO: 1136 | CAUAUCCUCUGAUUUCAUAGU | SEQ ID NO: 1779 | UAUGAAAUCAGAGGAUAUG | 0.330 |
| AH0493 | SEQ ID NO: 494 | UGAAAUCAGAGGAUAUGUCAU | SEQ ID NO: 1137 | GACAUAUCCUCUGAUUUCAUA | SEQ ID NO: 1780 | UGAAAUCAGAGGAUAUGUC | 0.338 |
| AH0494 | SEQ ID NO: 495 | GAAAUCAGAGGAUAUGUCAUC | SEQ ID NO: 1138 | UGACAUAUCCUCUGAUUUCAU | SEQ ID NO: 1781 | GAAAUCAGAGGAUAUGUCA | 0.043 |
| AH0495 | SEQ ID NO: 496 | AAAUCAGAGGAUAUGUCAUCA | SEQ ID NO: 1139 | AUGACAUAUCCUCUGAUUUCA | SEQ ID NO: 1782 | AAAUCAGAGGAUAUGUCAU | 0.084 |
| AH0496 | SEQ ID NO: 497 | AAUCAGAGGAUAUGUCAUCAU | SEQ ID NO: 1140 | GAUGACAUAUCCUCUGAUUUC | SEQ ID NO: 1783 | AAUCAGAGGAUAUGUCAUC | 0.489 |
| AH0497 | SEQ ID NO: 498 | CAGAGGAUAUGUCAUCAUCAA | SEQ ID NO: 1141 | GAUGAUGACAUAUCCUCUGAU | SEQ ID NO: 1784 | CAGAGGAUAUGUCAUCAUC | 0.142 |
| AH0498 | SEQ ID NO: 499 | AGAGGAUAUGUCAUCAUCAAA | SEQ ID NO: 1142 | UGAUGAUGACAUAUCCUCUGA | SEQ ID NO: 1785 | AGAGGAUAUGUCAUCAUCA | 0.079 |
| AH0499 | SEQ ID NO: 500 | GAGGAUAUGUCAUCAUCAAAC | SEQ ID NO: 1143 | UUGAUGAUGACAUAUCCUCUG | SEQ ID NO: 1786 | GAGGAUAUGUCAUCAUCAA | 0.079 |
| AH0500 | SEQ ID NO: 501 | AGGAUAUGUCAUCAUCAAACC | SEQ ID NO: 1144 | UUUGAUGAUGACAUAUCCUCU | SEQ ID NO: 1787 | AGGAUAUGUCAUCAUCAAA | 0.091 |
| AH0501 | SEQ ID NO: 502 | GGAUAUGUCAUCAUCAAACCC | SEQ ID NO: 1145 | GUUUGAUGAUGACAUAUCCUC | SEQ ID NO: 1788 | GGAUAUGUCAUCAUCAAAC | 0.062 |
| AH0502 | SEQ ID NO: 503 | GAUAUGUCAUCAUCAAACCCU | SEQ ID NO: 1146 | GGUUUGAUGAUGACAUAUCCU | SEQ ID NO: 1789 | GAUAUGUCAUCAUCAAACC | 0.343 |
| AH0503 | SEQ ID NO: 504 | AUGUCAUCAUCAAACCCUGG | SEQ ID NO: 1147 | AAGGGUUUGAUGAUGACAUAU | SEQ ID NO: 1790 | AUGUCAUCAUCAAACCCUU | 0.173 |

TABLE 1-continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0504 | SEQ ID NO: 505 | CAUCAUCAAACCCUUGGUGUG | SEQ ID NO: 1148 | CACCAAGGGUUUGAUGAUGAC | SEQ ID NO: 1791 | CAUCAUCAAACCCUUGGUG | 0.442 |
| AH0505 | SEQ ID NO: 506 | UCAUCAAACCCUUGGUGUGG | SEQ ID NO: 1149 | CACACCAAGGGUUUGAUGAUG | SEQ ID NO: 1792 | UCAUCAAACCCUUGGUGUG | 0.355 |
| AH0506 | SEQ ID NO: 507 | ACCCUUGGUGUGGGUCUGAGG | SEQ ID NO: 1150 | UCAGACCCACACCAAGGGUUU | SEQ ID NO: 1793 | ACCCUUGGUGUGGGUCUGA | 0.393 |
| AH0507 | SEQ ID NO: 508 | CCCUUGGUGUGGGUCUGAGGU | SEQ ID NO: 1151 | CUCAGACCCACACCAAGGGUU | SEQ ID NO: 1794 | CCCUUGGUGUGGGUCUGAG | 0.273 |
| AH0508 | SEQ ID NO: 509 | CCUUGGUGUGGGUCUGAGGUC | SEQ ID NO: 1152 | CCUCAGACCCACACCAAGGGU | SEQ ID NO: 1795 | CCUUGGUGUGGGUCUGAGG | 0.137 |
| AH0509 | SEQ ID NO: 510 | CUUGGUGUGGGUCUGAGGUCU | SEQ ID NO: 1153 | ACCUCAGACCCACACCAAGGG | SEQ ID NO: 1796 | CUUGGUGUGGGUCUGAGGU | 0.220 |
| AH0510 | SEQ ID NO: 511 | UGGUGUGGGUCUGAGGUCUGA | SEQ ID NO: 1154 | AGACCUCAGACCCACACCAAG | SEQ ID NO: 1797 | UGGUGUGGGUCUGAGGUCU | 0.086 |
| AH0511 | SEQ ID NO: 512 | GGUGUGGGUCUGAGGUCUGAG | SEQ ID NO: 1155 | AAGACCUCAGACCCACACCAA | SEQ ID NO: 1798 | GGUGUGGGUCUGAGGUCUU | 0.125 |
| AH0512 | SEQ ID NO: 513 | GUGUGGGUCUGAGGUCUGAGG | SEQ ID NO: 1156 | CAAGACCUCAGACCCACACCA | SEQ ID NO: 1799 | GUGUGGGUCUGAGGUCUUG | 0.066 |
| AH0513 | SEQ ID NO: 514 | UGUGGGUCUGAGGUCUUGACU | SEQ ID NO: 1157 | UCAAGACCUCAGACCCACACC | SEQ ID NO: 1800 | UGUGGGUCUGAGGUCUUGA | 0.104 |
| AH0514 | SEQ ID NO: 515 | GUGGGUCUGAGGUCUUGACUC | SEQ ID NO: 1158 | GUCAAGACCUCAGACCCACAC | SEQ ID NO: 1801 | GUGGGUCUGAGGUCUUGAC | 0.098 |
| AH0515 | SEQ ID NO: 516 | GGGUCUGAGGUCUUGACUCAA | SEQ ID NO: 1159 | GAGUCAAGACCUCAGACCCAC | SEQ ID NO: 1802 | GGGUCUGAGGUCUUGACUC | 0.136 |
| AH0516 | SEQ ID NO: 517 | GGUCUGAGGUCUUGACUCAAC | SEQ ID NO: 1160 | UGAGUCAAGACCUCAGACCCA | SEQ ID NO: 1803 | GGUCUGAGGUCUUGACUCA | 0.072 |
| AH0517 | SEQ ID NO: 518 | GUCUGAGGUCUUGACUCAACG | SEQ ID NO: 1161 | UUGAGUCAAGACCUCAGACCC | SEQ ID NO: 1804 | GUCUGAGGUCUUGACUCAA | 0.146 |
| AH0518 | SEQ ID NO: 519 | CUGAGGUCUUGACUCAACGAG | SEQ ID NO: 1162 | CGUUGAGUCAAGACCUCAGAC | SEQ ID NO: 1805 | CUGAGGUCUUGACUCAACG | 0.241 |
| AH0519 | SEQ ID NO: 520 | UGAGGUCUUGACUCAACGAGA | SEQ ID NO: 1163 | UCGUUGAGUCAAGACCUCAGA | SEQ ID NO: 1806 | UGAGGUCUUGACUCAACGA | 0.087 |
| AH0520 | SEQ ID NO: 521 | GAGGUCUUGACUCAACGAGAG | SEQ ID NO: 1164 | CUCGUUGAGUCAAGACCUCAG | SEQ ID NO: 1807 | GAGGUCUUGACUCAACGAG | 0.096 |
| AH0521 | SEQ ID NO: 522 | AGGUCUUGACUCAACGAGAGC | SEQ ID NO: 1165 | UCUCGUUGAGUCAAGACCUCA | SEQ ID NO: 1808 | AGGUCUUGACUCAACGAGA | 0.069 |
| AH0522 | SEQ ID NO: 523 | GGUCUUGACUCAACGAGAGCA | SEQ ID NO: 1166 | CCUCGUUGAGUCAAGACCUC | SEQ ID NO: 1809 | GGUCUUGACUCAACGAGAG | 0.077 |
| AH0523 | SEQ ID NO: 524 | GUCUUGACUCAACGAGAGCAC | SEQ ID NO: 1167 | GCUCUCGUUGAGUCAAGACCU | SEQ ID NO: 1810 | GUCUUGACUCAACGAGAGC | 0.218 |
| AH0524 | SEQ ID NO: 525 | UCUUGACUCAACGAGAGCACU | SEQ ID NO: 1168 | UGCUCUCGUUGAGUCAAGACC | SEQ ID NO: 1811 | UCUUGACUCAACGAGAGCA | 0.125 |
| AH0525 | SEQ ID NO: 526 | CUUGACUCAACGAGAGCACUU | SEQ ID NO: 1169 | GUGCUCUCGUUGAGUCAAGAC | SEQ ID NO: 1812 | CUUGACUCAACGAGAGCAC | 0.195 |
| AH0526 | SEQ ID NO: 527 | UUGACUCAACGAGAGCACUUG | SEQ ID NO: 1170 | AGUGCUCUCGUUGAGUCAAGA | SEQ ID NO: 1813 | UUGACUCAACGAGAGCACU | 0.101 |
| AH0527 | SEQ ID NO: 528 | UGACUCAACGAGAGCACUUGA | SEQ ID NO: 1171 | AAGUGCUCUCGUUGAGUCAAG | SEQ ID NO: 1814 | UGACUCAACGAGAGCACUU | 0.189 |

TABLE 1-continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0528 | SEQ ID NO: 529 | GACUCAACGAGAGCACUUGAA | SEQ ID NO: 1172 | CAAGUGCUCUCGUUGAGUCAA | SEQ ID NO: 1815 | GACUCAACGAGAGCACUUG | 0.090 |
| AH0529 | SEQ ID NO: 530 | ACUCAACGAGAGCACUUGAAA | SEQ ID NO: 1173 | UCAAGUGCUCUCGUUGAGUCA | SEQ ID NO: 1816 | ACUCAACGAGAGCACUUGA | 0.104 |
| AH0530 | SEQ ID NO: 531 | CUCAACGAGAGCACUUGAAAA | SEQ ID NO: 1174 | UUCAAGUGCUCUCGUUGAGUC | SEQ ID NO: 1817 | CUCAACGAGAGCACUUGAA | 0.107 |
| AH0531 | SEQ ID NO: 532 | UCAACGAGAGCACUUGAAAAU | SEQ ID NO: 1175 | UUUCAAGUGCUCUCGUUGAGU | SEQ ID NO: 1818 | UCAACGAGAGCACUUGAAA | 0.063 |
| AH0532 | SEQ ID NO: 533 | CAACGAGAGCACUUGAAAAUG | SEQ ID NO: 1176 | UUUUCAAGUGCUCUCGUUGAG | SEQ ID NO: 1819 | CAACGAGAGCACUUGAAAA | 0.066 |
| AH0533 | SEQ ID NO: 534 | AACGAGAGCACUUGAAAAUGA | SEQ ID NO: 1177 | AUUUUCAAGUGCUCUCGUUGA | SEQ ID NO: 1820 | AACGAGAGCACUUGAAAAU | 0.054 |
| AH0534 | SEQ ID NO: 535 | ACGAGAGCACUUGAAAAUGAA | SEQ ID NO: 1178 | CAUUUUCAAGUGCUCUCGUUG | SEQ ID NO: 1821 | ACGAGAGCACUUGAAAAUG | 0.073 |
| AH0535 | SEQ ID NO: 536 | CGAGAGCACUUGAAAAUGAAA | SEQ ID NO: 1179 | UCAUUUUCAAGUGCUCUCGUU | SEQ ID NO: 1822 | CGAGAGCACUUGAAAAUGA | 0.026 |
| AH0536 | SEQ ID NO: 537 | GAGAGCACUUGAAAAUGAAAU | SEQ ID NO: 1180 | UUUCAUUUUCAAGUGCUCUCG | SEQ ID NO: 1823 | GAGAGCACUUGAAAAUGAA | 0.031 |
| AH0537 | SEQ ID NO: 538 | AGAGCACUUGAAAAUGAAAUG | SEQ ID NO: 1181 | UUUUCAUUUUCAAGUGCUCUC | SEQ ID NO: 1824 | AGAGCACUUGAAAAUGAAA | 0.059 |
| AH0538 | SEQ ID NO: 539 | GAGCACUUGAAAAUGAAAUGA | SEQ ID NO: 1182 | AUUUCAUUUUCAAGUGCUCUC | SEQ ID NO: 1825 | GAGCACUUGAAAAUGAAAU | 0.054 |
| AH0539 | SEQ ID NO: 540 | AGCACUUGAAAAUGAAAUGAC | SEQ ID NO: 1183 | CAUUUCAUUUUCAAGUGCUCU | SEQ ID NO: 1826 | AGCACUUGAAAAUGAAAUG | 0.032 |
| AH0540 | SEQ ID NO: 541 | GCACUUGAAAAUGAAAUGACU | SEQ ID NO: 1184 | UCAUUUCAUUUUCAAGUGCUC | SEQ ID NO: 1827 | GCACUUGAAAAUGAAAUGA | 0.074 |
| AH0541 | SEQ ID NO: 542 | CACUUGAAAAUGAAAUGACUG | SEQ ID NO: 1185 | GUCAUUUCAUUUUCAAGUGCU | SEQ ID NO: 1828 | CACUUGAAAAUGAAAUGAC | 0.204 |
| AH0542 | SEQ ID NO: 543 | ACUUGAAAAUGAAAUGACUGU | SEQ ID NO: 1186 | AGUCAUUUCAUUUUCAAGUGC | SEQ ID NO: 1829 | ACUUGAAAAUGAAAUGACU | 0.103 |
| AH0543 | SEQ ID NO: 544 | CUUGAAAAUGAAAUGACUGUC | SEQ ID NO: 1187 | CAGUCAUUUCAUUUUCAAGUG | SEQ ID NO: 1830 | CUUGAAAAUGAAAUGACUG | 0.121 |
| AH0544 | SEQ ID NO: 545 | UUGAAAAUGAAAUGACUGUCU | SEQ ID NO: 1188 | ACAGUCAUUUCAUUUUCAAGU | SEQ ID NO: 1831 | UUGAAAAUGAAAUGACUGU | 0.201 |
| AH0545 | SEQ ID NO: 546 | UGAAAAUGAAAUGACUGUCUA | SEQ ID NO: 1189 | GACAGUCAUUUCAUUUUCAAG | SEQ ID NO: 1832 | UGAAAAUGAAAUGACUGUC | 0.445 |
| AH0546 | SEQ ID NO: 547 | GAAAAUGAAAUGACUGUCUAA | SEQ ID NO: 1190 | AGACAGUCAUUUCAUUUUCAA | SEQ ID NO: 1833 | GAAAAUGAAAUGACUGUCU | 0.068 |
| AH0547 | SEQ ID NO: 548 | AAAAUGAAAUGACUGUCUAAG | SEQ ID NO: 1191 | UAGACAGUCAUUUCAUUUUCA | SEQ ID NO: 1834 | AAAAUGAAAUGACUGUCUA | 0.053 |
| AH0548 | SEQ ID NO: 549 | AAAUGAAAUGACUGUCUAAGA | SEQ ID NO: 1192 | UUAGACAGUCAUUUCAUUUUC | SEQ ID NO: 1835 | AAAUGAAAUGACUGUCUAA | 0.073 |
| AH0549 | SEQ ID NO: 550 | AAUGAAAUGACUGUCUAAGAA | SEQ ID NO: 1193 | CUUAGACAGUCAUUUCAUUUU | SEQ ID NO: 1836 | AAUGAAAUGACUGUCUAAG | 0.365 |
| AH0550 | SEQ ID NO: 551 | AUGAAAUGACUGUCUAAGAGA | SEQ ID NO: 1194 | UCUUAGACAGUCAUUUCAUUU | SEQ ID NO: 1837 | AUGAAAUGACUGUCUAAGA | 0.395 |
| AH0551 | SEQ ID NO: 552 | UGAAAUGACUGUCUAAGAGAU | SEQ ID NO: 1195 | CUCUUAGACAGUCAUUUCAUU | SEQ ID NO: 1838 | UGAAAUGACUGUCUAAGAG | 0.471 |

TABLE 1-continued

| Double stranded nucleic acid No. | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|
| AH0552 | GAAAUGACUGUCUAAGAGAUC | SEQ ID NO: 553 | UCUCUUAGACAGUCAUUUCAU | SEQ ID NO: 1196 | GAAAUGACUGUCUAAGAGA | 0.077 |
| AH0553 | AAAUGACUGUCUAAGAGAUCU | SEQ ID NO: 554 | AUCUCUUAGACAGUCAUUUCA | SEQ ID NO: 1197 | AAAUGACUGUCUAAGAGAU | 0.161 |
| AH0554 | AUGACUGUCUAAGAGAUCUGG | SEQ ID NO: 555 | AGAUCUCUUAGACAGUCAUUU | SEQ ID NO: 1198 | AUGACUGUCUAAGAGAUCU | 0.244 |
| AH0555 | UGACUGUCUAAGAGAUCUGGU | SEQ ID NO: 556 | CAGAUCUCUUAGACAGUCAUU | SEQ ID NO: 1199 | UGACUGUCUAAGAGAUCUG | 0.390 |
| AH0556 | GACUGUCUAAGAGAUCUGGUC | SEQ ID NO: 557 | CCAGAUCUCUUAGACAGUCAU | SEQ ID NO: 1200 | GACUGUCUAAGAGAUCUGG | 0.143 |
| AH0557 | ACUGUCUAAGAGAUCUGGUCA | SEQ ID NO: 558 | ACCAGAUCUCUUAGACAGUCA | SEQ ID NO: 1201 | ACUGUCUAAGAGAUCUGGU | 0.202 |
| AH0558 | CUGUCUAAGAGAUCUGGUCAA | SEQ ID NO: 559 | GACCAGAUCUCUUAGACAGUC | SEQ ID NO: 1202 | CUGUCUAAGAGAUCUGGUC | 0.119 |
| AH0559 | UGUCUAAGAGAUCUGGUCAAA | SEQ ID NO: 560 | UGACCAGAUCUCUUAGACAGU | SEQ ID NO: 1203 | UGUCUAAGAGAUCUGGUCA | 0.121 |
| AH0560 | GUCUAAGAGAUCUGGUCAAAG | SEQ ID NO: 561 | UUGACCAGAUCUCUUAGACAG | SEQ ID NO: 1204 | GUCUAAGAGAUCUGGUCAA | 0.053 |
| AH0561 | UCUAAGAGAUCUGGUCAAAGC | SEQ ID NO: 562 | UUUGACCAGAUCUCUUAGACA | SEQ ID NO: 1205 | UCUAAGAGAUCUGGUCAAA | 0.081 |
| AH0562 | CUAAGAGAUCUGGUCAAAGCA | SEQ ID NO: 563 | CUUUGACCAGAUCUCUUAGAC | SEQ ID NO: 1206 | CUAAGAGAUCUGGUCAAAG | 0.051 |
| AH0563 | UAAGAGAUCUGGUCAAAGCAA | SEQ ID NO: 564 | GCUUUGACCAGAUCUCUUAGA | SEQ ID NO: 1207 | UAAGAGAUCUGGUCAAAGC | 0.363 |
| AH0564 | AAGAGAUCUGGUCAAAGCAAC | SEQ ID NO: 565 | UGCUUUGACCAGAUCUCUUAG | SEQ ID NO: 1208 | AAGAGAUCUGGUCAAAGCA | 0.053 |
| AH0565 | AGAGAUCUGGUCAAAGCAACU | SEQ ID NO: 566 | UUGCUUUGACCAGAUCUCUUA | SEQ ID NO: 1209 | AGAGAUCUGGUCAAAGCAA | 0.091 |
| AH0566 | GAGAUCUGGUCAAAGCAACUG | SEQ ID NO: 567 | GUUGCUUUGACCAGAUCUCUU | SEQ ID NO: 1210 | GAGAUCUGGUCAAAGCAAC | 0.074 |
| AH0567 | AGAUCUGGUCAAAGCAACUGG | SEQ ID NO: 568 | AGUUGCUUUGACCAGAUCUCU | SEQ ID NO: 1211 | AGAUCUGGUCAAAGCAACU | 0.096 |
| AH0568 | GAUCUGGUCAAAGCAACUGGA | SEQ ID NO: 569 | CAGUUGCUUUGACCAGAUCUC | SEQ ID NO: 1212 | GAUCUGGUCAAAGCAACUG | 0.118 |
| AH0569 | AUCUGGUCAAAGCAACUGGAU | SEQ ID NO: 570 | CCAGUUGCUUUGACCAGAUCU | SEQ ID NO: 1213 | AUCUGGUCAAAGCAACUGG | 0.225 |
| AH0570 | UCUGGUCAAAGCAACUGGAUA | SEQ ID NO: 571 | UCCAGUUGCUUUGACCAGAUC | SEQ ID NO: 1214 | UCUGGUCAAAGCAACUGGA | 0.105 |
| AH0571 | CUGGUCAAAGCAACUGGAUAC | SEQ ID NO: 572 | AUCCAGUUGCUUUGACCAGAU | SEQ ID NO: 1215 | CUGGUCAAAGCAACUGGAU | 0.160 |
| AH0572 | UGGUCAAAGCAACUGGAUACU | SEQ ID NO: 573 | UAUCCAGUUGCUUUGACCAGA | SEQ ID NO: 1216 | UGGUCAAAGCAACUGGAUA | 0.093 |
| AH0573 | GGUCAAAGCAACUGGAUACUA | SEQ ID NO: 574 | GUAUCCAGUUGCUUUGACCAG | SEQ ID NO: 1217 | GGUCAAAGCAACUGGAUAC | 0.118 |
| AH0574 | GUCAAAGCAACUGGAUACUAG | SEQ ID NO: 575 | AGUAUCCAGUUGCUUUGACCA | SEQ ID NO: 1218 | GUCAAAGCAACUGGAUACU | 0.131 |
| AH0575 | UCAAAGCAACUGGAUACUAGA | SEQ ID NO: 576 | UAGUAUCCAGUUGCUUUGACC | SEQ ID NO: 1219 | UCAAAGCAACUGGAUACUA | 0.094 |

TABLE 1 -continued

| Double stranded nucleic acid No. | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|
| AH0576 | CAAAGCAACUGGAUACUAGAU | SEQ ID NO: 577 | CUAGUAUCCAGUUGCUUUGAC | SEQ ID NO: 1220 | CAAAGCAACUGGAUACUAG | 0.122 |
| AH0577 | AAAGCAACUGGAUACUAGAUC | SEQ ID NO: 578 | UCUAGUAUCCAGUUGCUUUGA | SEQ ID NO: 1221 | AAAGCAACUGGAUACUAGA | 0.089 |
| AH0578 | AAGCAACUGGAUACUAGAUCU | SEQ ID NO: 579 | AUCUAGUAUCCAGUUGCUUUG | SEQ ID NO: 1222 | AAGCAACUGGAUACUAGAU | 0.156 |
| AH0579 | AGCAACUGGAUACUAGAUCUU | SEQ ID NO: 580 | GAUCUAGUAUCCAGUUGCUUU | SEQ ID NO: 1223 | AGCAACUGGAUACUAGAUC | 0.248 |
| AH0580 | GCAACUGGAUACUAGAUCUUA | SEQ ID NO: 581 | AGAUCUAGUAUCCAGUUGCUU | SEQ ID NO: 1224 | GCAACUGGAUACUAGAUCU | 0.089 |
| AH0581 | CAACUGGAUACUAGAUCUUAC | SEQ ID NO: 582 | AAGAUCUAGUAUCCAGUUGCU | SEQ ID NO: 1225 | CAACUGGAUACUAGAUCUU | 0.067 |
| AH0582 | AACUGGAUACUAGAUCUUACA | SEQ ID NO: 583 | UAAGAUCUAGUAUCCAGUUGC | SEQ ID NO: 1226 | AACUGGAUACUAGAUCUUA | 0.101 |
| AH0583 | ACUGGAUACUAGAUCUUACAU | SEQ ID NO: 584 | GUAAGAUCUAGUAUCCAGUUG | SEQ ID NO: 1227 | ACUGGAUACUAGAUCUUAC | 0.096 |
| AH0584 | CUGGAUACUAGAUCUUACAUC | SEQ ID NO: 585 | UGUAAGAUCUAGUAUCCAGUU | SEQ ID NO: 1228 | CUGGAUACUAGAUCUUACA | 0.075 |
| AH0585 | UGGAUACUAGAUCUUACAUCU | SEQ ID NO: 586 | AUGUAAGAUCUAGUAUCCAGU | SEQ ID NO: 1229 | UGGAUACUAGAUCUUACAU | 0.115 |
| AH0586 | GGAUACUAGAUCUUACAUCUG | SEQ ID NO: 587 | GAUGUAAGAUCUAGUAUCCAG | SEQ ID NO: 1230 | GGAUACUAGAUCUUACACU | 0.087 |
| AH0587 | GAUACUAGAUCUUACAUCUGC | SEQ ID NO: 588 | AGAUGUAAGAUCUAGUAUCCA | SEQ ID NO: 1231 | GAUACUAGAUCUUACAUCU | 0.069 |
| AH0588 | AUACUAGAUCUUACAUCUGCA | SEQ ID NO: 589 | CAGAUGUAAGAUCUAGUAUCC | SEQ ID NO: 1232 | AUACUAGAUCUUACAUCUG | 0.105 |
| AH0589 | ACUAGAUCUUACAUCUGCAGC | SEQ ID NO: 590 | UGCAGAUGUAAGAUCUAGUAU | SEQ ID NO: 1233 | ACUAGAUCUUACAUCUGCA | 0.069 |
| AH0590 | CUAGAUCUUACAUCUGCAGCU | SEQ ID NO: 591 | CUGCAGAUGUAAGAUCUAGUA | SEQ ID NO: 1234 | CUAGAUCUUACAUCUGCAG | 0.091 |
| AH0591 | AGAUCUUACAUCUGCAGCUCU | SEQ ID NO: 592 | AGCUGCAGAUGUAAGAUCUAG | SEQ ID NO: 1235 | AGAUCUUACAUCUGCAGCU | 0.112 |
| AH0592 | GAUCUUACAUCUGCAGCUCUC | SEQ ID NO: 593 | GAGCUGCAGAUGUAAGAUCUA | SEQ ID NO: 1236 | GAUCUUACAUCUGCAGCUC | 0.096 |
| AH0593 | AUCUUACAUCUGCAGCUCUCU | SEQ ID NO: 594 | AGAGCUGCAGAUGUAAGAUCU | SEQ ID NO: 1237 | AUCUUACAUCUGCAGCUCU | 0.089 |
| AH0594 | UCUUACAUCUGCAGCUCUCUU | SEQ ID NO: 595 | AAGAGCUGCAGAUGUAAGAUC | SEQ ID NO: 1238 | UCUUACAUCUGCAGCUCUU | 0.083 |
| AH0595 | CUUACAUCUGCAGCUCUCUUU | SEQ ID NO: 596 | AAAGAGCUGCAGAUGUAAGAU | SEQ ID NO: 1239 | CUUACAUCUGCAGCUCUUU | 0.058 |
| AH0596 | UUACAUCUGCAGCUCUCUUUC | SEQ ID NO: 597 | GAAAGAGCUGCAGAUGUAAGA | SEQ ID NO: 1240 | UUACAUCUGCAGCUCUUUC | 0.110 |
| AH0597 | UACAUCUGCAGCUCUCUUUCU | SEQ ID NO: 598 | AGAAAGAGCUGCAGAUGUAAG | SEQ ID NO: 1241 | UACAUCUGCAGCUCUUUCU | 0.168 |
| AH0598 | ACAUCUGCAGCUCUCUUUCUC | SEQ ID NO: 599 | AAGAAAGAGCUGCAGAUGUAA | SEQ ID NO: 1242 | ACAUCUGCAGCUCUCUUU | 0.083 |
| AH0599 | CAUCUGCAGCUCUCUUUCUCU | SEQ ID NO: 600 | GAAGAAAGAGCUGCAGAUGUA | SEQ ID NO: 1243 | CAUCUGCAGCUCUUUCUUC | 0.072 |

TABLE 1-continued

| Double stranded nucleic acid No. | Sense strand sequence (5'--->3') | SEQ ID NO: | Antisense strand sequence (5'--->3') | SEQ ID NO: | Target APCS mRNA sequence | SEQ ID NO: | APCS relative expression level |
|---|---|---|---|---|---|---|---|
| AH0600 | AUCUGCAGCUCUUUCUUCUUU | SEQ ID NO: 601 | AGAAGAAAGAGCUGCAGAUGU | SEQ ID NO: 1244 | AUCUGCAGCUCUUUCUUCU | SEQ ID NO: 1887 | 0.072 |
| AH0601 | UCUGCAGCUCUUUCUUCUUUG | SEQ ID NO: 602 | AAAGAAGAAAGAGCUGCAGAUG | SEQ ID NO: 1245 | UCUGCAGCUCUUUCUUCUU | SEQ ID NO: 1888 | 0.086 |
| AH0602 | CUGCAGCUCUUUCUUCUUUGA | SEQ ID NO: 603 | AAAGAAGAAAGAGCUGCAGAU | SEQ ID NO: 1246 | CUGCAGCUCUUUCUUCUUU | SEQ ID NO: 1889 | 0.097 |
| AH0603 | UGCAGCUCUUUCUUCUUUGAA | SEQ ID NO: 604 | CAAAGAAGAAAGAGCUGCAGA | SEQ ID NO: 1247 | UGCAGCUCUUUCUUCUUUG | SEQ ID NO: 1890 | 0.096 |
| AH0604 | GCAGCUCUUUCUUCUUUGAAU | SEQ ID NO: 605 | UCAAAGAAGAAAGAGCUGCAG | SEQ ID NO: 1248 | GCAGCUCUUUCUUCUUUGA | SEQ ID NO: 1891 | 0.059 |
| AH0605 | CAGCUCUUUCUUCUUUGAAUU | SEQ ID NO: 606 | UUCAAAGAAGAAAGAGCUGCA | SEQ ID NO: 1249 | CAGCUCUUUCUUCUUUGAA | SEQ ID NO: 1892 | 0.054 |
| AH0606 | AGCUCUUUCUUCUUUGAAUUU | SEQ ID NO: 607 | AUUCAAAGAAGAAAGAGCUGC | SEQ ID NO: 1250 | AGCUCUUUCUUCUUUGAAU | SEQ ID NO: 1893 | 0.053 |
| AH0607 | GCUCUUUCUUCUUUGAAUUUC | SEQ ID NO: 608 | AAUUCAAAGAAGAAAGAGCUG | SEQ ID NO: 1251 | GCUCUUUCUUCUUUGAAUU | SEQ ID NO: 1894 | 0.057 |
| AH0608 | CUCUUUCUUCUUUGAAUUUCC | SEQ ID NO: 609 | GAAAUUCAAAGAAGAAAGAGC | SEQ ID NO: 1252 | CUCUUUCUUCUUUGAAUUU | SEQ ID NO: 1895 | 0.068 |
| AH0609 | UCUUUCUUCUUUGAAUUUCCU | SEQ ID NO: 610 | AGGAAAUUCAAAGAAGAAAGAG | SEQ ID NO: 1253 | UCUUUCUUCUUUGAAUUUC | SEQ ID NO: 1896 | 0.184 |
| AH0610 | CUUUCUUCUUUGAAUUUCCUA | SEQ ID NO: 611 | UAGGAAAUUCAAAGAAGAAAGA | SEQ ID NO: 1254 | CUUUCUUCUUUGAAUUUCC | SEQ ID NO: 1897 | 0.079 |
| AH0611 | UUUCUUCUUUGAAUUUCCUAU | SEQ ID NO: 612 | AUAGGAAAUUCAAAGAAGAAA | SEQ ID NO: 1255 | UUUCUUCUUUGAAUUUCCU | SEQ ID NO: 1898 | 0.124 |
| AH0612 | UUCUUCUUUGAAUUUCCUAUC | SEQ ID NO: 613 | GAUAGGAAAUUCAAAGAAGAA | SEQ ID NO: 1256 | UUCUUCUUUGAAUUUCCUA | SEQ ID NO: 1899 | 0.212 |
| AH0613 | UCUUCUUUGAAUUUCCUAUCU | SEQ ID NO: 614 | AGAUAGGAAAUUCAAAGAAGA | SEQ ID NO: 1257 | UCUUCUUUGAAUUUCCUAU | SEQ ID NO: 1900 | 0.259 |
| AH0614 | CUUCUUUGAAUUUCCUAUCUG | SEQ ID NO: 615 | CAGAUAGGAAAUUCAAAGAAG | SEQ ID NO: 1258 | CUUCUUUGAAUUUCCUAUC | SEQ ID NO: 1901 | 0.171 |
| AH0615 | UUCUUUGAAUUUCCUAUCUGU | SEQ ID NO: 616 | ACAGAUAGGAAAUUCAAAGAA | SEQ ID NO: 1259 | UUCUUUGAAUUUCCUAUCU | SEQ ID NO: 1902 | 0.194 |
| AH0616 | UCUUUGAAUUUCCUAUCUGUA | SEQ ID NO: 617 | UACAGAUAGGAAAUUCAAAGA | SEQ ID NO: 1260 | UCUUUGAAUUUCCUAUCUG | SEQ ID NO: 1903 | 0.073 |
| AH0617 | CUUUGAAUUUCCUAUCUGUAU | SEQ ID NO: 618 | AUACAGAUAGGAAAUUCAAAG | SEQ ID NO: 1261 | CUUUGAAUUUCCUAUCUGU | SEQ ID NO: 1904 | 0.072 |
| AH0618 | UUUGAAUUUCCUAUCUGUAUG | SEQ ID NO: 619 | CAUACAGAUAGGAAAUUCAAA | SEQ ID NO: 1262 | UUUGAAUUUCCUAUCUGUA | SEQ ID NO: 1905 | 0.104 |
| AH0619 | UUGAAUUUCCUAUCUGUAUGU | SEQ ID NO: 620 | ACAUACAGAUAGGAAAUUCAA | SEQ ID NO: 1263 | UUGAAUUUCCUAUCUGUAU | SEQ ID NO: 1906 | 0.151 |
| AH0620 | UGAAUUUCCUAUCUGUAUGUC | SEQ ID NO: 621 | ACAUACAGAUAGGAAAUUCAA | SEQ ID NO: 1264 | UGAAUUUCCUAUCUGUAUG | SEQ ID NO: 1907 | 0.066 |
| AH0621 | GAAUUUCCUAUCUGUAUGUCU | SEQ ID NO: 622 | AGACAUACAGAUAGGAAAUUC | SEQ ID NO: 1265 | GAAUUUCCUAUCUGUAUGU | SEQ ID NO: 1908 | 0.280 |
| AH0622 | AAUUUCCUAUCUGUAUGUCUG | SEQ ID NO: 623 | CAGACAUACAGAUAGGAAAUU | SEQ ID NO: 1266 | AUUUCCUAUCUGUAUGUCU | SEQ ID NO: 1909 | 0.222 |
| AH0623 | UUUCCUAUCUGUAUGUCUGCC | SEQ ID NO: 624 | GCAGACAUACAGAUAGGAAAU | SEQ ID NO: 1267 | UUCCUAUCUGUAUGUCUGC | SEQ ID NO: 1910 | 0.474 |

TABLE 1 -continued

| Double stranded nucleic acid No. | SEQ ID NO: | Sense strand sequence (5'--->3') | SEQ ID NO: | Antisense strand sequence (5'--->3') | SEQ ID NO: | Target APCS mRNA sequence | APCS relative expression level |
|---|---|---|---|---|---|---|---|
| AH0624 | SEQ ID NO: 625 | UCCUAUCUGUAUGUCUGCCUA | SEQ ID NO: 1268 | GGCAGACAUACAGAUAGGAAA | SEQ ID NO: 1911 | UCCUAUCUGUAUGUCUGCC | 0.494 |
| AH0625 | SEQ ID NO: 626 | CCUAUCUGUAUGUCUGCCUAA | SEQ ID NO: 1269 | AGGCAGACAUACAGAUAGGAA | SEQ ID NO: 1912 | CCUAUCUGUAUGUCUGCCU | 0.088 |
| AH0626 | SEQ ID NO: 627 | CUAUCUGUAUGUCUGCCUAAU | SEQ ID NO: 1270 | UAGGCAGACAUACAGAUAGGA | SEQ ID NO: 1913 | CUAUCUGUAUGUCUGCCUA | 0.073 |
| AH0627 | SEQ ID NO: 628 | UAUCUGUAUGUCUGCCUAAUU | SEQ ID NO: 1271 | UUAGGCAGACAUACAGAUAGG | SEQ ID NO: 1914 | UAUCUGUAUGUCUGCCUAA | 0.114 |
| AH0628 | SEQ ID NO: 629 | AUCUGUAUGUCUGCCUAAUUA | SEQ ID NO: 1272 | AUUAGGCAGACAUACAGAUAG | SEQ ID NO: 1915 | AUCUGUAUGUCUGCCUAAU | 0.073 |
| AH0629 | SEQ ID NO: 630 | UCUGUAUGUCUGCCUAAUUAA | SEQ ID NO: 1273 | AAUUAGGCAGACAUACAGAUA | SEQ ID NO: 1916 | UCUGUAUGUCUGCCUAAUU | 0.132 |
| AH0630 | SEQ ID NO: 631 | CUGUAUGUCUGCCUAAUUAAA | SEQ ID NO: 1274 | UAAUUAGGCAGACAUACAGAU | SEQ ID NO: 1917 | CUGUAUGUCUGCCUAAUUA | 0.051 |
| AH0631 | SEQ ID NO: 632 | UGUAUGUCUGCCUAAUUAAAA | SEQ ID NO: 1275 | UUAAUUAGGCAGACAUACAGA | SEQ ID NO: 1918 | UGUAUGUCUGCCUAAUUAA | 0.109 |
| AH0632 | SEQ ID NO: 633 | GUAUGUCUGCCUAAUUAAAAA | SEQ ID NO: 1276 | UUUAAUUAGGCAGACAUACAG | SEQ ID NO: 1919 | GUAUGUCUGCCUAAUUAAA | 0.091 |
| AH0633 | SEQ ID NO: 634 | UAUGUCUGCCUAAUUAAAAAA | SEQ ID NO: 1277 | UUUUAAUUAGGCAGACAUACA | SEQ ID NO: 1920 | UAUGUCUGCCUAAUUAAAA | 0.083 |
| AH0634 | SEQ ID NO: 635 | AUGUCUGCCUAAUUAAAAAAA | SEQ ID NO: 1278 | UUUUUAAUUAGGCAGACAUAC | SEQ ID NO: 1921 | AUGUCUGCCUAAUUAAAAA | 0.081 |
| AH0635 | SEQ ID NO: 636 | UGUCUGCCUAAUUAAAAAAAU | SEQ ID NO: 1279 | AUUUUUUAAUUAGGCAGACAUA | SEQ ID NO: 1922 | UGUCUGCCUAAUUAAAAAA | 0.113 |
| AH0636 | SEQ ID NO: 637 | GUCUGCCUAAUUAAAAAAAUA | SEQ ID NO: 1280 | UAUUUUUUAAUUAGGCAGACAU | SEQ ID NO: 1923 | GUCUGCCUAAUUAAAAAAA | 0.179 |
| AH0637 | SEQ ID NO: 638 | UCUGCCUAAUUAAAAAAAUAU | SEQ ID NO: 1281 | AUAUUUUUUAAUUAGGCAGACA | SEQ ID NO: 1924 | UCUGCCUAAUUAAAAAAAU | 0.113 |
| AH0638 | SEQ ID NO: 639 | CUGCCUAAUUAAAAAAAUAUA | SEQ ID NO: 1282 | UAUAUUUUUUAAUUAGGCAGAC | SEQ ID NO: 1925 | CUGCCUAAUUAAAAAAAUA | 0.043 |
| AH0639 | SEQ ID NO: 640 | UGCCUAAUUAAAAAAAUAUAU | SEQ ID NO: 1283 | AUAUAUUUUUUAAUUAGGCAGA | SEQ ID NO: 1926 | UGCCUAAUUAAAAAAAUAU | 0.151 |
| AH0640 | SEQ ID NO: 641 | GCCUAAUUAAAAAAAUAUAUA | SEQ ID NO: 1284 | UAUAUAUUUUUUAAUUAGGCAG | SEQ ID NO: 1927 | GCCUAAUUAAAAAAAUAUA | 0.191 |
| AH0641 | SEQ ID NO: 642 | CCUAAUUAAAAAAAUAUAUAU | SEQ ID NO: 1285 | AUAUAUAUUUUUUAAUUAGGCA | SEQ ID NO: 1928 | CCUAAUUAAAAAAAUAUAU | 0.361 |
| AH0642 | SEQ ID NO: 643 | CUAAUUAAAAAAAUAUAUAUU | SEQ ID NO: 1286 | UAUAUAUAUUUUUUAAUUAGGC | SEQ ID NO: 1929 | CUAAUUAAAAAAAUAUAUA | 0.287 |
| AH0643 | SEQ ID NO: 644 | UAAAAAAAUAUAUAUUGUAUU | SEQ ID NO: 1287 | UACAAUAUAUAUUUUUUUAAU | SEQ ID NO: 1930 | UAAAAAAAUAUAUAUUGUA | 0.376 |

Note that, the full length base sequence of the 2nd strand cDNA of APCS is shown in Table 2.

TABLE 2

| SEQ ID NO: 1 | gggcatgaatatcagacgctaggggacagccactgtgttgtctgc<br>taccctcatcctggtcactgcttctgctataacagccctaggccag<br>gaatatgaacaagccgctgctttggatctctgtcctcaccagcctc<br>ctggaagcctttgctcacacagacctcagtgggaaggtgtttgtat<br>ttcctagagaatctgttactgatcatgtaaacttgatcacaccgct<br>ggagaagcctctacagaactttaccttgtgttttcgagcctatagt<br>gatctctctcgtgcctacagcctcttctcctacaatacccaaggca<br>gggataatgagctactagtttataaagaaagagttggagagtatag<br>tctatacattggaagacacaaagttacatccaaagttatcgaaaag<br>ttcccggctccagtgcacatctgtgtgagctgggagtcctcatcag<br>gtattgctgaattttggatcaatgggacacctttggtgaaaaaggg<br>tctgcgacagggttactttgtagaagctcagcccaagattgtcctg<br>gggcaggaacaggattcctatgggggcaagtttgataggagccagt<br>cctttgtgggagagattgggatttgtacatgtgggactctgtgct<br>gccccagaaaatatcctgtctgcctatcagggtaccoctctccct<br>gccaatatcctggactggcaggctctgaactatgaaatcagaggat<br>atgtcatcatcaaaccccttggtgtgggtctgaggtcttgactcaac<br>gagagcacttgaaaatgaaatgactgtctaagagatctggtcaaag<br>caactggatactagatcttacatctgcagctctttcttctttgaat<br>ttcctatctgtatgtctgcctaattaaaaaaatatatattgtatta<br>tgctacctgcaaaaaaaaaaaaaaaaaaaaaaaaaaaaa |

Example 3 Knockdown Activity of Chemically Modified Double-Stranded Nucleic Acid Synthesis of sense-strand nucleic acids consisting of ribonucleotides represented by SEQ ID NOs: 1931 to 1974, and antisense-strand nucleic acids consisting of ribonucleotides represented by SEQ ID NOs: 1975 to 2018 were outsourced to Gene Design, Inc., and double-stranded nucleic acids were prepared by annealing them (sense-strands represented by SEQ ID NO: n (n=1931 to 1974) and the antisense-strands represented by SEQ ID NO: [n+44] are paired).

The final concentration of each of the double-stranded nucleic acids that was synthesized was set at 1 nM or 0.1 nM. The same operation as in Example 2 was repeated except that each of the double-stranded nucleic acids was introduced in RMG-1 cells and culture was carried out for 24 hours. The relative expression levels of APCS mRNAs were calculated. This experiment was repeated 4 times and median values of the relative expression levels of APCS mRNAs are shown in Table 3. In Table 3, N(M) represents 2'-O-methyl-RNA and N(F) represents 2'-F-RNA, wherein N represents A, C, G or U. For convenience sake, Table 3 will be separately shown as follows.

TABLE 3

| Double stranded nucleic acid No. | SEQ ID NO: | Sense strand sequence (5'--->3') | SEQ ID NO: | Antisense strand sequence (5'--->3') | APCS relative expression level (1 nM) | APCS relative expression level (0.1 nM) |
|---|---|---|---|---|---|---|
| AH0644 | SEQ ID NO: 1931 | U(F)A(M)C(F)C(M)U(F)U(M)G(F)U(M)G(F)U(M)U(F)U(F)G(M)A(F)C(M)G(F)G(M)C(F)C(M)U(F)A(M) | SEQ ID NO: 1975 | U(F)A(M)G(F)G(M)C(F)C(M)G(F)U(M)C(F)A(M)A(F)A(M)C(F)A(M)C(M)A(F)A(M)G(F)G(M)U(F)A(M)A(F)A(M) | 0.057 | 0.098 |
| AH0645 | SEQ ID NO: 1932 | U(F)C(M)C(F)U(M)U(F)A(M)C(F)A(M)G(F)C(M)C(F)U(M)C(F)U(M)C(F)A(M)C | SEQ ID NO: 1976 | U(F)A(M)G(F)G(M)C(F)G(M)A(F)G(M)G(F)C(M)U(F)G(M)U(F)A(M)A(F)G(M)G(F)A(M)G(F)G(M)A(F)G(M)G(F)G(M) | 0.083 | 0.130 |
| AH0646 | SEQ ID NO: 1933 | A(F)C(M)A(F)G(M)C(F)C(M)U(F)C(M)U(F)C(M)U(F)C(M)U(F)U(M)C | SEQ ID NO: 1977 | U(F)A(M)U(F)G(M)G(F)A(M)A(F)G(M)A(F)G(M)A(F)G(M)G(F)C(M)U(F)G(M)U(F)A(M)A(F)G(M)G(F)G(M) | 0.101 | 0.257 |
| AH0647 | SEQ ID NO: 1934 | G(F)U(M)C(F)C(M)U(F)U(M)A(F)U(M)U(F)C(M)A(F)A(M)G | SEQ ID NO: 1978 | U(F)C(M)A(F)C(M)C(F)U(M)U(F)G(M)A(F)A(M)U(F)A(M)A(F)G(M)G(F)A(M)C(M)U(F)C(F)A(M)U | 0.135 | 0.293 |
| AH0648 | SEQ ID NO: 1935 | A(F)G(M)G(F)A(M)G(F)C(M)C(F)A(M)G(F)U(M)U(F)U(M)C | SEQ ID NO: 1979 | U(F)C(M)C(F)C(M)A(F)A(M)A(F)C(M)U(F)G(M)G(F)C(M)U(F)C(F)C(M)U(F)G(M)A(F)U(M)A(F)G(M)A | 0.177 | 0.355 |
| AH0649 | SEQ ID NO: 1936 | G(F)A(M)G(F)G(M)A(F)A(M)G(F)C(M)C(F)U(M)G(F)U(M)C | SEQ ID NO: 1980 | U(F)C(M)U(F)C(M)C(F)C(M)A(F)C(M)A(F)G(M)G(F)C(M)U(F)U(F)C(M)C(F)U(M)C(F)A(M)G | 0.084 | 0.196 |
| AH0650 | SEQ ID NO: 1937 | C(F)C(M)A(F)G(M)G(F)C(M)U(F)U(M)C(F)C(M)U(F)U(M)G | SEQ ID NO: 1981 | A(F)U(M)C(F)U(M)C(F)C(M)A(F)G(M)G(F)C(M)U(F)U(M)C(F)C(F)U(M)U(F)G(M)G(F)U(M)A | 0.065 | 0.126 |
| AH0651 | SEQ ID NO: 1938 | C(F)A(M)G(F)G(M)C(F)A(M)G(F)U(M)G(F)A(M)U(F)G(M) | SEQ ID NO: 1982 | A(F)A(M)A(F)A(M)G(F)C(M)A(F)G(M)G(F)C(M)A(F)G(M)U(F)G(F)C(M)U(F)G(M)G(F)C(M) | 0.093 | 0.193 |
| AH0652 | SEQ ID NO: 1939 | U(F)G(M)G(F)G(M)A(F)G(M)A(F)U(M)U(F)U(M) | SEQ ID NO: 1983 | A(F)C(M)A(F)A(F)A(F)U(M)C(F)U(M)C(F)C(M)C(F)U(M)C(F)C(M)A(F)A(M) | 0.170 | 0.380 |
| AH0653 | SEQ ID NO: 1940 | G(F)G(M)G(F)G(M)G(F)A(M)A(F)U(M)U(F)G | SEQ ID NO: 1984 | U(F)C(M)A(F)A(M)C(F)C(M)A(F)U(F)C(F)M)U(F)C(M)A(F)C(M)C(F)C(M) | 0.152 | 0.300 |
| AH0654 | SEQ ID NO: 1941 | G(F)A(M)G(F)A(M)G(F)A(F)A(M)U(F)U(M)G | SEQ ID NO: 1985 | U(F)G(M)U(F)A(M)A(F)A(M)C(F)A(M)A(F)A(M)C(F)U(M)C(F)C(M) | 0.094 | 0.176 |
| AH0655 | SEQ ID NO: 1942 | C(F)C(M)C(F)M(F)A(M)U(F)U(M)C(F)C | SEQ ID NO: 1986 | U(F)A(M)A(F)G(M)C(F)A(M)U(F)U(M)G(F)A(M)G(F)G(M)A(F)C(F)C(M)U(F)G(M)A(F)U(M)G(F)G(M) | 0.123 | 0.332 |
| AH0656 | SEQ ID NO: 1943 | C(F)G(M)G(F)M(F)A(F)U(M)C(F)U(M)G | SEQ ID NO: 1987 | G(F)A(M)U(F)U(M)G(F)M(F)A(F)U(M)C(F)G(M)A(F)M(F)C(F)C(M) | 0.098 | 0.176 |
| AH0657 | SEQ ID NO: 1944 | G(F)A(M)G(F)M(F)A(F)U(M)C(F)U(M)C | SEQ ID NO: 1988 | G(F)U(M)G(F)U(M)G(F)M(F)A(F)G(M)C(F)A(M)A(F)C(M)A(F)C(F)A(M) | 0.147 | 0.338 |
| AH0658 | SEQ ID NO: 1945 | U(F)G(M)G(F)C(M)U(F)C(M)G(F)M(F)A(F)G(M) | SEQ ID NO: 1989 | U(F)G(M)A(F)M(F)A(F)C(M)A(F)M(F)C(F)A(M)C(F)C(F)A(M) | 0.103 | 0.203 |

TABLE 3-continued

| Double stranded nucleic acid No. | SEQ ID NO: | Sense strand sequence (5'--->3') | SEQ ID NO: | Antisense strand sequence (5'--->3') | APCS relative expression level (1 nM) | APCS relative expression level (0.1 nM) |
|---|---|---|---|---|---|---|
| AH0659 | SEQ ID NO: 1946 | A(F)C(M)U(F)C(M)A(F)A(M)C(F)G(M)A(F)G(M)A(F)G(F)C(M)A(F)C(M)A(F)U(F)M(F)A(F)A(M) | SEQ ID NO: 1990 | U(F)U(M)U(F)C(M)A(F)A(M)G(F)U(M)G(F)A(M)G(F)U(M)C(F)A(M)C(F)A(M)G(F)A(M)G(F)U(M)G(F)A(M)G(F)U(M)G(F)A(M) | 0.066 | 0.084 |
| AH0660 | SEQ ID NO: 1947 | C(F)U(M)C(F)A(M)A(F)C(M)G(F)A(M)G(F)A(M)G(F)C(M)A(F)C(M)A(F)U(M)U(F)A(M)A(F)A(M) | SEQ ID NO: 1991 | U(F)U(M)U(F)U(M)A(F)A(M)U(F)G(M)U(F)G(M)C(F)U(M)C(F)U(M)C(F)G(M)U(F)U(M)G(F)A(M)G(F)C(M)U | 0.067 | 0.066 |
| AH0661 | SEQ ID NO: 1948 | U(F)C(M)A(F)A(M)C(F)G(M)A(F)G(M)A(F)G(M)C(F)A(M)C(F)A(M)U(F)U(M)A(F)A(M)A(F)C | SEQ ID NO: 1992 | A(F)U(M)U(F)U(M)U(F)A(M)A(F)U(M)G(F)U(M)G(F)C(M)U(F)C(M)U(F)C(M)G(F)U(M)U(F)G(M)C | 0.058 | 0.074 |
| AH0662 | SEQ ID NO: 1949 | A(F)A(M)C(F)G(M)A(F)G(M)A(F)G(M)C(F)A(M)C(F)A(M)U(F)U(M)A(F)A(M)A(F)C(M)A | SEQ ID NO: 1993 | U(F)C(M)A(F)U(M)U(F)U(M)U(F)A(M)A(F)U(M)G(F)U(M)G(F)C(M)U(F)C(M)U(F)C(M)G(F)U(M)U(F)G(M)U | 0.046 | 0.091 |
| AH0663 | SEQ ID NO: 1950 | A(F)C(M)G(F)A(M)G(F)A(M)G(F)C(M)A(F)C(M)A(F)U(M)U(F)A(M)A(F)A(M)C(F)A(M)U | SEQ ID NO: 1994 | U(F)U(M)C(F)A(M)U(F)U(M)U(F)U(M)U(F)A(M)A(F)U(M)G(F)U(M)G(F)C(M)U(F)C(M)U(F)C(M)G(F) | 0.053 | 0.068 |
| AH0664 | SEQ ID NO: 1951 | C(F)G(M)A(F)G(M)A(F)G(M)C(F)A(M)C(F)A(M)U(F)U(M)A(F)A(M)A(F)C(M)A(F)U(M)U | SEQ ID NO: 1995 | U(F)U(M)U(F)C(M)A(F)U(M)U(F)U(M)U(F)A(M)A(F)U(M)G(F)U(M)G(F)C(M)U(F)C(M)U(F)C(M)G(F)M(F)A | 0.057 | 0.076 |
| AH0665 | SEQ ID NO: 1952 | G(F)A(M)G(F)A(M)G(F)C(M)A(F)C(M)A(F)U(M)U(F)A(M)A(F)A(M)C(F)A(M)U(F)U(M)G | SEQ ID NO: 1996 | A(F)U(M)U(F)U(M)U(F)U(M)C(F)A(M)U(F)U(M)U(F)U(M)A(F)A(M)U(F)G(M)U(F)G(M)C(F)U(M)C | 0.062 | 0.082 |
| AH0666 | SEQ ID NO: 1953 | A(F)G(M)A(F)G(M)C(F)A(M)C(F)A(M)U(F)U(M)A(F)A(M)A(F)C(M)A(F)U(M)U(F)G(M)A | SEQ ID NO: 1997 | A(F)A(M)A(F)U(M)U(F)U(M)U(F)C(M)A(F)U(M)U(F)U(M)U(F)A(M)A(F)U(M)G(F)U(M)G(F)C | 0.062 | 0.083 |
| AH0667 | SEQ ID NO: 1954 | C(F)U(M)G(F)G(M)U(F)C(M)A(F)A(M)A(F)A(M)G(F)C(M)A(F)U(M)U(F)C(M)U(F)G(M)U | SEQ ID NO: 1998 | C(F)A(M)C(F)A(M)G(F)A(M)A(F)U(M)G(F)C(M)U(F)U(M)U(F)U(M)C(F)U(M)C(F)A(M)G | 0.093 | 0.131 |
| AH0668 | SEQ ID NO: 1955 | C(F)U(M)G(F)G(M)U(F)C(M)A(F)A(M)A(F)A(M)G(F)C(M) | SEQ ID NO: 1999 | G(F)U(M)A(F)U(M)C(F)M(F)A(M)A(F)G(M)U(F)U(M)G(M)C | 0.157 | 0.319 |
| AH0669 | SEQ ID NO: 1956 | A(F)A(M)G(F)C(M)A(F)U(M)U(F)C(M)U(F)G(M)U(F)G(M)A | SEQ ID NO: 2000 | A(F)G(M)A(F)U(M)C(F)A(M)C(F)A(M)G(F)A(M)A(F)U(M)G(F)C(M)U | 0.083 | 0.126 |
| AH0670 | SEQ ID NO: 1957 | A(F)A(M)G(F)C(M)A(F)U(M)U(F)C(M)U(F)G(M)U(F)G(M)A(F)U(M)C(F)M(F)A(M)U | SEQ ID NO: 2001 | A(F)U(M)A(F)G(M)A(F)A(M)U(F)G(M)A(F)U(M)C(F)A(M)C(F)A(M)G(F)A(M)A(F)U(M)G(F)C(M)U | 0.071 | 0.129 |
| AH0671 | SEQ ID NO: 1958 | U(F)U(M)C(F)U(M)G(F)U(M)A(F)U(M)C(F)A(M)C(F)A(M)G(F)A(M)A(F)U(M)G(F)C(M)U | SEQ ID NO: 2002 | U(F)A(M)G(F)C(M)A(F)U(M)U(F)C(M)U(F)G(M)U(F)G(M)A(F)U(M)C(F)A(M)C(F)A(M)G(F)C(M)U | 0.115 | 0.181 |
| AH0672 | SEQ ID NO: 1959 | G(F)G(FC(M)A(F)U(M)U(F)A(M)C(F)C(M)A(F)A(M)U(F)C(M)C(F)A(M)M(F)U(M)U | SEQ ID NO: 2003 | C(F)A(M)A(F)A(M)G(F)A(M)G(F)M(F)C(M)A(F)A(M)A(F)A(M)A(F)M(F)G(M)C(F)M(F)M | 0.072 | 0.093 |
| AH0673 | SEQ ID NO: 1960 | U(F)C(M)A(F)C(M)C(F)U(M)U(F)G(M)G(F)M(F)C(M)A(F)A(M)G(F)C(M) | SEQ ID NO: 2004 | G(F)A(M)G(F)M(F)G(F)A(M)G(F)A(M)A(F)A(M)A(F)G(F)M(F)M(F)C(M)U(M)A(F)U(M) | 0.089 | 0.112 |
| AH0674 | SEQ ID NO: 1961 | A(F)C(M)A(F)M(F)C(F)U(M)M(F)M(F)M(F)M(F)M(F)C(M)U(F)M(F)M(F)M(F)C(M)A(F)G(M)C | SEQ ID NO: 2005 | A(F)G(M)A(F)M(F)A(F)G(M)A(F)A(F)G(M)A(F)M(F)A(F)M(F)U(M)G(F)M(F)A(F)U(M)G(F)M(F)A(F)A(M) | 0.067 | 0.082 |

TABLE 3 -continued

| Double stranded nucleic acid No. | SEQ ID NO: | Sense strand sequence (5'--->3') | SEQ ID NO: | Antisense strand sequence (5'--->3') | APCS relative expression level (1 nM) | APCS relative expression level (0.1 nM) |
|---|---|---|---|---|---|---|
| AH0675 | SEQ ID NO: 1962 | C(F)A(M)U(F)C(M)U(F)G(M)C(F)A(M)G(F)C(M)U(F)C(M)U(M)C(F)U(M)U(F)U(M)C(F)U(M)U(F)U(M) | SEQ ID NO: 2006 | A(F)A(M)G(F)A(M)A(F)G(M)A(F)A(M)A(F)G(M)A(F)G(M)A(F)C(M)A(F)A(M)G(F)A(M)G(F)A(M)U(F)A(M) | 0.098 | 0.114 |
| AH0676 | SEQ ID NO: 1963 | A(F)U(M)C(F)U(M)G(F)C(M)A(F)G(M)C(F)U(M)C(F)U(F)U(M)C(F)U(M)U(F)U(M) | SEQ ID NO: 2007 | A(F)A(M)A(F)G(M)A(F)A(M)G(F)A(M)A(F)G(M)A(F)A(M)G(F)A(M)G(F)A(M)C(F)A(M)G(F)A(M)U(F)U(M) | 0.093 | 0.144 |
| AH0677 | SEQ ID NO: 1964 | U(F)C(M)U(F)G(M)C(F)A(M)G(F)C(M)U(F)C(M)U(F)U(M)C(F)U(M)U(F)U(M)G(F)U(M) | SEQ ID NO: 2008 | C(F)A(M)A(F)A(M)A(F)G(M)A(F)A(M)A(F)G(M)A(F)A(M)G(F)A(M)G(F)A(M)C(F)A(M)G(F)A(M) | 0.084 | 0.093 |
| AH0678 | SEQ ID NO: 1965 | C(F)U(M)G(F)C(M)A(F)G(M)C(F)U(M)C(F)U(M)U(F)U(M)C(F)U(M)U(F)U(M)G(F)A(M) | SEQ ID NO: 2009 | U(F)C(M)A(F)A(M)A(F)G(M)A(F)A(M)A(F)G(M)A(F)A(M)G(F)A(M)G(F)A(M)C(F)A(M)G(F)A(M)U(F)U(M) | 0.089 | 0.100 |
| AH0679 | SEQ ID NO: 1966 | U(F)G(M)C(F)A(M)G(F)C(M)U(F)C(M)U(F)U(M)C(F)U(M)U(F)U(M)G(F)A(M)A(F)A(M) | SEQ ID NO: 2010 | U(F)U(M)C(F)A(M)A(F)A(M)G(F)A(M)A(F)A(M)G(F)A(M)A(F)G(M)A(F)G(M)A(F)C(F)A(M)G(F)A(M) | 0.101 | 0.158 |
| AH0680 | SEQ ID NO: 1967 | G(F)C(M)A(F)G(M)C(F)U(M)C(F)U(M)U(F)U(M)U(F)U(M) | SEQ ID NO: 2011 | A(F)U(M)U(F)C(M)A(F)A(M)A(F)G(M)A(F)A(M)A(F)G(M)A(F)G(M)A(F)C(F)G(M) | 0.086 | 0.112 |
| AH0681 | SEQ ID NO: 1968 | C(F)A(M)G(F)C(M)U(F)C(M)U(F)U(M)U(F)U(M) | SEQ ID NO: 2012 | A(F)A(M)U(F)U(M)C(F)A(M)A(F)A(M)G(F)A(M)A(F)A(M)G(F)A(M)A(F)G(M)A(F)G(M)A(F)C(F)A(M) | 0.088 | 0.119 |
| AH0682 | SEQ ID NO: 1969 | U(F)A(M)G(F)C(M)U(F)C(M)U(F)U(M)U(F)U(M) | SEQ ID NO: 2013 | A(F)C(M)A(F)A(M)U(F)U(M)C(F)A(M)A(F)A(M)G(F)A(M)A(F)A(M)G(F)A(M)A(F)G(M) | 0.052 | 0.064 |
| AH0683 | SEQ ID NO: 1970 | U(F)C(M)C(F)U(M)A(F)U(M)C(F)U(M)G(F)A(M) | SEQ ID NO: 2014 | U(F)A(M)G(F)C(M)A(F)U(M)U(F)C(M)A(F)A(M)A(F)G(M)A(F)A(M)A(F)U(M)A(F)A(M) | 0.062 | 0.089 |
| AH0684 | SEQ ID NO: 1971 | A(F)G(M)C(F)U(M)A(F)U(M)C(F)U(M)A(F)U(M)A(F)A(M) | SEQ ID NO: 2015 | U(F)C(M)A(F)G(M)C(F)C(M)U(F)A(M)A(F)U(M)A(F)C(M)A(F)U(M)A(F)G(M) | 0.055 | 0.083 |
| AH0685 | SEQ ID NO: 1972 | U(F)C(M)U(F)G(M)U(F)A(M)U(F)G(M)U(F)C(M)U(F) | SEQ ID NO: 2016 | U(F)U(M)A(F)A(M)U(F)U(M)A(F)U(M)G(F)G(M)C(F)A(M)G(F)A(M)G(F)A(M)( | 0.073 | 0.099 |
| AH0686 | SEQ ID NO: 1973 | C(F)U(M)G(F)U(M)A(F)U(M)A(F)U(M)G(F) | SEQ ID NO: 2017 | U(F)U(M)A(F)A(M)U(F)U(M)A(F)U(M)A(F)U(M)G(F)G(M)A(F)U(M) | 0.148 | 0.305 |
| AH0687 | SEQ ID NO: 1974 | G(F)U(M)C(F)U(M)A(F)A(M)A(F)A(M)A(F)A(M)U(F)A(M) | SEQ ID NO: 2018 | U(F)A(M)U(F)A(M)A(F)U(M)U(F)A(M)U(F)G(M)C(F)A(M)A(F)U(M) | 0.078 | 0.158 |

This application was filed based on Japanese Patent Application No. 2017-108502 (filing date: May 31, 2017), the entire contents of which are incorporated herein by reference.

Owing to the present invention, it is possible to provide a nucleic acid having an activity to suppress expression of APCS and a pharmaceutical composition comprising the nucleic acid as an active ingredient. The nucleic acid and pharmaceutical composition of the present invention can suppress expression of APCS and be used as a therapeutic or prophylactic agent for amyloid-related diseases.

Sequence Listing Free Text

SEQ ID NO: 1 represents the full-length base sequence of the 2nd strand cDNA of APCS.
SEQ ID NOs: 2 to 644 represent the base sequences of sense-strand nucleic acids.
SEQ ID NOs: 645 to 1287 represent the base sequences of antisense-strand nucleic acids.
SEQ ID NOs: 1288 to 1930 represent the base sequences of target APCS mRNA sequences.
SEQ ID NOs: 1931 to 1974 represent the base sequences of sense-strand nucleic acids.
SEQ ID NOs: 1975 to 2018 represent the base sequences of the antisense-strand nucleic acids.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11466272B2). An electronic copy of the "Sequence Listing" will also be available from the USPTO upon request and payment of the fee set forth in 37 CFR 1.19(b)(3).

The invention claimed is:

1. A double-stranded nucleic acid for suppressing expression of an APCS gene, the double-stranded nucleic acid consisting of a sense-strand nucleic acid and an antisense-strand nucleic acid and comprising a double-strand region having at least 11 base pairs, wherein the antisense-strand nucleic acid has a chain length of at least 17 nucleotides and at most 30 nucleotides wherein the antisense strand nucleic acid comprises a base sequence 5'-UU-CAAAGAAGAAAGAGC-3' (residues 1-17 of SEQ ID NO:1249) that is complementary to a target APCS mRNA sequence SEQ ID NO: 1894.

2. The double-stranded nucleic acid according to claim 1, wherein the double-strand region has 11 to 27 base pairs and a nucleotide at position 2 counted from the 5' end of the antisense-strand nucleic acid is complementary to a ribonucleotide at position 2 counted from 3' end of the target APCS mRNA sequence.

3. The double-stranded nucleic acid according to claim 1, wherein a 3' end of the sense-strand nucleic acid and the 5' end of the antisense-strand nucleic acid and/or the 5' end of the sense-strand nucleic acid and the 3' end of the antisense-strand nucleic acid form a blunt end.

4. The double-stranded nucleic acid according to claim 1, wherein the sense-strand nucleic acid consists of 21 nucleotides and the antisense-strand nucleic acid consists of 23 nucleotides.

5. The double-stranded nucleic acid according to claim 4, comprising a double-strand region having 17-21 base pairs, wherein 40 to 65% of the nucleotides in the double-strand region are 2'-O-methyl modified nucleotides.

6. The double-stranded nucleic acid according to claim 1, wherein the antisense-strand nucleic acid comprises the base sequence set forth in any one of SEQ ID NOS: 1249 to 1253.

7. The double-stranded nucleic acid according to claim 1, wherein the sense-strand nucleic acid comprises the base sequence set forth in any one of SEQ ID NOS: 606 to 610.

8. The double-stranded nucleic acid according to claim 1, wherein the sense-strand nucleic acid comprises the base sequence set forth in any one of SEQ ID NOS: 606 to 610, and correspondingly thereto, the antisense-strand nucleic acid comprises the base sequence set forth in any one of SEQ ID NOS: 1249 to 1253.

9. The double-stranded nucleic acid according to claim 1, comprising a ligand.

10. A single stranded nucleic acid consisting of 17 to 30 nucleotides and comprising the base sequence 5'-UU-CAAAGAAGAAAGAGC-3' (residues 1-17 of SEQ ID NO:1249).

11. A pharmaceutical composition comprising the double-stranded nucleic acid according to claim 1.

12. A method for suppressing expression of an APCS gene, comprising a step of administering the double stranded nucleic acid according to claim 1 to a human.

13. The double-stranded nucleic acid according to claim 1, wherein the antisense-strand nucleic acid consists of the base sequence 5'-AAUUCAAAGAAGAAAGAGCUGCA-3' (SEQ ID NO:2012).

14. The double-stranded nucleic acid according to claim 1, wherein the sense-strand nucleic acid consists of the base sequence 5'-CAGCUCUUUCUUCUUUGAAUU-3' (SEQ ID NO:1968), and the antisense-strand nucleic acid consists of the base sequence 5'-AAUU-CAAAGAAGAAAGAGCUGCA-3' (SEQ ID NO:2012).

* * * * *